US008962858B2

(12) United States Patent
Mitasev et al.

(10) Patent No.: US 8,962,858 B2
(45) Date of Patent: Feb. 24, 2015

(54) METHODS AND COMPOUNDS USEFUL IN THE SYNTHESIS OF FUSED AMINODIHYDROTHIAZINE DERIVATIVES

(71) Applicant: Eisai R&D Management Co., Ltd., Tokyo (JP)

(72) Inventors: Branko Mitasev, North Reading, MA (US); Dae-Shik Kim, Andover, MA (US); Huiming Zhang, Andover, MA (US); Christopher N. Farthing, London (GB)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 14/316,321

(22) Filed: Jun. 26, 2014

(65) Prior Publication Data
US 2014/0309429 A1 Oct. 16, 2014

Related U.S. Application Data

(62) Division of application No. 13/795,308, filed on Mar. 12, 2013, now Pat. No. 8,802,871, which is a division of application No. 13/355,030, filed on Jan. 20, 2012, now Pat. No. 8,426,584.

(60) Provisional application No. 61/434,849, filed on Jan. 21, 2011.

(51) Int. Cl.
C07D 498/04 (2006.01)
C07D 307/22 (2006.01)
C07D 513/04 (2006.01)

(52) U.S. Cl.
CPC ............ *C07D 307/22* (2013.01); *C07D 498/04* (2013.01); *C07D 513/04* (2013.01)
USPC .......................................... 548/242; 548/110

(58) Field of Classification Search
CPC ................................................... C07D 498/04
USPC ......................................................... 548/242
See application file for complete search history.

(56) References Cited

U.S. PATENT DOCUMENTS

| | | | |
|---|---|---|---|
| 3,227,713 | A | 1/1966 | Behner et al. |
| 3,235,551 | A | 2/1966 | Schubert et al, |
| 7,189,715 | B2 | 3/2007 | Jerussi et al. |
| 7,648,983 | B2 | 1/2010 | Audia et al. |
| 8,158,620 | B2 | 4/2012 | Suzuki et al. |
| 8,198,269 | B2 | 6/2012 | Motoki et al. |
| 2004/0110743 | A1 | 6/2004 | Miyamato et al. |
| 2007/0021454 | A1 | 1/2007 | Coburn et al. |
| 2008/0139538 | A1 | 6/2008 | McGaughey et al. |
| 2009/0082560 | A1 | 3/2009 | Kobayashi et al. |
| 2010/0075957 | A1 | 3/2010 | Tamura et al. |
| 2010/0093999 | A1 | 4/2010 | Motoki et al. |
| 2010/0160290 | A1 | 6/2010 | Kobayashi et al. |
| 2010/0317850 | A1 | 12/2010 | Suzuki et al. |
| 2011/0009395 | A1 | 1/2011 | Audia et al. |
| 2011/0152253 | A1 | 6/2011 | Motoki et al. |
| 2011/0207723 | A1 | 8/2011 | Motoki et al. |
| 2012/0094984 | A1 | 4/2012 | Suzuki et al. |
| 2012/0190672 | A1 | 7/2012 | Hall et al. |

FOREIGN PATENT DOCUMENTS

| | | |
|---|---|---|
| EP | 2 151 436 A1 | 2/2010 |
| EP | 2 233 474 A1 | 9/2010 |
| JP | 9067355 A | 3/1997 |
| JP | 2004-149429 | 5/2004 |
| WO | WO 01/87293 | 11/2001 |
| WO | WO 02/096897 | 12/2002 |
| WO | WO 2004/014843 | 2/2004 |
| WO | WO 2004/043916 | 5/2004 |
| WO | WO 2005/058311 | 6/2005 |
| WO | WO 2005/097767 | 10/2005 |
| WO | WO 2006/041404 | 4/2006 |
| WO | WO 2006/041405 | 4/2006 |
| WO | WO 2006/059234 | 6/2006 |
| WO | WO 2006/138264 A2 | 12/2006 |
| WO | WO 2007/011810 | 1/2007 |
| WO | WO 2007/049532 | 5/2007 |
| WO | WO 2007/114771 A1 | 10/2007 |
| WO | WO 2007/139230 | 12/2007 |
| WO | WO 2008/073365 A1 | 6/2008 |
| WO | WO 2008/133273 | 11/2008 |
| WO | WO 2008/133274 | 11/2008 |
| WO | WO 2009/067081 | 5/2009 |
| WO | WO 2009/091016 | 7/2009 |
| WO | WO 2009091016 A1 * | 7/2009 |
| WO | WO 2010/013302 | 2/2010 |
| WO | WO 2010/013794 | 2/2010 |
| WO | WO 2011/005738 A1 | 1/2011 |

(Continued)

OTHER PUBLICATIONS

N. Cohen et al. "Synthesis of 2-Amiro-5.6-dihydro-4H-1.3-thlazines and Related Compounds by Acid Catalyzed Cyclization of Allylic Isothiuronium Salts." Journal of Heterocyclic Chemistry. vol. 14(5). pp. 717-723 (Aug. 4, 1977).

C. H. Kuo et al. "A Synthesis of Estrone via Novel Intermediates, Mechanism of the Coupling Reaction of a Vinyl Cattinol with a p Diketone." Journal of Organic Chemistry, vol. 33, No. 8, pp. 3126-3132 (Aug. 1968).

Y. Gong et al. "Alzheimer's disease-affected brain: Presence of oligomeric Aβ ligands (ADDLs) suggests a molecular basis for reversible memory loss," Proceeding National Academy of Science USA, vol. 100. No. 18. pp. 10417-10422 (Sep. 2, 2003).

C. Hock et al. "Antibodies against n-Amyleid Slow Cognitive Decline in Alzheimer's Disease." Neuron. vol. 38. pp. 547-554 (May 22, 2003).

J. T. Jarrett et al. The Carboxy Terminus of the p Amyloid Protein is Critical for the Seeding of Amyloid Formation: Implications for the Pathogenesis of Alzheimer's Disease. Biochemistry. vol. 32. No. 18. pp. 4693-4697 (May 11, 1993).

G. G. Glenner et al. "Alzheimer's Disease: Initial report of the purification and characterization of a novel cerebrovascular amyloid protein." Biochemical and Biophysical Research Communications. vol. 120. No. 3. pp. 885-890 (May 16, 1984).

(Continued)

*Primary Examiner* — Kahsay Habte

(74) *Attorney, Agent, or Firm* — Myers Bigel Sibley & Sajovec, P.A.

(57) ABSTRACT

Provided are compounds and methods useful for the preparation of compounds useful as inhibitors of beta-site amyloid precursor protein (APP)-cleaving enzyme.

28 Claims, 3 Drawing Sheets

(56) References Cited

FOREIGN PATENT DOCUMENTS

| WO | WO 2011/009897 | 1/2011 |
|---|---|---|
| WO | WO 2011/009898 A1 | 1/2011 |
| WO | WO 2012/003274 | 1/2012 |

OTHER PUBLICATIONS

C. L. Masters et al. "Amyloid plaque core protein in Alzheimer disease and Down syndrome," Proceeding National Academy of Science USA, vol. 82, pp. 4245-4249 (Jun. 1985).
G. K. Gouras et al. "Intraneuronal A842 Accumulation in Human Brain," American Journal of Pathology. vol. 156. No. 1. pp. 15-20 (Jan. 2000).
D. Scheuner et al. "Secreted amylold p-protein similar to that in the senile plaques of Alzheimer's disease is increased in vivo by the presenilin 1 and 2 and APP mutations linked to familial Alzheimer's disease." Nature Medicine. vol. 2. No. 8. pp. 864-870 (Aug. 1996).
M.S. Forman et al. "Differential Effects of the Swedish Mutant Amyloid Precursor Protein on (β-Amylotd Accumulation and Secretion in Neurons and Nonneuronal Cells." The Journal of Bloloalcal Chemistry. vol. 272. No. 51. pp. 32247-32253 (Dec. 19, 1997).
S. Sankaranarayanan et al.. "In Vivo p-Secretase 1 Inhibition Leads to Brain Aβ Lowering and Increased α-Secretase Processing of Amyloid Precursor Protein without Effect on Neuregulin-1," The Journal of Pharmacology and Experimental Therapeutics, vol. 324, No. 3. pp. 957-969 (2008).
Khimiya I Khimicheskava Tekholoqiya, vol. 33. No. 10. pp. 15-18 (1990).
Bobrov et al., "Interaction of Quinone Oxide with Thiourea" Chemistry and Chemical Technology 33(10): 15-18 (1990) (original and English language translation).
L. C. Cross et al., International Union of Pure and Applied Chemistry (IUPAC) Rules for the Nomenclature of Organic Chemistry. Section E, Stereochemistry. Pure & Applied Chemistry 45: 11-30 (1976).
Heany F and O'Mahony C. The influence of oxime stereochemistry in the generation of nitrones from omega-alkenyloximes by cyclization or 1,2-prototropy. J Chem Soc, Perkin Trans. Jan. 1, 1998; 1: 341-349.
Liu Y et al. A practical and chemoselective reduction of nitroarenes to anilines using activated iron. Adv synth Caral. 2005; 347: 217-219.
International Search Report and Written Opinion, PCT/US2012/022053, mailed Apr. 19, 2012.
Ames, B. et al., "Methods for Detecting Carcinogens and Mutagens With the *Salmonella*/Mammalian-Microsome Mutagenicity Test", *Mutation Research*, vol. 31, 1975, pp. 347-350.
Arnone A. et al., "An Enantiospecific Entry to Fluoro Substituted Aminocyclopentanols through Intramolecular Nitrile Oxide, Nitrone, and Oxime Cycloaddition Reactions", *Tetrahedron:Asymmetry*, vol. 5, No. 6, pp. 1019-1028, 1994.
Aschwanden P. et al., "Reduction of 2,3-Dihydroisoxazoles to β-Amino Ketones and β-Amino Alcohols", *Organic Letters*, 2005, vol. 7, No. 25, pp. 5741-5742.
Australian Examination Report Corresponding to Application No. 2009205072; Dated: Jul. 19, 2012; 2 Pages.
Berge S.M. et al., "Pharmaceutical Salts", *Journal of Pharmaceutical Sciences*, Jan. 1977, vol. 66, No. 1, pp. 1-19.
Bobrov A.I. et al., "Interaction of quinone oxide with thiourea", *Chemistry and Chemical Technology*, vol. 33, No. 10, pp. 15-18, 1991 (Translation).
Brzostowska M. et al., "Chiral Prodyes: Synthesis and Full Characterization of (S)-1-Phenylethylamides of the Optically Active Ω-Methyldihydrofluoresceins", *Heterocylces*, vol. 32, No. 10, 1991.
Canadian Office Action Corresponding to Application No. 2711655; Dated: Jun. 5, 2012, 4 Pages.
Chakrabarty M. et al,, "DBU, A Highly Efficient Reagent for the Facile Regeneration of (Hetero)Arylamines From Their Acetamides and Benzamides: Influence of Solvent, Temperature, and Microwave Irradiation" Synthetic Communications, vol. 32, No. 2, 2002, pp. 265-272.
Chilean Application No. 96-2009; Office Action Response; Nov. 4, 2011; 705 Pages.

Chilean Examiners Report Corresponding to Application No. 702-11; Dated May 14, 2012; 19 Pages (Foreign Text and English Translation).
Chilean Examiners Report Corresponding to Application No. 96-2009, Dated Aug. 2011; 30 Pages.
Chilean Office Action Corresponding to Application No. 96-09; Dated; Aug. 1, 2011; 30 Pages (Foreign Text and English Translation).
Chilean Office Action Corresponding to Application No. 96-09; Dated: Dec. 12, 2011; 15 Pages.
Chilean Office Action Corresponding to Application No. 962009; Sep. 2011; 13 Pages.
Chinese Office Action Corresponding to Application No. 200980101688.X; Dated: Apr. 1, 2012; 9 Pages (Foreign Text and English Translation).
Cohen, N. et al., "Synthesis of 2-Amino-5,6-dihydro-4H-1,3-thiazines and Related Compounds by Acid Catalyzed Cyclization of Allylic Isothiuronium Salts", *J. Heterocyclic Chem.*,vol. 14, Aug. 1977, pp. 717-723.
Cross L.C. et al., "Rules for the Nomenclature of Organic Chemistry, Section E: Stereochemistry", *Pure & Appl. Chem.*, vol. 45, No. 1-B, pp. 11-30, 1976.
European Search Report Corresponding to European Application No. 09817719.9; Dated: Feb. 14, 2012; 6 Pages.
European Search Report Corresponding to European Application No. 09701914.5; Dated: Sep. 30, 2011; 5 Pages.
Forman M.S. et al., "Differential Effects of the Swedish Mutant Amyloid Precursor Protein on β-Amyloid Accumulation and secretion in Neurons and Nonneuronal Cells", *The Journal of Biological Chemistry*, vol. 272, No. 51, Dec. 19, 1997, pp. 32257-32253.
Glenner G.G. et al., "Alzheimer's Disease; Initial Report of the Purification and Characterization of a Novel Cerebrovascular Amyloid Protein", *Biochemical and Biophysical Research Communications*, vol. 120, No. 3, 1984, pp. 885-890.
Gloor, S.M. et al., "Molecular and cellular permeability control at the blood-brain barrier", *Brain Research Reviews*, vol. 36, 2001, pp. 258-264.
Gong Y. et al., "Alzheimer's disease-affected brain; Prescence of oligomeric Aβ ligands (ADDLs) suggest a molecular basis for reversible memory loss", *PNAS*, vol. 100, No. 18, Sep. 2, 2003, pp. 10417-10422.
Gouras G.K. et al., "Intraneuronal Aβ42 Accumulation Human Brain", *American Journal of Pathology*, vol. 156, No. 1, Jan. 2000, pp. 15-20.
Green M.H.L. et al., "Mutagen Testing Using TRP Reversion in *Escherichia Coli*", *Mutation Research*, vol. 38, 1976, pp. 3-32.
Green T.W. et al, "*t*-Butyl Ester: $RCO_2C(CH_3)_3$ (Chart 6)", *Protection for the Carboxyl Group*, pp. 404-408, 1999.
Green T.W. et al., "*t*-Butyl (BOC) Carbamate; $(CH_3)_3COC(O)NR_2$ (Chart 8)", *Protection for the Amino Group*, pp. 518-525, 1999.
He H. et al., "Utility of unbound plasma drug levels and P-glycoprotein transport data in prediction of central nervous system exposure", *Xenobiotica*, 2009, vol. 39, No. 9, pp. 687-693.
Heaney F. at al,, "The influence of oxime stereochemistry in the generation of nitrones from ω-alkenyloximes by cyclization or 1,2-prototropy", *J. Chem. Soc., Perkin Trans.*, vol. 1, 1998, pp. 341-349.
Hitchcock S.A. et al., "Structure-Brain Exposure Relationships", *Journal of Medicinal Chemistry*, vol. 49, No. 26, Dec. 28, 2006, pp. 7559-7582.
Hock C. et al., "Antibodies against β-Amyloid Slow Cognitive Decline in Alzheimer's Disease", *Neuron*, vol. 38, May 22, 2003, pp. 547-554.
Howbert, J.J. et al., "Novel Agents Effective against Solid Tumors: The Diarylsulfonylureas, Synthesis, Activities, and Analysis of Quantitative Structure-Activity Relationships", *J. Med. Chem*, vol. 33, No. 9, 1990, pp. 2393-2407.
Hussain I. et al., "Oral administration of a potent and selective non-peptidic BACE-1 inhibitor decreases β-cleavage of amyloid precursor protein and amyloid-β production in vivo" *Journal of Neurochemistry*, 2007, vol. 100, pp. 802-809.
International Preliminary Report Corresponding to International Application No. PCT/JP2009/050511; Date of issuance of this report; Aug. 31, 2010; 5 Pages.

(56) References Cited

OTHER PUBLICATIONS

International Search Report Corresponding to International Application No. PCT/JP2009/050511; Date of Mailing: Mar. 24, 2009, 2 Pages.
International Search Report Corresponding to International Application No. PCT/EP2012/050833; Date of Mailing: Apr. 18, 2012; 9 Pages.
Iserloh U. et al., "Discovery of an orally efficacious 4-phenoxypyrrolidine-based BACE-1 inhibitor", *Bioorganic & Medicinal Chemistry Letters*, vol. 18, 2008, pp. 418-422.
Ishikawa T. et al., "Synthesis of A-Ring Fragments of 1α,25-Dihydroxyvitamin $D_3$ and Taxane Diterpenoids: Effective Construction of Conjugated Formylcyclohexene Frameworks from Isoxazolines", *Tetrahedron*, vol. 54, 1998, pp. 5869-5882.
Japanese Argument Corresponding to Japanese Patent Application No. 2009-550050; Filing Date: Apr. 12, 2010, 49 Pages.
Japanese Decision of Granting Patent Corresponding to Japanese Patent Application No. 2009-5500550; Mailing Date: May 7, 2010; 6 Pages.
Japanese Office Action Corresponding to Application No. 2009-550050; Mailing Date: Feb. 9, 2011.
Jarrett J.T. et al., "The Carboxy Terminus of the β Amyloid Protein Is Critical for the Seeding of Amyloid Formation: Implications for the Pathogenesis of Alzheimer's Disease", *Biochemistry*, vol. 32, No. 18, May 11, 1993, 4693-4697.
Kalvass J.C. et al., "Influence of Nonspecific Brain and Plasma Binding on CNS Exposure: Implications for Rational Drug Discovery", *Biopharmaceutics & Drug Disposition*, vol. 23, 2002, pp. 327-338.
Katagiri N. et al., "Synthesis of Chiral Spiro 3-Oxazolin-5-one 3-Oxides (Chiral Nitrones) via a Nitrosoketene Intermediate and Their Asymmetric 1,3-Dipolar Cycloaddition Reactions Leading to the EPC Synthesis of Modified Amino Acids", *Tetrahedron*, vol. 53, No. 16, pp. 5725-5746, 1997.
Kuo C.H. et al., "A Synthesis of Estrone vai Novel Intermediates. Mechanism of the Coupling Reaction of a Vinyl Carbinol with a β Diketone", *The Journal of Organic Chemistry*, vol. 33, No. 8, Aug. 1968, pp. 3126-3132.
Kusuhara H. et al., "Efflux transport systems for drugs at the blood-brain barrier and blood-cerebrospinal fluid barrier (Part 1)", *DDT*, vol. 6, No. 3, Feb. 2001, pp. 150-156.
Lin J.H. "How Significant Is the Role of P-Glycoprotein in Drug Absorption and Brain Uptake?", *Drugs of Today*, 2004, vol. 40, No. 1, pp. 5-22.
Lin J.H. et al., "Role of P-Glycoprotein in Pharmacokinetics", *Clin. Pharmacokinet*, 2003, vol. 42, No. 1, pp. 59-98.
Liu Y. et al., "A Practical and Chemoselective Reduction of Nitroarenes to Anilines Using activated Iron", *Adv. Synth. Catal.* 2005, vol. 347, pp. 217-219.
Mahar Doan K.M. et al., "Passive Permeability and P-Glycoprotein-Mediated Efflux Differentiate Central Nervous System (CNS) and Non-CNS Marketed Drugs", *The Journal of Pharmacology and Experimental Therapeutics*, vol. 303, No. 3, 2002, pp. 1029-1037.
Malamas M.S. et al., "Design and synthesis of aminohydantoins as potent and selective human β-secretase (BACE1) inhibitors with enhanced brain permeability", *Bioorganic & Medicinal Chemistry Letters*, vol. 20, 2010, pp. 6597-6605.
Masters C.L. et al., "Amyloid plaque core protein in Alzheimer disease and Down syndrome", *Proc. Natl. Acad. Sci, USA*, vol. 82, 1985, pp. 4245-4249.
Maurer T.S. et al., "Relationship Between Exposure and Nonspecific Binding of Thirty-Three Central Nervous System Drugs in Mice", *Drug Metabolism and Disposition*, vol. 33, 2005, pp. 175-181.
McCann J. et al., "Detection of carcinogens as mutagens in the *Salmonella*/microsome test: Assay of 300 chemicals", *Proc. Nat. Acad. Sci. USA*, vol. 72, No. 12, pp. 5135-5139, Dec. 1975.
McCann J. et al., "Detection of carcinogens as mutagens in the *Salmonella*/microsome test: Assay of 300 chemicals: Discussion", *Proc. Nat. Acad. Sci. USA*, vol. 73, No. 3, Mar. 1976, pp. 950-954.

Meredith J.E. et al., "P-Glycoprotein Efflux and Other Factors Limit Brain Amyloid β Reduction by β-Site Amyloid Precursor Protein-Cleaving Enzyme 1 Inhibitors in Mice", *The Journal of Pharmacology and Experimental Therapeutics*, vol. 326, No. 2, 2008, pp. 502-513.
Mexican Office Action Corresponding to Application No. MX/a/2010/007337; Dated: Oct. 19, 2011; 5 Pages.
Mexican Office Action Corresponding to Application No. MX/a/2011/003189; Dated: Jun. 25, 2012; 3 Pages.
Mexican Response to Office Action Corresponding to Mexican Application No. MX/a/2010/007337; Dated: Jan. 3, 2012; 9 Pages.
Mexican Translation of the Requirements Stated by the Examiner Corresponding to Mexican Application No. MX/a/2010/007337; 2011.
Nahm S. et al., "N-Methoxy-N-Methylamides as Effective Acylating Agents", *Tetrahedron Letters*, vol. 22, No. 39, 1981, pp. 3815-3818.
New Zealand Argument Corresponding to New Zealand Patent Application No. 586796; Dated, Apr. 28, 2011.
New Zealand Examination Report and Notice of Acceptance of Complete Specification Corresponding to New Zealand Application No. 586796; Dated: Oct. 6, 2011.
New Zealand Examination Report Corresponding to Application No. 586796; Dated: Feb. 21, 2011.
Newspaper, Venezuelan Newspaper Corresponding to Application No. 2009000078; Aug. 25, 2011.
Non-Final Office Action Corresponding to U.S. Appl. No. 13/354,716; Notification Date: Jun. 19, 2012; 11 Pages.
Notice of Acceptance Corresponding to New Zealand Application No. 591878; Dated: May 17, 2012.
Notice of Allowance Corresponding to U.S. Appl. No. 12/355,154; Date Mailed: Jan. 18, 2012.
Notice of Allowance Corresponding to U.S. Appl. No. 12/355,154; Date Mailed: Feb. 17, 2012.
Notice of Allowance Corresponding to U.S. Appl. No. 12/355,154; Date Mailed: Oct. 5, 2011.
Notice of Allowance Corresponding to U.S. Appl. No. 12/668,151; Date Mailed: Jan. 4, 2012.
Notice of Allowance Corresponding to U.S. Appl. No. 13/354,716; Date Mailed: Oct. 2, 2012; 5 Pages.
Pakistan Argument Corresponding to Pakistan Patent Application No. 43/2009; Dated, May 21, 2010.
Pakistan Examination Report Corresponding to Application No. 35/2012, 2012, 2 Pages.
Pakistan Office Action Corresponding to Application No. 43/2009; Dated: Mar. 26, 2010.
Pakistan Official Notice of Acceptance Corresponding to Application No. 43/2009; Dated: Jun. 10, 2010; 1 Page.
Prakash Surya G.K. et al., "Perfluoroalkylation with Organosilicon Reagents", *Chem. Rev.* 1997, vol. 97, pp. 757-786.
Response to Chilean Office Action Corresponding to Chilean Application No. 96/2009; Dated: Mar. 22, 2012; 33 Pages.
Response to Chinese Office Action Corresponding to Chinese Application No. 200980101688; Dated: Jun. 15, 2012; 88 Pages (Foreign Text and English Translation).
Response to Office Action Corresponding to U.S. Appl. No. 13/354,716; Sep. 19, 2012; 19 Pages.
Response to Office Action Corresponding to U.S. Appl. No. 12/355,154; Dated: Jan. 5, 2012; 37 Pages.
Response to Office Action Corresponding to U.S. Appl. No. 12/355,154; Dated: Sep. 2, 2011; 37 Pages.
Response to Office Action Corresponding to U.S. Appl. No. 12/355,154; Dated: Sep. 27, 2011; 10 Pages.
Response to Office Action Corresponding to U.S. Appl. No. 12/568,151; Dated: Dec. 22, 2011; 82 Pages.
Response to Restriction Requirement for U.S. Appl. No. 12/355,154; Dated: May 19, 2011; 20 Pages.
Response to Singapore Office Action Corresponding to Application No. 201102027-8; Dated: Dec. 28, 2011; 102 Pages.
Response to Written Opinion Corresponding to Singapore Patent Application No. 201102027-8; Dated: Jul. 5, 2012; 5 Pages.
Restriction Office Action Corresponding to U.S. Appl. No. 12/355,154; Notification Date: Apr. 19, 2011; 9 Pages.

(56) References Cited

OTHER PUBLICATIONS

Romero D.L. et al., "Discovery, Synthesis, and Bioactivity of Bis(heteroaryl)piperazines. 1. A Novel Class of Non-Nucleoside HIV-1 Reverse Transcriptase Inhibitors", *J. Med. Chem.* 1994, vol. 37, pp. 999-1014.
Rosowsky A. et al., "Synthesis and Biological Activity of the 2-Desamino and 2-Desamino-2-methyl Analogues of Aminopterin and Methotrexate", *J. Med. Chem.*, 1991, vol. 34, pp. 227-234.
Russian Office Action Corresponding to Application No. 2010134403/04(048821); Dated: May 14, 2012, 7 Pages (Foreign Text and English Translation).
Sankaranarayanan S. et al., "First Demonstration of Cerebrospinal Fluid and Plasma Aβ Lowering with Oral Administration of a β-Site Amyloid Precursor Protein-Cleaving Enzyme 1 Inhibitor in Nonhuman Primates", *The Journal of Pharmacology and Experimental Therapeutics*, vol. 328, No. 1, 2009, pp. 131-140.
Sankaranarayanan S. et al., "In Vivo β-Secretase 1 inhibition Leads to Brain Aβ Lowering and Increased α-Secretase Processing of Amyloid Precursor Protein without Effect on Neuregulin-1", *The Journal of Pharmacology and Experimental Therapeutics*, vol. 324, No. 3, 2008, pp. 957-969.
Scheuner D. et al., "Secreted amyloid β-protein similar to that in the senile plaques of Alzheimer's disease is increased in vivo by the presenilin 1 and 2 and APP mutations linked to familial Alzheimer's disease", *Nature Medicine*, vol. 2, No. 8, Aug. 1996, pp. 864-870.
Schinkel A.H. et al., "P-Glycoprotein, a gatekeeper in the blood-brain barrier", *Advanced Drug Delivery Reviews*, vol. 36, 1999, pp. 179-194.
Shing T.K.M. et al., "Intramolecular Nitrile Oxide-Alkene Cycloaddition of Sugar Derivatives with Unmasked Hydroxyl Group(s)", *Organic Letters*, vol. 9, No. 5, 2007, pp. 753-756.
Summerfield S.G. et al., "Central Nervous System Drug Disposition: The Relationship between in situ Brain Permeability and Brain Free Fraction", *The Journal of Pharmacology and Experimental Therapeutics*, vol. 322, 2007, pp. 205-213.
Trainor G.L. et al., "The importance of plasma protein binding in drug discovery", *Expert Opin. Drug Discov.*, 2007, vol. 2, No. 1, pp. 51-64.
Tzvetkov N.T. et al., "Synthesis and photoinitiated radical cyclization of allyl- and propynyloxymethyl substituted cyclopentanones to tetrahydrocyclopenta[c]furanols", *Tetrahedron Letters*, vol. 46, 2005, pp. 7751-7755.
U.S. Office Action Corresponding to U.S. Appl. No. 12/355,154; Notification Date: Jun. 3, 2011, 9 Pages.
U.S. Office Action Corresponding to U.S. Appl. No. 12/568,151; Notification Date: Oct. 24, 2011; 10 Pages.
U.S. Office Action Corresponding to U.S. Appl. No. 13/333,238; Notification Date: Jun. 18, 2012; 15 Pages.
Ueno M, "Molecular Anatomy of the Brain Endothelial Barrier: An Overview of the Distributional Features", *Current Medicinal Chemistry*, 2007, vol. 14, pp. 1199-1206.
Ukraine Decision Corresponding to Ukraine Application No. 4672/3A/12; Dated: Feb. 23, 2012; 16 Pages (Foreign Text and English Translation).
Uno H. et al., "Reaction of 2-Isoxazolines with Organolithiums in the Presence of Boron Trifluoride", *Bull. Chem. Soc. Jpn.*, vol. 66, No. 9, 1993, pp. 2730-2737.
Whisler M.C. et al., "Synthetic Applications of Lithiated N-Boc Allylic Amines as Asymmetric Homoenolate Equivalents", *J. Org. Chem.*, 2003, vol. 68, pp. 1207-1215.
Written Opinion Corresponding to Singapore Application No. 201102027-8; Date of Mailing: Mar. 15, 2012; 10 Pages.
Written Opinion for Singapore Application No. 201102027-8; Dated: Aug. 24, 2011; 11 Pages.
Abdel-Magid et al. "Reductive Amination of Aldehydes and Ketones with Sodium Triacetoxyborohydride. Studies on Direct and Indirect Reductive Amination Procedures", *J. Org. Chem.*, 1996, 61, 3849-3862.

Arranyos et al. "Novel Electron-Rich Bulky Phosphine Ligands Facilitate the Palladium-Catalyzed Preparation of Diaryl Ethers", *J. Am. Chem. Soc.*, 1999, 121, 4369-4378.
Barange et al. "A Remarkable Accelerating Effect of Ag-Salt on Intramolecular Cyclization of o-(1-Alkynyl)benzenesulfonamides", *J. Org. Chem.*, 2007, 72, 8547-8550.
Barlow et al. "Intervalence Transitions in the Mixed-Valence Monocations of Bis(triarylamines) Linked with Vinylene and Phenylene-Vinylene Bridges", *J. Am. Chem. Soc.*, 2005, 127, 16900-16911.
Butler et al. "A Facile Synthesis of New 5H-Indazolo[3,2-b]benzo[d]-1,3-oxazines via One-Pot Intramolecular Bis-heterocyclizations", *J. Org. Chem.*, 2008, 73, 234-240.
Coates et al. "Annotative Ring Expansion via Intramolecular [2+2] Photocycloaddition of αβ-Unsaturated Y-Lactones and Reductive Cleavage: Synthesis of Hydrocyclopentacyclooctene-5-carboxylates", *The Journal of Organic Chemistry*, vol. 47, No. 19, Sep. 10, 1982, 11 pages.
Crisp et al. "Palladium-Catalyzed, Carbonylative, Intramolecular Coupling of Hydroxy Vinyl Triflates, Synthesis of Substituted αβ-Butenolides", *J. Org. Chem.*, 1992, 57, 6972-6975.
Danheiser et al. "An Annulation Method for the Synthesis of Highly Substituted Polycyclic Aromatic and Heteroaromatic Compounds", *J. Org. Chem.*, 1990, 112, 8 pages.
De Lucca et al. "Discovery and Structure-Activity Relationship of N-(Ureidoalkyl)-Benzyl-Piperidines as Potent Small Molecule CC Chemokine Receptor-3 (CCR3) Antagonists", *J. Med. Chem.*, 2002, 45, 3794-3804.
Edwards et al. "Application of Fragment-Based Lead Generation to the Discovery of Novel, Cyclic Amidine β-Secretase Inhibitors with Nanomolar Potency, Cellular Activity, and High Ligand Efficiency", *J. Med. Chem.*, 2007, 50, 5912-5925.
Fang et al. "Synthesis, Antibacterial, and Cytotoxic Evaluation of Certain 7-Substituted Norfloxacin Derivatives", *J. Med. Chem.*, 2000, 43, 3809-3812.
Fuller et al. "Succinct Synthesis of β-Amino Acids via Chiral Isoxazolines", *J. Am. Chem. Soc.*, 2005, 127, 5376-5383.
Fuller et al. "Synthesis and Structural Characteristics of Geminally Disubstituted β-Amino Acids", *Synlett.*, 2004, No. 8, 1409-1413.
Fulop et al. "Synthesis of Stereoisomeric 2-Phenylimino-3,1-Perhydrobenzoxazines and 3,1-Perhydrobenzothiazines", *Organic Preparations and Procedures Int.*, 20(1), 73-82, 1988.
Greene et al., Protective Groups in Organic Synthesis, Third Edition, 1999, Protection for the Hydroxyl Group, Including 1,2- and 1,3-Diols, pp. 17-245.
Greene et al., Protective Groups in Organic Synthesis, Third Edition, 1999, Protection for the Carbonyl Group, pp. 293-329.
Greene et al., Protective Groups in Organic Synthesis, Third Edition, 1999, Protection for the Amino Group, pp. 494-572.
Greene et al., Protective Groups in Organic Synthesis, Third Edition, 1999, Protection for the Amino Group, pp. 506-507.
Greene et al., Protective Groups in Organic Synthesis, Third Edition, 1999, Protection for the Amino Group, pp. 531-537.
Greene et al., Protective Groups in Organic Synthesis, Third Edition, 1999, Protection for the Amino Group, pp. 642-643.
Greene et al., Protective Groups in Organic Synthesis, Third Edition, 1999, Protection for the Amino Group, pp. 327-330.
Gu et al. "Facile One-Pot Synthesis of 6-Monosubstituted and 6,12-Disubstituted 5, 11-Dihydroindolo[3,2-b]carbazoles and Preparation of Various Functionalized Derivatives", *J. Org. Chem.*, 2007, 72, 7207-7213.
Hall et al. Comparitive pharmacokinetic-pharmacodynamic responses in rat and cynomolgus monkey for a novel BACE inhibitor ER-901356, The 11th International Conference on Alzheimer's & Parkinson's Disease, AD/PD, 2013, Poster Session 2, Mar. 8, 2013, Mechanisms, clinical strategies, and promising treatments of neurodegenerative diseases, Florence, Italy, Mar. 6-10, 2013, 4 pages.
Han et al. "Diverse Synthesis of Novel Bisterpyridines via Suzuki-Type Cross-Coupling", *Organic Letters*, 2007, vol. 9, No. 4, 559-562.
Hassner et al. "Intramolecular Oxime Olefin Cycloadditions. Stereospecific Formation of Functionalized Pyrrolidines", *Tetrahedron Letters*, vol. 29, No. 41, pp. 5313-5316, 1988.

(56) References Cited

OTHER PUBLICATIONS

Hassner et al. "On the conformation of Fused Five-Membered Heterocyclic Rings Derived from the Intramolecular Oxime Olefin Cycloaddition Reaction", *J. Org. Chem.*, 1993, 58, 4539-4546.

Iwata et al. "Radiosynthesis of O-[$^{11}$C]methyl-L-tyrosine and O-[$^{18}$F]Fluoromethyl-L-tyrosine as potential PET tracers for imaging amino acid transport", *Journal of Labelled Compounds and Radiopharmaceuticals*, 2003, 46, 555-566.

Ji et al. "Synthesis and Structure-Activity Relationship Studies of 3,6-Diazabicyclo[3.2.0]heptanes as Novel α4β2 Nicotinic Acetylcholine Receptor Selective Agonists", *J. Med. Chem.*, 2007, 50, 5493-5508.

Kearney et al. "Solid-Phase Synthesis of 2-Aminothiazoles", *J. Org. Chem.*, 1998, 63-196-200.

Knauer et al. "Palladium-catalysed C—C coupling reactions in the enantioselective synthesis of 2, 4-disubstituted 4,5-dehydropiperidines using galactosylamine as a sterodifferentiating auxiliary", *Tetrahedron: Asymmetry*, 16, 2005, 52-539.

Kwong et al. "Copper-Catalyzed Coupling of Alkylamines and Aryl Iodides: An Efficient System Even in an Air Atmosphere", *Organic Letters*, 2002, vol. 4, No. 4, 581-584.

Leroux et al. "Trifluoromethoxy Substituted Anilines: Metalation as the Key Step for Structural Elaboration", *J. Org. Chem.*, 2003, 68, 4693-4699.

Littke et al. "Versatile Catalysts for the Suzuki Cross-Coupling of Arylboronic Acids with Aryl and Vinyl Halides and Triflates under Mild Conditions", *J. Am. Chem. Soc.*, 2000, 122, 4020-4028.

Matassa et al. "Synthesis and in Vitro LTD$_4$ Antagonist Activity of Bicyclic and Monocyclic Cyclopentylurethane and Cyclopentylacetamide N-Arylsulfonyl Amides", *J. Med. Chem.*, 1990, 9 pages.

Nerdinger et al. "Combined Directed *ortho* Metalation/Suzuki-Miyaura Cross-Coupling Strategies, Regiospecific Synthesis of Chlorodihydroxybiphenyls and Polychlorinated Biphenyls", *J. Org. Chem.*, 2007, 72, 5960-5967.

Nussbaumer et al. "Highly Selective TFAA-Cleavage of Tertiary 2,4-Dimethoxybenzylamines and Its Use in the Synthesis of Secondary Amines", *Tetrahedron*, vol. 47, No. 26, 4591-4602, 1991.

Quach et al. "Ligand- and Base-Free Copper (II)-Catalyzed C—N Bond Formation: Cross-Coupling Reactions of Organoboron Compounds with Aliphatic Amines and Anilines", *Organic Letters*, 2003, vol. 5, No. 23, 4397-4400.

Rao et al. "Improved Synthesis of Mirtazapine", *OPPI Briefs*, vol. 39, No. 4, 2007, 399-402.

Rolandsgard et al. "Stereoselective preparation of spirane bridged, sandwiched bisarenes", *Tetrahedron*, 61, (2005), 4129-4140.

Sapountzis et al. "Synthesis of Functionalized Nitroarylmagnesium Halides via an Iodine—Magnesium Exchange", *J. Org. Chem.*, 2005, 70, 2445-2454.

Schwizer et al. "Antagonists of the myelin-associated glycoprotein: A new class of tetrasaccharide mimics", *Bioorganic & Medicinal Chemistry*, 14, 2006, 4944-4957.

Selles et al. "Expedient Synthesis of Highly Substituted Fused Heterocoumarins", *Organic Letters*, 2004, vol. 6, No. 2, 277-279.

Shao et al. "4-(2-Pyridyl)piperazine-1-benzimidazoles as potent TRPV1 antagonists", *Bioorganic & Medicinal Chemistry Letters*, 15, 2005, 719-723.

Tamayo et al. "Design and synthesis of potent pyridazine inhibitors of p38 MAP kinase", *Bioorganic & Medicinal Chemistry Letters*, 15, 2005, 2409-2413.

Tao et al. "Copper-catalyzed synthesis of aryl azides and 1-aryl-1,2,3-triazoles from boronic acids", *Tetrahedron Letters*, 48, 2007, 3525-3529.

Tzschucke et al. "Arenes to Anilines and Aryl Ethers by Sequential Iridium-Catalyzed Borylation and Copper-Catalyzed Coupling", *Organic Letters*, 2007, vol. 9, No. 5, 761-764.

Vedejs et al. "Enantiocontrolled Synthesis of (1S,2S)-6-Desmethyl-(methylaziridino)mitosene", *J. Am. Chem. Soc.* 2000, 122, 5401-5402.

Vedejs et al. "Synthetic Enantiopure Aziridinomitosenes: Preparation, Reactivity, and DNA Alkylation Studies", *J. Am. Chem. Soc.*, 2003, 125, 15796-15806.

Watanabe et al. "A Convenient Method for the Synthesis of $\Delta^{1-6}$-Bicyclo[4.n.0]alken-2-ones", *Tetrahedron Letters*, 40, 1999, 8133-8136.

Notice of Allowance, U.S. Appl. No. 13/685,109, mailed May 31, 2013.

* cited by examiner

METHODS AND COMPOUNDS USEFUL IN THE SYNTHESIS OF FUSED AMINODIHYDROTHIAZINE DERIVATIVES

RELATED APPLICATIONS

This application is a divisional of U.S. patent application Ser. No. 13/795,308, filed Mar. 12, 2013, which is a divisional of U.S. patent application Ser. No. 13/355,030, filed Jan. 20, 2012, now Pat. No. 8,426,584, and claims the benefit under 35 U.S.C. §119(e) of U.S. Provisional Patent Application No. 61/434,849, filed Jan. 21, 2011, the disclosure of each of which is incorporated by reference herein in its entirety.

FIELD OF THE INVENTION

The present invention relates to compounds and methods that are useful for the preparation of compounds useful as inhibitors of beta-site amyloid precursor protein (APP)-cleaving enzyme.

BACKGROUND OF THE INVENTION

Alzheimer's disease is a disease characterized by degeneration and loss of neurons as well as formation of senile plaques and neurofibrillary degeneration. Currently, Alzheimer's disease is treated only with symptomatic treatment using a symptom improving agent typified by an acetylcholinesterase inhibitor, and a fundamental remedy to inhibit progression of the disease has not yet been developed. It is necessary to develop a method for controlling the cause of the onset of pathology in order to create a fundamental remedy for Alzheimer's disease.

It is thought that Aβ-proteins as break-down products of amyloid precursor proteins (APP) are involved in the degeneration and loss of neurons and onset of symptoms of dementia (see, e.g., Klein et al., Alzheimer's disease-affected brain: Presence of oligomeric Aβ ligands (ADDLs) suggests a molecular basis for reversible memory loss, PNAS USA 2003, Sep. 2; 100 (18), p. 10417-10422; Nitsch et al., Antibodies against β-amyloid slow cognitive decline in Alzheimer's disease, Neuron, 2003, May 22; 38, p. 547-554).

Aβ-proteins have, as main components, Aβ40 consisting of 40 amino acids and Aβ42 with two amino acids added at the C-terminal. The Aβ40 and Aβ42 are known to have high aggregability and to be main components of senile plaques (see, e.g., Jarrett et al., The carboxy terminus of the β amyloid protein is critical for the seeding of amyloid formation: Implications for the pathogenesis of Alzheimers' disease, Biochemistry, 1993, 32 (18), p. 4693-4697; Glenner et al., Alzheimer's disease: initial report of the purification and characterization of a novel cerebrovascular amyloid protein, Biochemical and biophysical research communications, 1984, May 16, 120 (3), p. 885-890; Masters et al., Amyloid plaque core protein in Alzheimer disease and Down syndrome, PNAS USA, 1985, June, 82 (12), p. 4245-4249). Further, it is known that the Aβ40 and Aβ42 are increased by mutation in APP and presenilin genes which is observed in familial Alzheimer's disease (see, e.g., Gouras et al., Intraneuronal Aβ42 accumulation in human brain, American Journal of Pathology, 2000, January, 156 (1), p. 15-20; Scheuner et al., Secreted amyloid β-protein similar to that in the senile plaques of Alzheimer's disease is increased in vivo by the presenilin 1 and 2 and APP mutations linked to familial Alzheimer's disease, Nature Medicine, 1996, August, 2 (8), p. 864-870; Forman et al., Differential effects of the swedish mutant amyloid precursor protein on β-amyloid accumulation and secretion in neurons and nonneuronal cells, The Journal of Biological Chemistry, 1997, Dec. 19, 272 (51), p. 32247-32253). Accordingly, a compound that reduces production of Aβ40 and Aβ42 is expected to be a progression inhibitor or prophylactic agent for Alzheimer's disease.

Aβ is produced by cleaving APP by beta-secretase (BACE1) and subsequently by gamma-secretase. For this reason, attempts have been made to create gamma-secretase and beta-secretase inhibitors in order to inhibit Aβ production.

SUMMARY

The present invention relates to compounds and methods that are useful for the preparation of inhibitors of beta-site amyloid precursor protein (APP)-cleaving enzyme, also known as beta-secretase, or BACE1. BACE1 inhibitor compounds and methods of making the same have been described, for example, in WO 2009/091016, the contents of which is hereby incorporated by reference herein in its entirety.

Provided herein are compounds of Formula I:

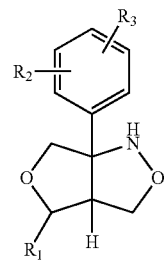

I wherein:
R$_1$ is alkyl, haloalkyl, hydroxyalkyl, or —(C$_{1-6}$alkyl)-OR', wherein R' is an oxygen protecting group; and
R$_2$ and R$_3$ are each independently hydrogen or halo (e.g., fluoro);
or a salt thereof.

In some embodiments, Formula I is subject to the proviso that when one of R2 or R3 is ortho-fluoro, and the other is hydrogen, R$_1$ is not —CH$_2$F.

In some embodiments, R$_1$ is trifluoromethyl, hydroxymethyl, monofluoromethyl, or triphenylmethoxymethyl.

In some embodiments, R$_2$ is fluoro, and/or R$_3$ is hydrogen or fluoro.

Also provided are methods of making a compound of Formula I as defined above. In some embodiments, the method includes the step of heating a mixture including:
(i) an oxime of Formula A:

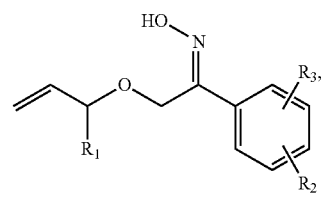

A wherein R$_1$, R$_2$ and R$_3$ are as given above for Formula I;
(ii) hydroquinone; and (iii) a hydrocarbon solvent (e.g., benzene, toluene, xylenes, etc.), to a temperature of from 90, 95, 100, 105, or 110° C., to 115, 120, 125, 130, 135, 140, 145, 150, 155, or 160° C. (for example, from 90° C. to 160° C., or from 110° C. to 140° C., or from 100° C. to 120° C., or from 120° C. to 140° C.), to make said compound of Formula I, or a salt thereof.

In some embodiments, the method includes the step of heating a mixture comprising:

(i) a compound of Formula B:

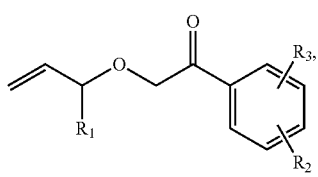

wherein $R_1$, $R_2$ and $R_3$ are as given above;

(ii) an acetate;

(iii) hydroxylamine or a salt thereof; and (iv) a hydrocarbon solvent (e.g., benzene, toluene, xylenes, etc.), to a temperature of from 90, 95, 100, 105, or 110° C., to 115, 120, 125, 130, 135, 140, 145, 150, 155, or 160° C. (for example, from 90° C. to 160° C., or from 110° C. to 140° C., or from 100° C. to 120° C., or from 120° C. to 140° C.), to make said compound of Formula I, or a salt thereof.

Further provided are compounds of Formula II:

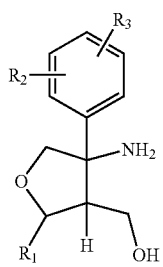

wherein:

$R_1$ is alkyl, haloalkyl, hydroxyalkyl, or —($C_{1-6}$)—OR', wherein R' is an oxygen protecting group; and $R_2$ and $R_3$ are each independently hydrogen or halo (e.g., fluoro);

or a salt thereof.

In some embodiments, Formula II is subject to the proviso that when one of R2 or R3 is ortho-fluoro, and the other is hydrogen, $R_1$ is not —$CH_2F$.

In some embodiments, $R_1$ is trifluoromethyl, hydroxymethyl, monofluoromethyl, or triphenylmethoxymethyl, In some embodiments, $R_2$ is fluoro, and/or $R_3$ is hydrogen or fluoro.

Also provided are methods of making a compound of Formula II:

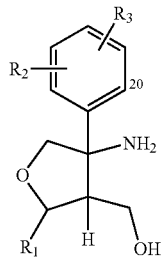

wherein:

$R_1$ is $C_{1-4}$alkyl; and $R_2$ and $R_3$ are each independently hydrogen or halo;

or a salt thereof, comprising the steps of:

(a) heating a mixture comprising:

(i) a ketone of Formula B:

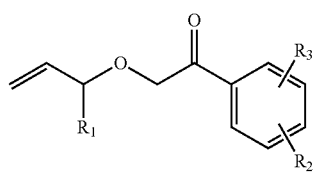

wherein $R_1$, $R_2$ and $R_3$ are as given above for Formula II;

(ii) hydroxylamine or a salt thereof;

(iii) a base (e.g., acetate, propionate, a tertiary amine base such as triethylamine or diethylisopropylamine, pyridine, or a salt thereof); and (iv) a solvent selected from: water and an alcohol (e.g., a $C_{3-8}$ alcohol), to at least 90 or 100° Celsius (e.g., to boiling such as by refluxing) produce a heated mixture, (b) cooling the heated mixture to a temperature of at or below 60, 50 or 45° Celsius, and then, (c) adding an organic solvent (e.g., tetrahydrofuran or an ether solvent such as diethyl ether or methyl tert-butyl ether), an acid (e.g., a carboxylic acid such as acetic acid, or a mineral acid such as hydrochloric acid or sulfuric acid), and zinc (e.g., zinc powder or zinc dust) to the mixture, wherein said mixture is maintained at or below 60, 50 or 45 degrees Celsius (e.g., between 25, 30 or 35, and 45, 50 or 60 degrees Celsius) during said adding, to make said compound of Formula II.

In some embodiments, the heating is carried out for at least 30 hours.

Also provided is a method of making a stereochemically pure compound of Formula IIa:

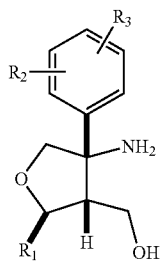

wherein $R_1$, $R_2$ and $R_3$ are as given above for Formula II, or a salt thereof, including the steps of:

(a) adding a mixture of stereoisomers of the compound of Formula II:

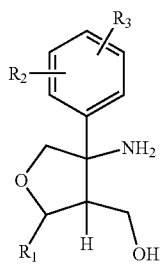

wherein $R_1$, $R_2$ and $R_3$ are as given above, to a solvent (e.g., an alcohol such as ethanol or isopropanol, or a mixture such as a toluene—acetonitrile mixture, a toluene—acetone mixture, a toluene—tetrahydrofuran mixture, or an alcohol—water mixture), which solvent includes a chiral carboxylic acid compound (e.g., D-dibenzoyl tartaric acid, L-dibenzoyl tartaric acid, D-ditoluyl tartaric acid, and L-ditoluyl tartaric acid, etc.) to form a mixture of diastereomeric salts of the compound of Formula II; and then (b) crystallizing a single diastereomeric salt formed of the compound of Formula II, to make the stereochemically pure compound of Formula IIa, or a salt thereof.

In some embodiments, the stereochemically pure compound has greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound greater than about 90% by weight of one stereoisomer of the compound and less than about 10% by weight of the other stereoisomers of the compound.

In some embodiments, the crystallizing step is performed by cooling the mixture of diastereomeric salts of the compound of Formula II (e.g., to a temperature of from 40, 45, 50, 55, or 60° C. to 80, 90, 100, or 110° C., to a temperature of from −10, −5, 0, 5, or 10° C. to 15, 20, 29, or 35° C.).

Further provided are compounds of Formula III:

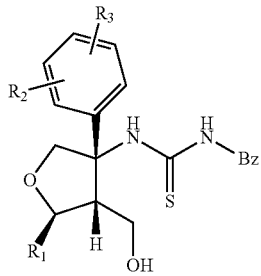

wherein:

$R_1$ is alkyl, haloalkyl, hydroxyalkyl, or —$(C_{1-6})$—OR', wherein R' is an oxygen protecting group; and $R_2$ and $R_3$ are each independently hydrogen or halo (e.g., fluoro);

or a salt thereof.

In some embodiments, Formula III is subject to the proviso that when one of R2 or R3 is ortho-fluoro, and the other is hydrogen, $R_1$ is not —$CH_2F$.

In some embodiments, $R_1$ is trifluoromethyl, hydroxymethyl, monofluoromethyl, or triphenylmethoxymethyl.

In some embodiments, $R_2$ is fluoro, and/or $R_3$ is hydrogen or fluoro.

Also provided are compounds of Formula IV:

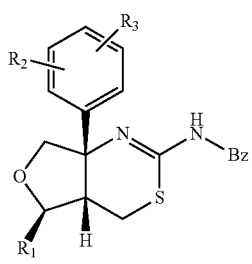

wherein:

$R_1$ is alkyl, haloalkyl, hydroxyalkyl, or —$(C_{1-6})$—OR', wherein R' is an oxygen protecting group; and $R_2$ and $R_3$ are each independently hydrogen or halo (e.g., fluoro);

or a salt thereof.

In some embodiments, Formula IV is subject to the proviso that when one of R2 or R3 is ortho-fluoro, and the other is hydrogen, $R_1$ is not —$CH_2F$.

In some embodiments, $R_1$ is trifluoromethyl, hydroxymethyl, monofluoromethyl, or triphenylmethoxymethyl.

In some embodiments, $R_2$ is fluoro, and/or $R_3$ is hydrogen or fluoro.

Further provided are compounds of Formula V:

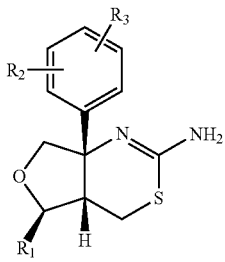

wherein:

R$_1$ is alkyl, haloalkyl, hydroxyalkyl, or —(C$_{1-6}$)—OR', wherein R' is an oxygen protecting group; and R$_2$ and R$_3$ are each independently hydrogen or halo (e.g., fluoro);

or a salt thereof.

In some embodiments, Formula V is subject to the proviso that when one of R2 or R3 is ortho-fluoro, and the other is hydrogen, R$_1$ is not —CH$_2$F.

In some embodiments, R$_1$ is trifluoromethyl, hydroxymethyl, monofluoromethyl, or triphenylmethoxymethyl.

In some embodiments, R$_2$ is fluoro, and/or R$_3$ is hydrogen or fluoro.

Also provided are methods for making a compound of Formula V:

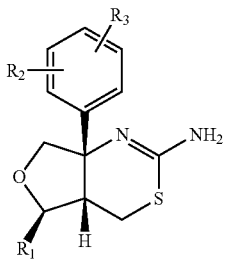

wherein:

R$_1$ is C$_{3-4}$alkyl, halo-C$_{1-4}$alkyl, hydroxy-C$_{1-4}$alkyl, or —C$_{1-4}$alkyl-OR', wherein R' is an oxygen protecting group; and R$_2$ and R$_3$ are each independently hydrogen or halo; or a salt thereof, comprising the steps of:
(a) providing a mixture of
  (i) a compound of Formula III,

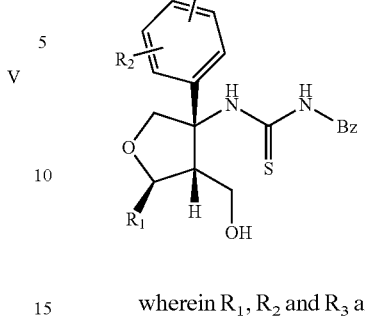

wherein R$_1$, R$_2$ and R$_3$ are as given above for Formula V;
  (ii) an amine base (e.g., pyridine, or a substituted pyridine such as collidine); and
  (iii) an organic solvent (e.g., an aromatic hydrocarbon solvent, toluene, xylenes, benzene, dichloromethane, etc.),
  wherein said mixture is at a temperature at or below 0° Celsius,
(b) reacting the mixture with trifluoromethanesulfonic anhydride, 4-toluenesulfonyl chloride, methanesulfonyl chloride or methanesulfonyl anhydride, and then,
(c) adding:
  (i) an alcohol (e.g., propanol, such as 2-propanol); and
  (ii) a base, such as a strong base selected from: a hydroxide, an alkoxide, and ammonia,
to make said compound of Formula V.

In some embodiments, the reacting step is carried out at a temperature of from −15, −10, or −5, to 0° Celsius.

Also provided are compound of Formula VI:

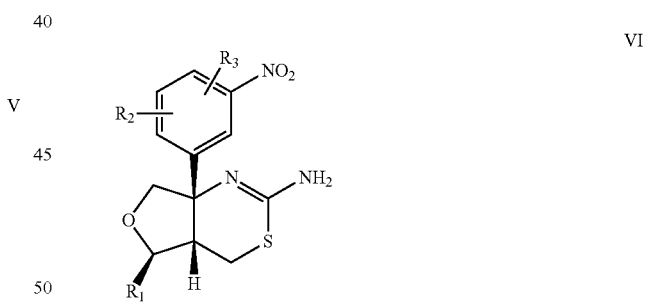

wherein:

R$_1$ is alkyl, haloalkyl, hydroxyalkyl, or —(C$_{1-6}$)—OR', wherein R' is an oxygen protecting group; and R$_2$ and R$_3$ are each independently hydrogen or halo (e.g., fluoro);

or a salt thereof.

In some embodiments, Formula VI is subject to the proviso that when one of R2 or R3 is ortho-fluoro, and the other is hydrogen, R$_1$ is not —CH$_2$F.

In some embodiments, R$_1$ is trifluoromethyl, hydroxymethyl, monofluoromethyl, or triphenylmethoxymethyl.

In some embodiments, R$_2$ is fluoro, and/or R$_3$ is hydrogen or fluoro.

Further provided are compounds of Formula VII:

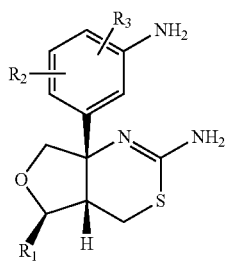

VII wherein:
R$_1$ is alkyl, haloalkyl, hydroxyalkyl, or —(C$_{1-6}$)—OR', wherein R' is an oxygen protecting group; and
R$_2$ and R$_3$ are each independently hydrogen or halo (e.g., fluoro);
or a salt thereof.

In some embodiments, R$_1$ is methyl, trifluoromethyl, hydroxymethyl, monofluoromethyl, or triphenylmethoxymethyl.

In some embodiments, R$_2$ is fluoro, and/or R$_3$ is hydrogen or fluoro.

Also provided are methods of making a compound of Formula VII, or a salt thereof, including the step of:
reducing a compound of Formula VI to form a compound of Formula VII, as shown below:

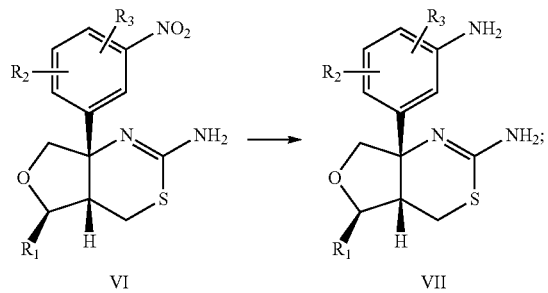

VI                              VII wherein:
R$_1$ is alkyl, haloalkyl, hydroxyalkyl, or —(C$_{1-6}$)—OR', wherein R' is an oxygen protecting group; and
R$_2$ and R$_3$ are each independently hydrogen or halo.

In some embodiments, R$_1$ is trifluoromethyl, hydroxymethyl, monofluoromethyl, or triphenylmethoxymethyl.

In some embodiments, R$_2$ is fluoro, and/or R$_3$ is hydrogen or fluoro.

In some embodiments, the reducing of the compound of Formula VI to form the compound of Formula VII may include one or more of the steps of: (a) adding powdered iron to a carbinol solvent to form a mixture thereof; (b) adding hydrochloric acid (HCl) (e.g., concentrated HCl) to the mixture of step (a); (c) heating the mixture of step (b) to a temperature of from 31, 40 or 50° C. to 65, 70, 75, 80, 85° C., or to the boiling point of the mixture of step (b) (e.g., for 0-4 hours) to form a heated mixture; and (d) adding the compound of Formula VI, or a salt thereof, to the heated mixture of step (c).

In some embodiments, the method further includes the steps of: (e) cooling the mixture of step (d) to a temperature of between 10 and 30° C. to form a cooled mixture; and (f) optionally, stirring the cooled mixture (e.g., for 0-4 hours).

In some embodiments, the HCl is provided in an amount selected from the group consisting of: an amount of HCl stoichiometric with respect to the amount of the compound of Formula VI; and an amount of HCl in molar excess with respect to the amount of the compound of Formula VI.

Further provided are methods of making a compound of Formula IX:

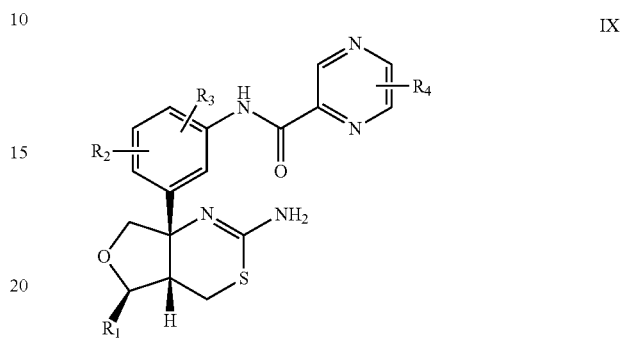

IX wherein:
R$_1$ is alkyl, haloalkyl, hydroxyalkyl, or —(C$_{1-6}$)—OR', wherein R' is an oxygen protecting group; and
R$_2$ and R$_3$ are each independently hydrogen or halogen; and
R$_4$ is selected from the group consisting of alkyl, haloalkyl, alkoxy, and alkyl substituted with alkoxy;
or a salt thereof;
including the step of reacting a compound Formula VII with a pyrazine carboxylic acid of Formula VIII:

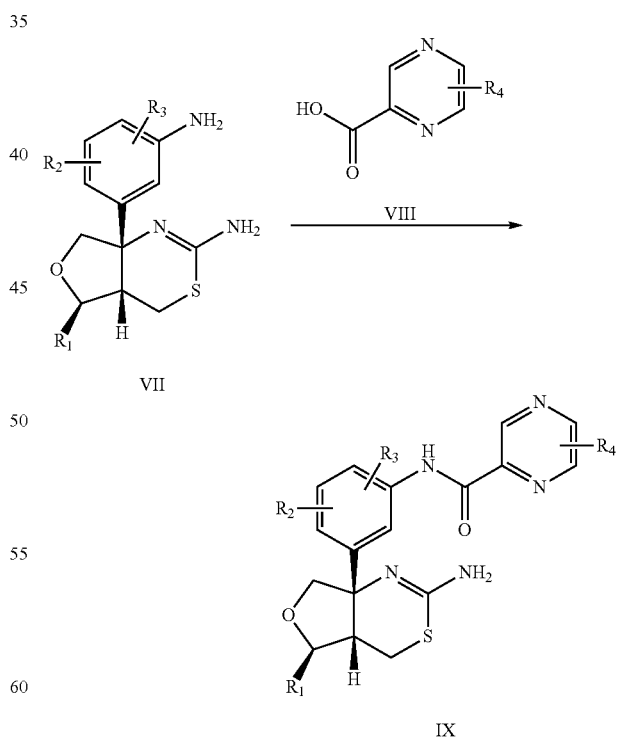

wherein R$_1$, R$_2$, R$_3$ and R$_4$ are as given above, to form said compound of Formula IX, or a salt thereof.

In some embodiments, the reacting may include one or more of the steps of: (a) adding thionyl chloride to a solution comprising a compound of Formula VIII in a solvent to make a formed mixture; and (b) adding a compound of Formula VII to the formed mixture of step (a), to form said compound of Formula IX, or a salt thereof.

In some embodiments, the solution comprising the compound of Formula VIII is a solvent is cooled prior to or during the adding step (a) (e.g., to a temperature of from 0 to 25° C.).

In some embodiments, the solvent may include N,N'-dimethylimidazoline-2-one, toluene, methylene chloride, dimethylformamide, N-methylpyrrolidine, or dimethyacetamide.

In some embodiments, the reacting may include one or more of the steps of: (a) adding ethyl acetate (EtOAc) to a compound of Formula VIII and a compound of Formula VII to make a formed mixture; and (b) adding an alkyl phosphonic acid anhydride (e.g., 2-propyl phosphonic acid anhydride) to the formed mixture of step (a), to form said compound of Formula IX, or a salt thereof.

In some embodiments, the formed mixture may be maintained at a temperature of from 0° C. to 35° C. during said adding step (a).

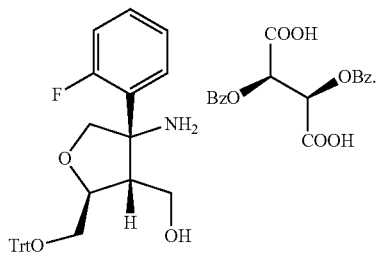

DETAILED DESCRIPTION

A. Definitions

Figure 1A:
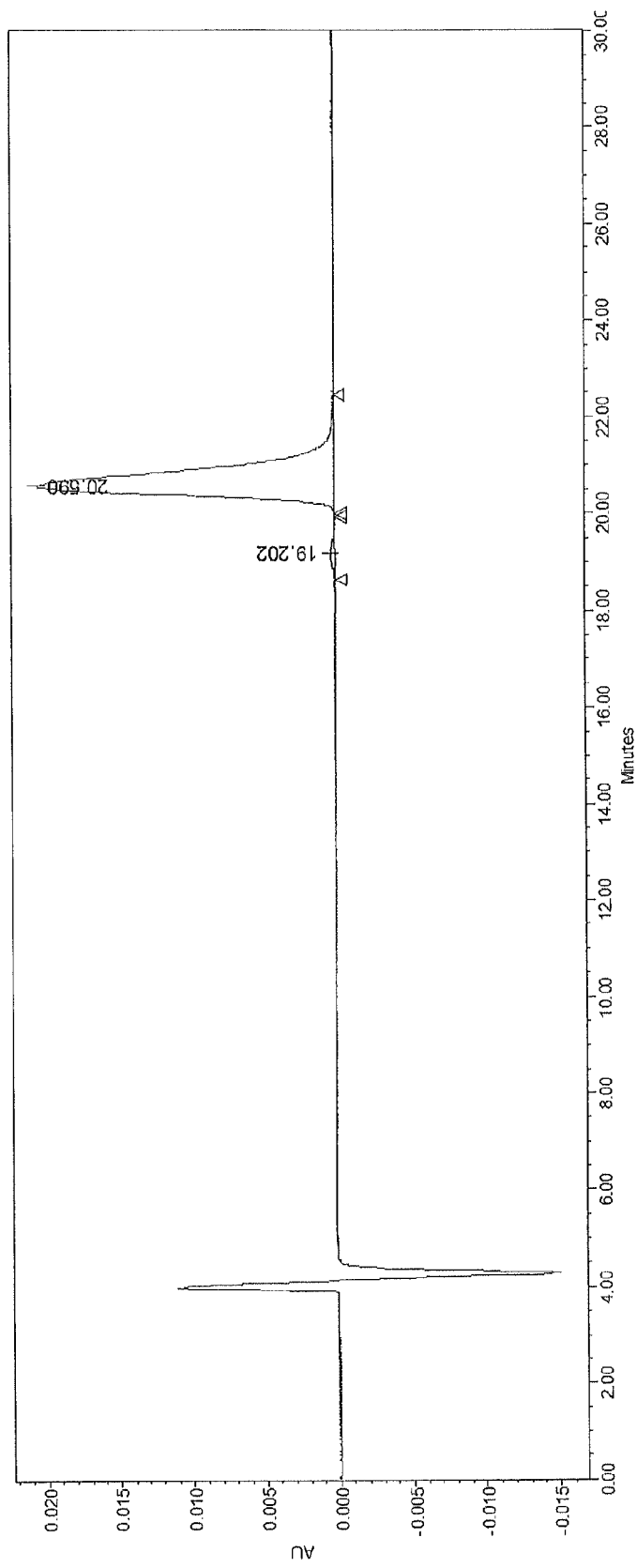
FIGS. 1A-1B present typical chromatograms from chiral HPLC upon diastereomeric resolution of a tetrahydrofuran of Formula II in accordance with Example 4, part C.

Compounds of this invention include those described generally above, and are further illustrated by the embodiments, sub-embodiments, and species disclosed herein. As used herein, the following definitions shall apply unless otherwise indicated.

As described herein, compounds of the invention may optionally be substituted with one or more substituents, such as are illustrated generally above, or as exemplified by particular classes, subclasses, and species of the invention. In general, the term "substituted" refers to the replacement of hydrogen in a given structure with a specified substituent. Unless otherwise indicated, a substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

"Isomers" refer to compounds having the same number and kind of atoms and hence the same molecular weight, but differing with respect to the arrangement or configuration of the atoms.

"Stereoisomers" refer to isomers that differ only in the arrangement of the atoms in space.

"Diastereoisomers" refer to stereoisomers that are not mirror images of each other.

"Enantiomers" refers to stereoisomers that are non-superimposable mirror images of one another.

Enantiomers include "enantiomerically pure" isomers that comprise substantially a single enantiomer, for example, greater than or equal to 90%, 92%, 95%, 98%, or 99%, or equal to 100% of a single enantiomer.

"Enantiomerically pure" as used herein means a compound, or composition of a compound, that comprises substantially a single enantiomer, for example, greater than or equal to 90%, 92%, 95%, 98%, or 99%, or equal to 100% of a single enantiomer.

"Stereomerically pure" as used herein means a compound or composition thereof that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of diastereomers, and substantially free of the enantiomer, of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound. See, e.g., U.S. Pat. No. 7,189,715.

"R" and "S" as terms describing isomers are descriptors of the stereochemical configuration at an asymmetrically substituted carbon atom. The designation of an asymmetrically substituted carbon atom as "R" or "S" is done by application of the Cahn-Ingold-Prelog priority rules, as are well known to those skilled in the art, and described in the International Union of Pure and Applied Chemistry (IUPAC.) Rules for the Nomenclature of Organic Chemistry. Section E, Stereochemistry.

"Enantiomeric excess" (ee) of an enantiomer is [(the mole fraction of the major enantiomer) minus (the mole fraction of the minor enantiomer)]×100.

"Stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

"Refluxing" as used herein refers to a technique in which vapors from a boiling liquid are condensed and returned to the mixture from which it came, typically by boiling the liquid in a vessel attached to a condenser.

"Powdered iron" or "iron powder" is iron having an average particle size of less than 0.1, 0.5, 1, 5, 10, 20, 50, 250, 500 or 1000 Particle size can be measured using methods known in the art, e.g., mesh sizing, laser diffraction, etc.

"Zinc dust" is zinc having an average particle size of less than 0.001, 0.05, 0.1, 0.5, 1, 5, 10, 15 or 20 µm, "Zinc powder" is zinc having an average particle size of less than 200, 175, 150, 125, or 100 µm. Particle size can be measured using methods known in the art, e.g., mesh sizing, laser diffraction, etc.

An "organic" compound as used herein is a compound that contains carbon. Similarly, an "organic solvent" is a compound containing carbon that is useful as a solvent. An "inorganic" compound is a compound not containing carbon.

"Mineral acid" as used herein is the acid of an inorganic compound. Examples include, but are not limited to, hydrochloric acid (HCl), nitric acid ($HNO_3$), phosphoric acid ($H_3PO_4$), sulfuric acid ($H_2SO_4$), boric acid ($B(OH)_3$), hydrofluoric acid (HF), hydrobromic acid (HBr), perchoric acid ($HClO_4$), etc.

A "hydrocarbon" is an organic compound consisting of carbon and hydrogen atoms. Examples of hydrocarbons useful as "hydrocarbon solvents" include, but are not limited to, an "aromatic hydrocarbon solvent" such as benzene, toluene, xylenes, etc., and an "aliphatic hydrocarbon solvent" such as pentane, hexane, heptane, etc.

An "amine" or "amine base" as used herein refers to an organic compound having a basic nitrogen atom (R—NR'R"), and may be a primary (R—$NH_2$), secondary (R—NHR') or tertiary (R—NR'R") amine.

A "strong base" as used herein is a compound that is capable of deprotonating very weak acids. Examples of strong bases include, but are not limited to, hydroxides, alkoxides, and ammonia.

A "hydroxide" is the commonly known diatomic anion OH", or a salt thereof (typically an alkali metal or alkaline earth metal salt thereof). Examples of hydroxides include, but are not limited to, sodium hydroxide (NaCl), potassium hydroxide (KOH), lithium hydroxide (LiOH), and calcium hydroxide (CaOH).

An "alkoxide" is $RO^-$, the conjugate base of an alcohol. Examples include, but are not limited to, methoxide, ethoxide, and propoxide.

"Ar" or "aryl" refer to an aromatic carbocyclic moiety having one or more closed rings. Examples include, without limitation, phenyl, naphthyl, anthracenyl, phenanthracenyl, biphenyl, and pyrenyl.

"Heteroaryl" refers to a cyclic moiety having one or more closed rings, with one or more heteroatoms (for example, oxygen, nitrogen or sulfur) in at least one of the rings, wherein at least one of the rings is aromatic, and wherein the ring or rings may independently be fused, and/or bridged. Examples include without limitation quinolinyl, isoquinolinyl, indolyl, furyl, thienyl, pyrazolyl, quinoxalinyl, pyrrolyl, indazolyl, thieno[2,3-c]pyrazolyl, benzofuryl, pyrazolo[1,5-a]pyridyl, thiophenylpyrazolyl, benzothienyl, benzothiazolyl, thiazolyl, 2-phenylthiazolyl, and isoxazolyl.

"Alkyl" or "alkyl group," as used herein, means a straight-chain (i.e., unbranched), branched, or cyclic hydrocarbon chain that is completely saturated. In some embodiments, alkyl groups contain 1, 2, or 3, to 4, 5 or 6 carbon atoms (e.g., $C_{1-4}$, $C_{2-4}$, $C_{3-4}$, $C_1$-s, $C_{2-5}$, $C_{3-5}$, $C_{1-6}$, $C_{2-6}$, $C_{3-6}$). In some embodiments, alkyl groups contain 3-4 carbon atoms. In certain embodiments, alkyl groups contain 1-3 carbon atoms. In still other embodiments, alkyl groups contain 2-3 carbon atoms, and in yet other embodiments alkyl groups contain 1-2 carbon atoms. In certain embodiments, the term "alkyl" or "alkyl group" refers to a cycloalkyl group, also known as carbocycle. Non-limiting examples of exemplary alkyl groups include methyl, ethyl, propyl, isopropyl, butyl, cyclopropyl and cyclohexyl.

"Alkenyl" or "alkenyl group," as used herein, refers to a straight-chain (i.e., unbranched), branched, or cyclic hydrocarbon chain that has one or more double bonds. In certain embodiments, alkenyl groups contain 2-6 carbon atoms. In certain embodiments, alkenyl groups contain 2-4 carbon atoms. In still other embodiments, alkenyl groups contain 3-4 carbon atoms, and in yet other embodiments alkenyl groups contain 2-3 carbon atoms. According to another aspect, the term alkenyl refers to a straight chain hydrocarbon having two double bonds, also referred to as "diene." In other embodiments, the term "alkenyl" or "alkenyl group" refers to a cycloalkenyl group. Non-limiting examples of exemplary alkenyl groups include —CH═$CH_2$, —$CH_2$CH═$CH_2$ (also referred to as allyl), —CH═$CHCH_3$, —$CH_2CH_2$CH═$CH_2$, —$CH_2$CH═$CHCH_3$, —CH═$CH_2CH_2CH_3$, —CH═$CH_2$CH═$CH_2$, and cyclobutenyl.

"Alkoxy", or "alkylthio", as used herein, refers to an alkyl group, as previously defined, attached to the principal carbon chain through an oxygen ("alkoxy") or sulfur ("alkylthio") atom.

"Methylene", "ethylene", and "propylene" as used herein refer to the bivalent moieties —$CH_2$—, —$CH_2CH_2$—, and —$CH_2CH_2CH_2$—, respectively.

"Ethenylene", "propenylene", and "butenylene" as used herein refer to the bivalent moieties —CH═CH—, —CH—$CHCH_2$—, —$CH_2$CH═CH—, —CH═$CHCH_2CH_2$—, —$CH_2$CH═$CH_2CH_2$—, and —$CH_2CH_2$CH═CH—, where each ethenylene, propenylene, and butenylene group can be in the cis or trans configuration. In certain embodiments, an ethenylene, propenylene, or butenylene group can be in the trans configuration.

"Alkylidene" refers to a bivalent hydrocarbon group formed by mono or dialkyl substitution of methylene. In certain embodiments, an alkylidene group has 1-6 carbon atoms. In other embodiments, an alkylidene group has 2-6, 1-5, 2-4, or 1-3 carbon atoms. Such groups include propylidene ($cH_3CH_2$CH═), ethylidene ($CH_3$CH═), and isopropylidene ($CH_3(CH_3)$CH═), and the like.

"Alkenylidene" refers to a bivalent hydrocarbon group having one or more double bonds formed by mono or dialkenyl substitution of methylene. In certain embodiments, an alkenylidene group has 2-6 carbon atoms. In other embodiments, an alkenylidene group has 2-6, 2-5, 2-4, or 2-3 carbon atoms. According to one aspect, an alkenylidene has two double bonds. Exemplary alkenylidene groups include $CH_3$CH═C═, $CH_2$═CHCH═, $CH_2$═$CHCH_2$CH═, and $CH_2$═$CHCH_2$CH═CHCH═.

"$C_{1-6}$ alkyl ester or amide" refers to a $C_{1-6}$ alkyl ester or a $C_{1-6}$ alkyl amide where each $C_{1-6}$ alkyl group is as defined above. Such $C_{1-6}$ alkyl ester groups are of the formula ($C_{1-6}$ alkyl)OC(═O)— or ($C_{1-6}$ alkyl)C(═O)O—. Such $C_{1-6}$ alkyl amide groups are of the formula ($C_{1-6}$ alkyl)NHC(═O)— or ($C_{1-6}$ alkyl)C(═O)NH—.

"$C_{2-6}$ alkenyl ester or amide" refers to a $C_{2-6}$ alkenyl ester or a $C_{2-6}$ alkenyl amide where each $C_{2-6}$ alkenyl group is as defined above. Such $C_{2-6}$ alkenyl ester groups are of the formula ($C_{2-6}$ alkenyl)OC(═O)— or ($C_{2-6}$ alkenyl)C(═O)O—. Such $C_{2-6}$ alkenyl amide groups are of the formula ($C_{2-6}$ alkenyl)NHC(═O)— or ($C_{2-6}$ alkenyl)C(═O)NH—.

"Halo" refers to fluoro, chloro, bromo or iodo.

"Haloalkyl" refers to an alkyl group substituted with one or more halo atoms. For example, "fluoromethyl" refers to a methyl group substituted with one or more fluoro atoms (e.g., monofluoromethyl, difluoromethyl, trifluoromethyl).

"Hydroxyalkyl" refers to an alkyl group substituted with a hydroxyl group (—OH).

"Fluoromethoxy" as used herein, refers to a fluoromethyl group, as previously defined, attached to the principal carbon chain through an oxygen atom.

"Protecting group" as used herein, is meant that a particular functional moiety, e.g., 0, S, or N, is temporarily blocked so that a reaction can be carried out selectively at another reactive site in a multifunctional compound. For example, in certain embodiments, as detailed herein, certain exemplary oxygen protecting groups are utilized. Oxygen protecting groups include, but are not limited to, groups bonded to the oxygen to form an ether, such as methyl, substituted methyl (e.g., Trt (triphenylmethyl), MOM (methoxymethyl), MTM (methylthiomethyl), BOM (benzyloxymethyl), PMBM or MPM (p-methoxybenzyloxymethyl)), substituted ethyl (e.g., 2-(trimethylsilyl)ethyl), benzyl, substituted benzyl (e.g., para-methoxybenzyl), silyl (e.g., TMS (trimethylsilyl), TES (triethylsilyl), TIPS (triisopropylsilyl), TBDMS (t-butyldimethylsilyl), tribenzylsilyl, TBDPS (t-butyldiphenyl silyl), 2-trimethylsilylprop-2-enyl, t-butyl, tetrahydropyranyl, allyl, etc.

In some embodiments, the compounds may be provided as a salt, such as a pharmaceutically acceptable salt. Pharmaceutically acceptable salts are salts that retain the desired biological activity of the parent compound and do not impart undesired toxicological effects. Specific examples of pharmaceutically acceptable salts include inorganic acid salts (such as sulfates, nitrates, perchlorates, phosphates, carbonates, bicarbonates, hydrofluorides, hydrochlorides, hydrobromides and hydroiodides), organic carboxylates (such as acetates, oxalates, maleates, tartrates, fumarates and citrates), organic sulfonates (such as methanesulfonates, trifluoromethanesulfonates, ethanesulfonates, benzenesulfonates, toluenesulfonates and camphorsulfonates), amino acid salts (such as aspartates and glutamates), quaternary amine salts, alkali metal salts (such as sodium salts and potassium salts) and alkali earth metal salts (such as magnesium salts and calcium salts).

Unless indicated otherwise, nomenclature used to describe chemical groups or moieties as used herein follow the convention where, reading the name from left to right, the point of attachment to the rest of the molecule is at the right-hand side of the name. For example, the group "$(C_{1-3}$ alkoxy)$C_{1-3}$ alkyl," is attached to the rest of the molecule at the alkyl end. Further examples include methoxyethyl, where the point of attachment is at the ethyl end, and methylamino, where the point of attachment is at the amine end.

Unless indicated otherwise, where a mono or bivalent group is described by its chemical formula, including one or two terminal bond moieties indicated by "—," it will be understood that the attachment is read from left to right.

Unless otherwise stated, structures depicted herein are also meant to include all enantiomeric, diastereomeric, and geometric (or conformational) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention.

Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

B. Compounds and Chemical Synthesis

Provided herein are compounds of Formula I:

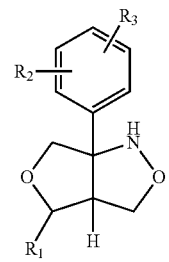

I wherein:

$R_1$ is alkyl, haloalkyl, hydroxyalkyl, or —($C_{1-6}$alkyl)-OR', wherein R' is an oxygen protecting group; and $R_2$ and $R_3$ are each independently hydrogen or halo (e.g., fluoro);

or a salt thereof.

In some embodiments, Formula I is subject to the proviso that when one of R2 or R3 is ortho-fluoro, and the other is hydrogen, $R_1$ is not —$CH_2F$.

In some embodiments, $R_1$ is trifluoromethyl, hydroxymethyl, monofluoromethyl, or triphenylmethoxymethyl.

In some embodiments, $R_2$ is fluoro, and/or $R_3$ is hydrogen or fluoro.

Examples of compounds of Formula I include:

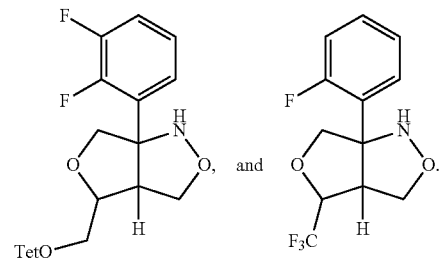

Also provided are methods of making a compound of Formula I as defined above. In some embodiments, the method includes the step of heating a mixture including:

(i) an oxime of Formula A:

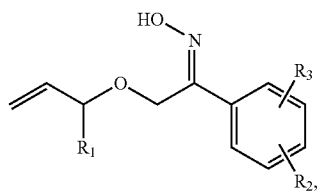

A wherein $R_1$, $R_2$ and $R_3$ are as given above for Formula I;

(ii) hydroquinone; and (iii) a hydrocarbon solvent (e.g., benzene, toluene, xylenes, etc.), to a temperature of from 90, 95, 100, 105, or 110° C., to 115, 120, 125, 130, 135, 140, 145, 150, 155, or 160° C. (for example, from 90° C. to 160° C., or from 110° C. to 140° C., or from 100° C. to 120° C., or from 120° C. to 140° C.), to make said compound of Formula I, or a salt thereof.

In some embodiments, the method includes the step of heating a mixture comprising:

(i) a compound of Formula B:

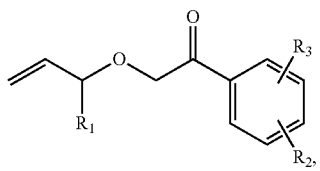

B wherein $R_1$, $R_2$ and $R_3$ are as given above;

(ii) an acetate;

(iii) hydroxylamine or a salt thereof; and (iv) a hydrocarbon solvent (e.g., benzene, toluene, xylenes, etc.), to a temperature of from 90, 95, 100, 105, or 110° C., to 115, 120, 125, 130, 135, 140, 145, 150, 155, or 160° C. (for example, from 90° C. to 160° C., or from 110° C. to 140° C., or from 100° C. to 120° C., or from 120° C. to 140° C.), to make said compound of Formula I, or a salt thereof.

Further provided are compounds of Formula II:

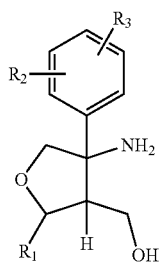

II wherein:

$R_1$ is alkyl, haloalkyl, hydroxyalkyl, or —($C_{1-6}$)—OR', wherein R' is an oxygen protecting group; and $R_2$ and $R_3$ are each independently hydrogen or halo (e.g., fluoro);

or a salt thereof.

In some embodiments, Formula II is subject to the proviso that when one of R2 or R3 is ortho-fluoro, and the other is hydrogen, $R_1$ is not —$CH_2F$.

In some embodiments, $R_1$ is trifluoromethyl, hydroxymethyl, monofluoromethyl, or triphenylmethoxymethyl.

In some embodiments, $R_2$ is fluoro, and/or $R_3$ is hydrogen or fluoro.

Examples of compounds of Formula II include:

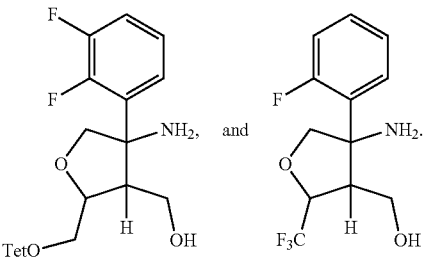

Also provided are methods of making a compound of Formula II:

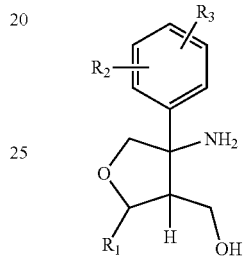

II wherein:

$R_1$ is $C_{1-4}$alkyl; and $R_2$ and $R_3$ are each independently hydrogen or halo;

or a salt thereof, comprising the steps of:

(a) heating a mixture comprising:

(i) a ketone of Formula B:

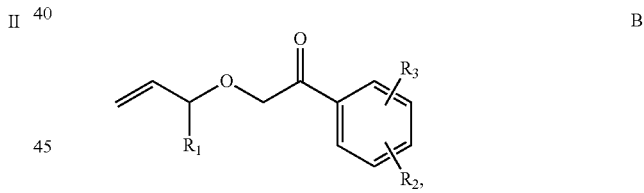

B wherein $R_1$, $R_2$ and $R_3$ are as given above for Formula II;

(ii) hydroxylamine or a salt thereof;

(iii) a base (e.g., acetate, propionate, a tertiary amine base such as triethylamine or diethylisopropylamine, pyridine, or a salt thereof); and (iv) a solvent selected from: water and an alcohol (e.g., a $C_{3-8}$ alcohol), to at least 90 or 100° Celsius (e.g., to boiling such as by refluxing) produce a heated mixture, (b) cooling the heated mixture to a temperature of at or below 60, 50 or 45° Celsius, and then, (c) adding an organic solvent (e.g., tetrahydrofuran or an ether solvent such as diethyl ether or methyl tert-butyl ether), an acid (e.g., a carboxylic acid such as acetic acid, or a mineral acid such as hydrochloric acid or sulfuric acid), and zinc (e.g., zinc powder or zinc dust) to the mixture, wherein said mixture is maintained at or below 60, 50 or 45 degrees Celsius (e.g., between 25, 30 or 35, and 45, 50 or 60 degrees Celsius) during said adding, to make said compound of Formula II.

In some embodiments, the heating is carried out for at least 30 hours.

Also provided is a method of making a stereochemically pure compound of Formula IIa:

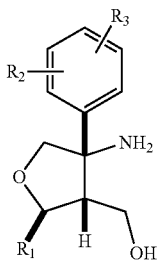

wherein $R_1$, $R_2$ and $R_3$ are as given above for Formula II, or a salt thereof,
including the steps of:

(a) adding a mixture of stereoisomers of the compound of Formula II:

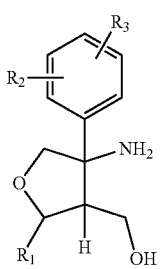

wherein $R_1$, $R_2$ and $R_3$ are as given above,
to a solvent (e.g., an alcohol such as ethanol or isopropanol, or a mixture such as a toluene—acetonitrile mixture, a toluene—acetone mixture, a toluene—tetrahydrofuran mixture, or an alcohol—water mixture), which solvent includes a chiral carboxylic acid compound (e.g., D-dibenzoyl tartaric acid, L-dibenzoyl tartaric acid, D-ditoluyl tartaric acid, and L-ditoluyl tartaric acid, etc.) to form a mixture of diastereomeric salts of the compound of Formula II; and then (b) crystallizing a single diastereomeric salt formed of the compound of Formula II, to make the stereochemically pure compound of Formula IIa, or a salt thereof.

In some embodiments, the stereochemically pure compound has greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound greater than about 90% by weight of one stereoisomer of the compound and less than about 10% by weight of the other stereoisomers of the compound.

In some embodiments, the crystallizing step is performed by cooling the mixture of diastereomeric salts of the compound of Formula II (e.g., to a temperature of from 40, 45, 50, 55, or 60° C. to 80, 90, 100, or 110° C., to a temperature of from −10, −5, 0, 5, or 10° C. to 15, 20, 29, or 35° C.).

Further provided are compounds of Formula III:

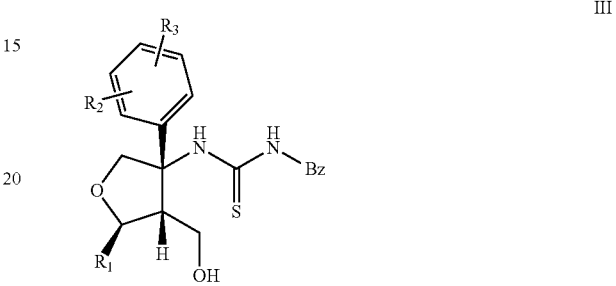

wherein:

$R_1$ is alkyl, haloalkyl, hydroxyalkyl, or —$(C_{1-6})$—OR', wherein R' is an oxygen protecting group; and $R_2$ and $R_3$ are each independently hydrogen or halo (e.g., fluoro);

or a salt thereof.

In some embodiments, Formula III is subject to the proviso that when one of R2 or R3 is ortho-fluoro, and the other is hydrogen, $R_1$ is not —$CH_2F$.

In some embodiments, $R_1$ is trifluoromethyl, hydroxymethyl, monofluoromethyl, or triphenylmethoxymethyl.

In some embodiments, $R_2$ is fluoro, and/or $R_3$ is hydrogen or fluoro.

Examples of compounds of Formula III include:

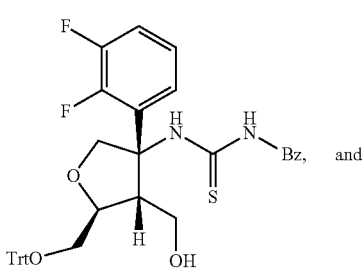

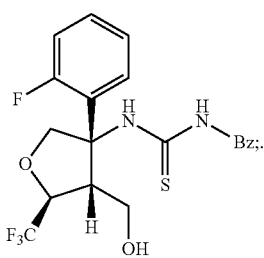

Also provided are compounds of Formula IV:

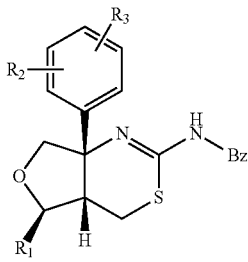

IV wherein:

$R_1$ is alkyl, haloalkyl, hydroxyalkyl, or —$(C_{1-6})$—OR', wherein R' is an oxygen protecting group; and $R_2$ and $R_3$ are each independently hydrogen or halo (e.g., fluoro);

or a salt thereof.

In some embodiments, Formula IV is subject to the proviso that when one of R2 or R3 is ortho-fluoro, and the other is hydrogen, $R_1$ is not —$CH_2F$.

In some embodiments, $R_1$ is trifluoromethyl, hydroxymethyl, monofluoromethyl, or triphenylmethoxymethyl.

In some embodiments, $R_2$ is fluoro, and/or $R_3$ is hydrogen or fluoro.

Examples of compounds of Formula IV include:

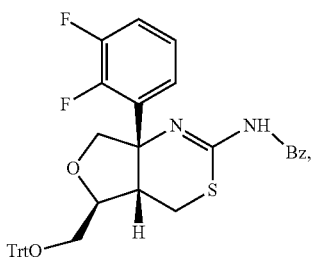

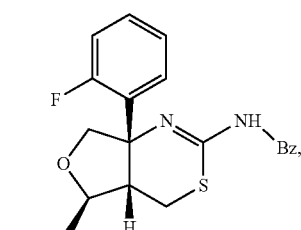

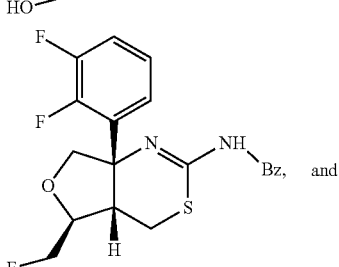

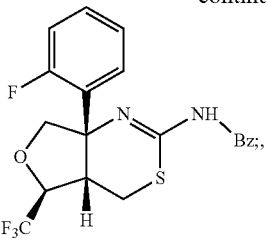

Further provided are compounds of Formula V:

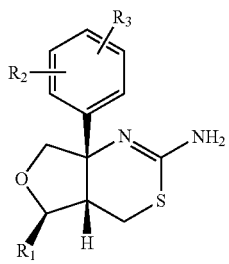

V wherein:

$R_1$ is alkyl, haloalkyl, hydroxyalkyl, or —$(C_{1-6})$—OR', wherein R' is an oxygen protecting group; and $R_2$ and $R_3$ are each independently hydrogen or halo (e.g., fluoro);

or a salt thereof.

In some embodiments, Formula V is subject to the proviso that when one of R2 or R3 is ortho-fluoro, and the other is hydrogen, $R_1$ is not —$CH_2F$.

In some embodiments, $R_1$ is trifluoromethyl, hydroxymethyl, monofluoromethyl, or triphenylmethoxymethyl.

In some embodiments, $R_2$ is fluoro, and/or $R_3$ is hydrogen or fluoro.

Examples of compounds of Formula V include:

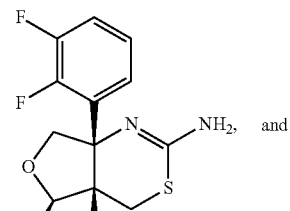

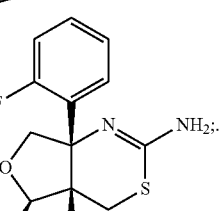
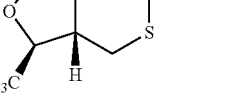

Also provided are methods for making a compound of Formula V:

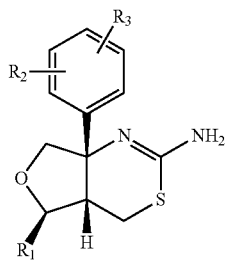

wherein:

$R_1$ is $C_{3-4}$alkyl, halo-$C_{1-4}$alkyl, hydroxy-$C_{1-4}$alkyl, or —$C_{1-4}$alkyl-OR', wherein R' is an oxygen protecting group; and $R_2$ and $R_3$ are each independently hydrogen or halo;

or a salt thereof, comprising the steps of:
(a) providing a mixture of
(i) a compound of Formula III,

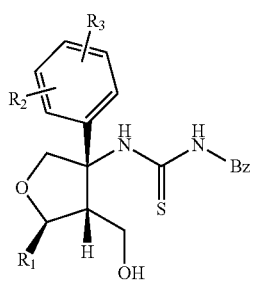

wherein $R_1$, $R_2$ and $R_3$ are as given above for Formula V;
(ii) an amine base (e.g., pyridine, or a substituted pyridine such as collidine); and
(iii) an organic solvent (e.g., an aromatic hydrocarbon solvent, toluene, xylenes, benzene, dichloromethane, etc.),
wherein said mixture is at a temperature at or below 0° Celsius,
(b) reacting the mixture with trifluoromethanesulfonic anhydride, 4-toluenesulfonyl chloride, methanesulfonyl chloride or methanesulfonyl anhydride, and then,
(c) adding:
(i) an alcohol (e.g., propanol, such as 2-propanol); and
(ii) a base, such as a strong base selected from: a hydroxide, an alkoxide, and ammonia,
to make said compound of Formula V.

In some embodiments, the reacting step is carried out at a temperature of from −15, −10, or −5, to 0° Celsius.

Also provided are compound of Formula VI:

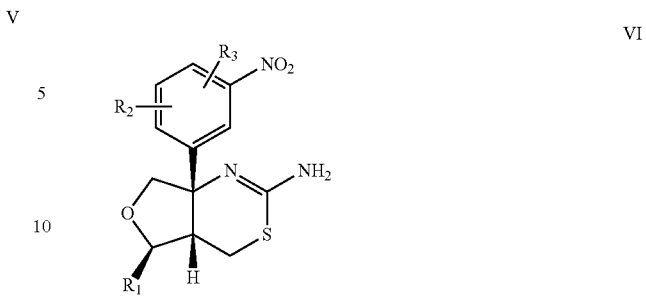

wherein:

$R_1$ is alkyl, haloalkyl, hydroxyalkyl, or —$(C_{1-6})$—OR', wherein R' is an oxygen protecting group; and $R_2$ and $R_3$ are each independently hydrogen or halo (e.g., fluoro);

or a salt thereof.

In some embodiments, Formula VI is subject to the proviso that when one of R2 or R3 is ortho-fluoro, and the other is hydrogen, $R_1$ is not —$CH_2F$.

In some embodiments, $R_1$ is trifluoromethyl, hydroxymethyl, monofluoromethyl, or triphenylmethoxymethyl.

In some embodiments, $R_2$ is fluoro, and/or $R_3$ is hydrogen or fluoro.

Examples of compounds of Formula VI include:

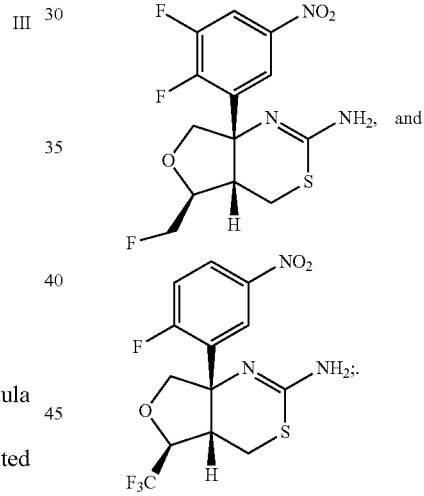

Further provided are compounds of Formula VII:

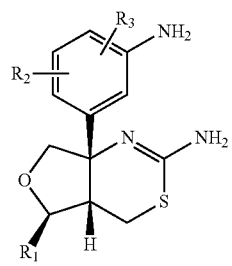

wherein:

$R_1$ is alkyl, haloalkyl, hydroxyalkyl, or —$(C_{1-6})$—OR', wherein R' is an oxygen protecting group; and $R_2$ and $R_3$ are each independently hydrogen or halo (e.g., fluoro);

or a salt thereof.

In some embodiments, $R_1$ is methyl, trifluoromethyl, hydroxymethyl, monofluoromethyl, or triphenylmethoxymethyl.

In some embodiments, $R_2$ is fluoro, and/or $R_3$ is hydrogen or fluoro.

Examples of compound of Formula VII include:

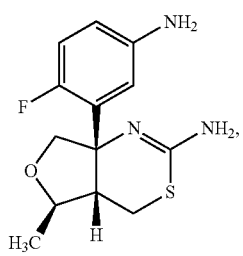

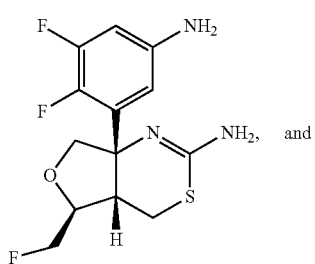

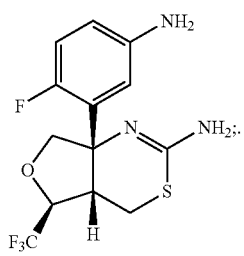

Also provided are methods of making a compound of Formula VII, or a salt thereof, including the step of:

reducing a compound of Formula VI to form a compound of Formula VII, as shown below:

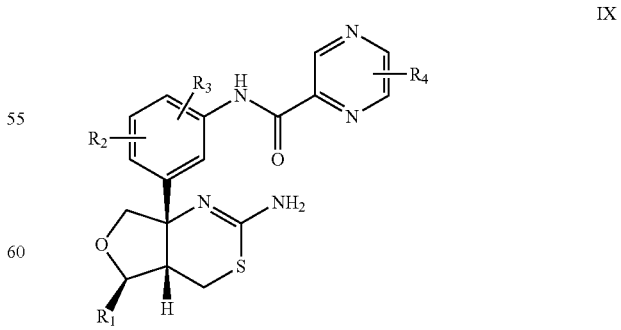

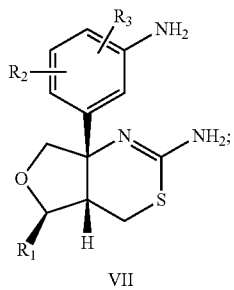

wherein:

$R_1$ is alkyl, haloalkyl, hydroxyalkyl, or —($C_{1-6}$)—OR', wherein R' is an oxygen protecting group; and $R_2$ and $R_3$ are each independently hydrogen or halo.

In some embodiments, $R_1$ is trifluoromethyl, hydroxymethyl, monofluoromethyl, or triphenylmethoxymethyl.

In some embodiments, $R_2$ is fluoro, and/or $R_3$ is hydrogen or fluoro.

In some embodiments, the reducing of the compound of Formula VI to form the compound of Formula VII may include one or more of the steps of:

(a) adding powdered iron to a carbinol solvent to form a mixture thereof;

(b) adding hydrochloric acid (HCl) (e.g., concentrated HCl) to the mixture of step (a);

(c) heating the mixture of step (b) to a temperature of from 31, 40 or 50° C. to 65, 70, 75, 80, 85° C., or to the boiling point of the mixture of step (b) (e.g., for 0-4 hours) to form a heated mixture; and (d) adding the compound of Formula VI, or a salt thereof, to the heated mixture of step (c).

In some embodiments, the method further includes the steps of:

(e) cooling the mixture of step (d) to a temperature of between 10 and 30° C. to form a cooled mixture; and (f) optionally, stirring the cooled mixture (e.g., for 0-4 hours).

In some embodiments, the HCl is provided in an amount selected from the group consisting of: an amount of HCl stoichiometric with respect to the amount of the compound of Formula VI; and an amount of HCl in molar excess with respect to the amount of the compound of Formula VI.

Further provided are methods of making a compound of Formula IX:

IX wherein:

$R_1$ is alkyl, haloalkyl, hydroxyalkyl, or —($C_{1-6}$)—OR', wherein R' is an oxygen protecting group; and $R_2$ and $R_3$ are each independently hydrogen or halogen; and $R_4$ is selected from the group consisting of alkyl, haloalkyl, alkoxy, and alkyl substituted with alkoxy;
  or a salt thereof;
including the step of reacting a compound Formula VII with a pyrazine carboxylic acid of Formula VIII:

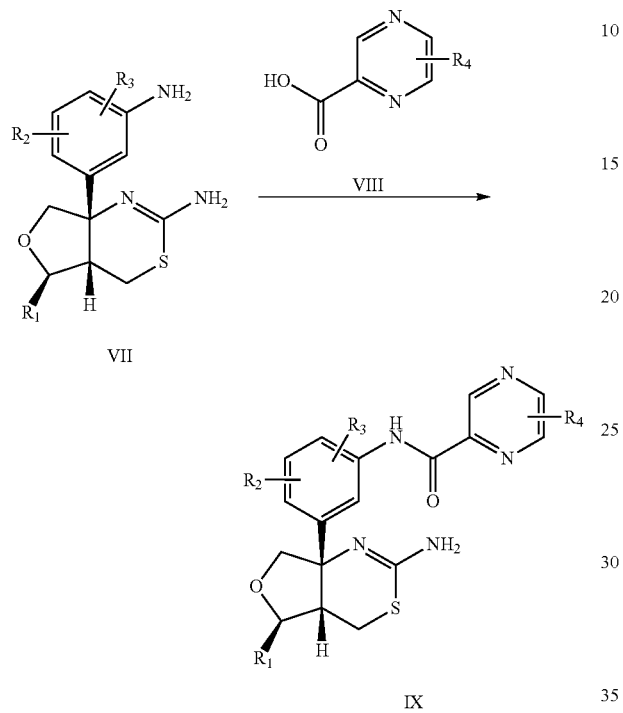

wherein $R_1$, $R_2$, $R_3$ and $R_4$ are as given above,
to form said compound of Formula IX, or a salt thereof.

In some embodiments, the reacting may include one or more of the steps of:

(a) adding thionyl chloride to a solution comprising a compound of Formula VIII in a solvent to make a formed mixture; and (b) adding a compound of Formula VII to the formed mixture of step (a), to form said compound of Formula IX, or a salt thereof.

In some embodiments, the solution comprising the compound of Formula VIII is a solvent is cooled prior to or during the adding step (a) (e.g., to a temperature of from 0 to 25° C.).

In some embodiments, the solvent may include N,N'-dimethylimidazoline-2-one, toluene, methylene chloride, dimethylformamide, N-methylpyrrolidine, or dimethyacetamide.

In some embodiments, the reacting may include one or more of the steps of:

(a) adding ethyl acetate (EtOAc) to a compound of Formula VIII and a compound of Formula VII to make a formed mixture; and (b) adding propane phosphonic acid anhydride (e.g., ®T3P, Archimica, Germany) to the formed mixture of step (a), to form said compound of Formula IX, or a salt thereof.

In some embodiments, the formed mixture may be maintained at a temperature of from 0° C. to 35° C. during said adding step (a).

These compounds, or salts thereof, as well as methods of making, are useful in methods of synthesis of fused aminodihydrothiazine derivatives, such as the method provided below in Scheme I.

Scheme I

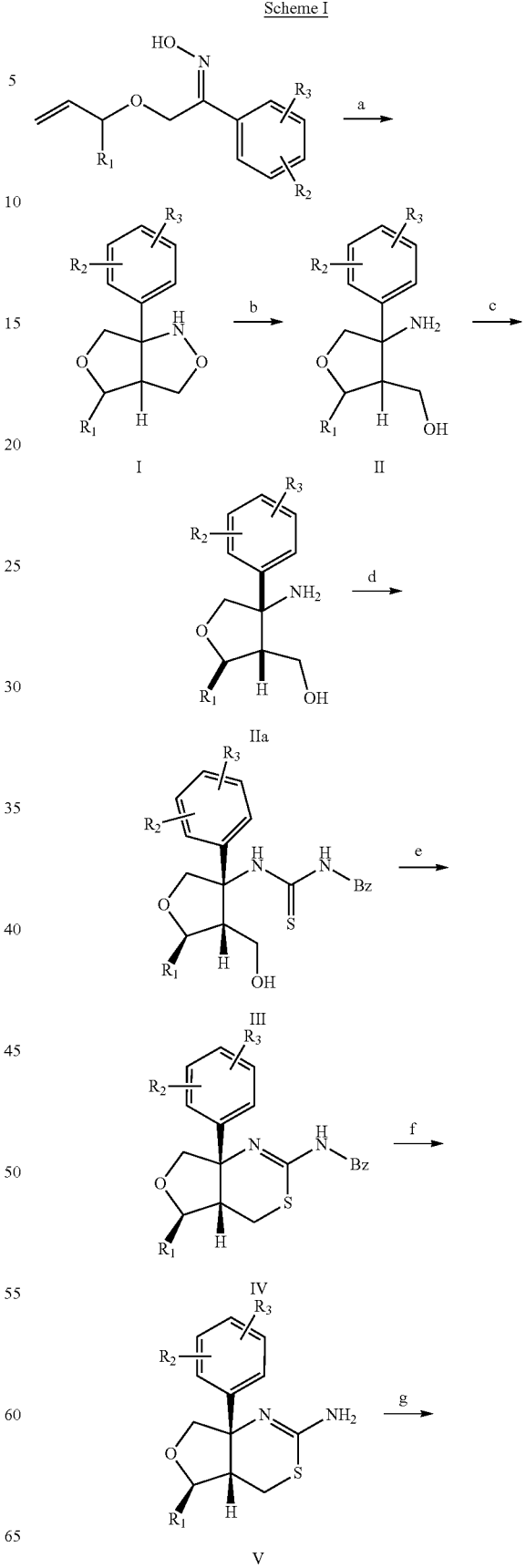

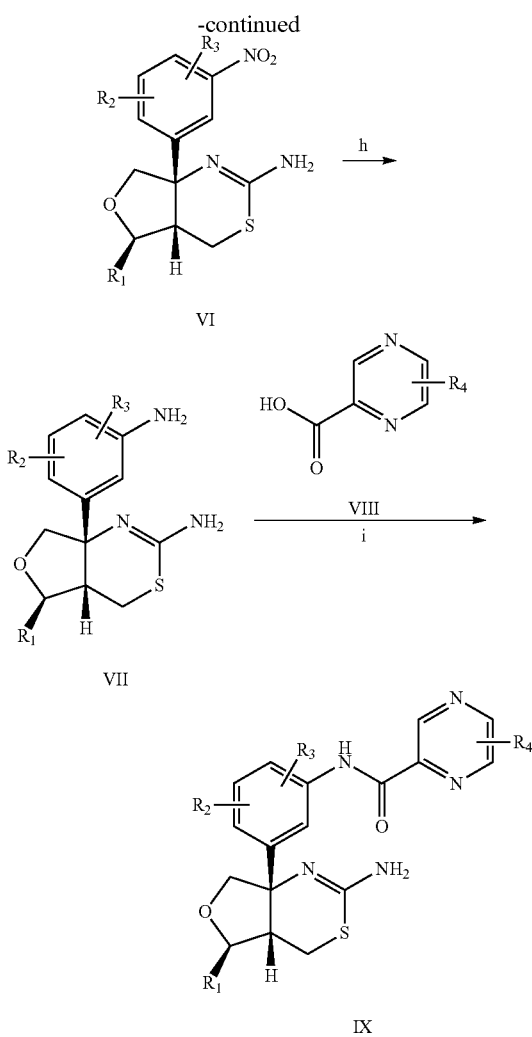

In order that the invention described herein may be more fully understood, the following examples are set forth. It should be understood that these examples are for illustrative purposes only and are not to be construed as limiting this invention in any manner.

EXAMPLES

General

Column chromatography was carried out using Biotage SP4. Solvent removal was carried out using either a Büchii rotary evaporator or a Genevac centrifugal evaporator. Preparative LC/MS was conducted using a Waters autopurifier and 19×100 mm XTerra 5 micron MS C18 column under acidic mobile phase condition. NMR spectra were recorded using Varian 400 MHz spectrometer.

When the term "inerted" is used to describe a reactor (e.g., a reaction vessel, flask, glass reactor, and the like) it is meant that the air in the reactor has been replaced with an essentially moisture-free or dry, inert gas (such as nitrogen, argon, and the like). The term "equivalent" (abbreviation: eq) as used herein describes the stoichiometry (molar ratio) of a reagent or a reacting compound by comparison to a pre-established starting material. The term "weight" (abbreviation: wt) as used herein corresponds to the ratio of the mass of a substance or a group of substances by comparison to the mass of a particular chemical component of a reaction or purification specifically referenced in the examples below. The ratio is calculated as: g/g, or Kg/Kg. The term "volume" (abbreviation: vol) as used herein corresponds to the ratio of the volume of a given substance or a group of substances to the mass or volume of a pre-established chemical component of a reaction or purification. The units used in the equation involve matching orders of magnitude. For example, a ratio is calculated as: mL/mL, mL/g, L/L or L/Kg.

General methods and experimentals for preparing compounds of the present invention are set forth below. In certain cases, a particular compound is described by way of example. However, it will be appreciated that in each case a series of compounds of the present invention were prepared in accordance with the schemes and experimentals described below.

The following abbreviations are used herein:

| Abbreviation | Definition |
|---|---|
| TMS | Trimethylsilyl |
| TBAF | Tetrabutylammonium fluoride |
| NaOH | Sodium hydroxide |
| Bu$_4$N HSO$_4$ | Tetrabutylammonium hydrogen sulfate |
| THF | Tetrahydrofuran |
| rt | Room temperature |
| h | Hour(s) |
| NaCl | Sodium chloride |
| HCOOH | Formic acid |
| V | Volumes |
| wt | Weights |
| CDI | N,N-Carbonyldiimidazole |
| DCM | Dichloromethane |
| Aq | Aqueous |
| Sat. | Saturated |
| HCl | Hydrochloric acid |
| HRMS | High Resolution Mass Spectrometry |
| nBuLi | n-butyl lithium |
| NH$_4$Cl | Ammonium chloride |
| MeOH | Methanol |
| EtOAc | Ethyl acetate |
| NaHCO$_3$ | Sodium bicarbonate |
| M | Molar (moles/liter) |
| T | Temperature |
| MTBE | Methyl tert-butyl ether |
| TLC | Thin layer chromatography |
| N | Normal (equivalents per liter) |
| iPrMgBr | Isopropyl magnesium bromide |
| LiCl | Lithium chloride |
| NaOAc | Sodium acetate |
| NH$_4$OH | Ammonium hydroxide |
| HPLC | High performance liquid chromatography |
| ee | Enantiomeric excess |
| DMI | 1,3-Dimethyl-2-imidazolidinone |
| UV | Ultraviolet |
| RRT | Relative retention time |
| OROT | Optical rotation |
| Bz | Benzoyl |
| ®T3P (Archimica) | n-propyl phosphonic acid anhydride |

A. Preparation of Hexahydrofuroisoxazoles Compounds of Formula I

Example 1

Preparation of 6a-(2-fluorophenyl)-4-(trifluoromethyl)hexahydrofuro-[3,4-c]isoxazole

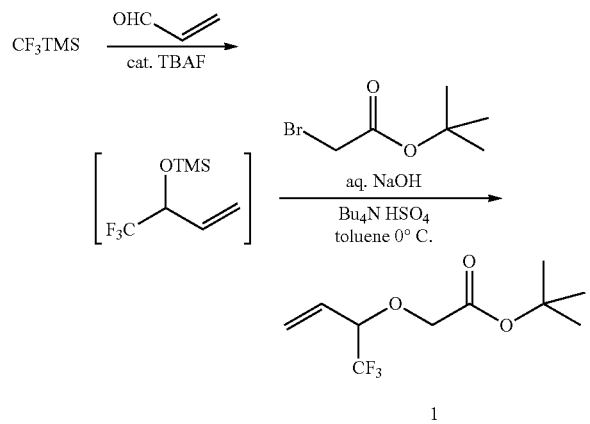

tert-Butyl 2-(1,1,1-trifluorobut-3-en-2-yloxy)acetate. A reaction vessel was charged with toluene (3.2 L), THF (0.60 L) and acrolein (0.40 L, 5.985 mol) at rt under nitrogen. (Trifluoromethyl)trimethylsilane (1.003 kg, 7.059 mol) was added at 17° C. The reaction mixture was cooled to 2.5° C. and TBAF (0.01 M in THF, 0.400 L, 0.004 mol) was added over 2 hours. During addition of TBAF, the temperature of the reaction mixture increased to 65° C. The reaction mixture was cooled to 0° C., and after 2 h, tetra-n-butylammonium hydrogen sulfate (0.171 kg, 0.503 mol) was added, followed by tert-butyl bromoacetate (0.987 kg, 5.064 mol). Sodium hydroxide (50% wt in water, 4.2 kg, 52.6 mol) was added over 2 h while maintaining the temperature under 10° C. After 2 h at 0-5° C., to the reaction mixture was added water (2.9 L) and methyl tert-butyl ether (6.0 L). The aq. phase was extracted one more time with methyl tert-butyl ether (6.0 L). The organic phases were combined and washed with 14% aq. NaCl (3×1.6 L). The organics were concentrated under vacuum to afford the title compound 1 as an oil (1.150 kg, 94.5%) which was used in the subsequent stage without additional purification.

tert-Butyl 2-(1,1,1-trifluorobut-3-en-2-yloxy)acetate: $^1$H NMR (500 MHz, CDCl$_3$) δ 5.86-5.74 (m, 1H), 5.59 (d, J=17.5 Hz, 1H), 5.56 (d, J=10.9 Hz, 1H), 4.37-4.30 (m, 1H), 4.11 (d, J=16.5 Hz, 1H), 4.06 (d, J=16.4 Hz, 1H), 1.40 (s, 9H); $^{13}$C NMR (125 MHz, CDCl$_3$) δ 168.51, 128.49 (d, J=1.7 Hz), 123.86, 123.71 (q, J=281.8 Hz), 82.22, 78.67 (q, J=31.5 Hz), 66.60, 28.02.

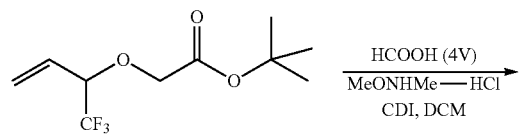

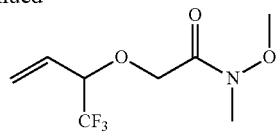

N-Methoxy-N-methyl-2-(1,1,1-trifluorobut-3-en-2-yloxy) acetamide. To a reactor containing tert-butyl 2-(1,1,1-trifluorobut-3-en-2-yloxy)acetate 1 (1.150 kg, 4.788 mol) was added formic acid (6.2 kg) at rt. The reaction mixture was heated to 55-60° C. for 4-5 hours. The formic acid was evaporated under vacuum (T=40-45° C.) and chased with toluene (2×3.0 L). To the residue was added CH$_2$Cl$_2$ (2.0 L) and further concentrated under vacuum. To the resulting residue was added CH$_2$Cl$_2$ (4.6 L) and the solution was cooled to 0° C., followed by N,N-carbonyldiimidazole (1.05 kg, 6.49 mol) in five portions. The mixture was stirred for 30 minutes, and N,O-dimethylhydroxylamine hydrochloride (0.67 kg, 6.72 mol) was added in portions while maintaining temperature below 10° C. The reaction mixture was warmed to rt and stirred over 14 hours. The reaction mixture was cooled to 3.2° C. and imidazole (100.7 g, 1.48 mol) was charged in two portions. The reaction mixture was warmed to rt and water (1.4 kg) was added, followed by methyl tert-butyl ether (14.0 L). The organic phase was washed with 2.0 N aq. HCl (1.0 L and 0.7 L), followed by sat. aq. NaHCO$_3$ (1.2 L) and sat. aq. NaCl (1.20 L). The organics were concentrated to afford the title compound 2 as an oil (0.95 kg, 87.2%).

N-Methoxy-N-methyl-2-(1,1,1-trifluorobut-3-en-2-yloxy)acetamide: $^1$H NMR (500 MHz, CDCl$_3$) δ 5.85-5.76 (m, 1H), 5.62 (d, J=17.2 Hz, 1H), 5.56 (d, J=10.4 Hz, 1H), 4.49-4.34 (m, 3H), 3.68 (s, 3H), 3.67 (s, 1H), 3.18 (s, 3H), 3.08 (s, 1H); $^{13}$C NMR (126 MHz, cdcl$_3$) δ 169.9*, 163.4*, 128.61, 123.87 (d, J=282.0 Hz), 123.82, 78.54 (q, J=31.3 Hz), 66.12, 61.52, 60.56, 36.20, 32.24. Note: this compound is a 3:1 mixture of amide bond rotamers. *Carbonyl chemical shifts estimated indirectly through $^1$H-$^{13}$C HMBC (heteronuclear multiple-bond correlation).

HRMS Calculated for C$_8$H$_{12}$F$_3$NO$_3$ [M+H]$^+$ 228.0848. found 228.0836.

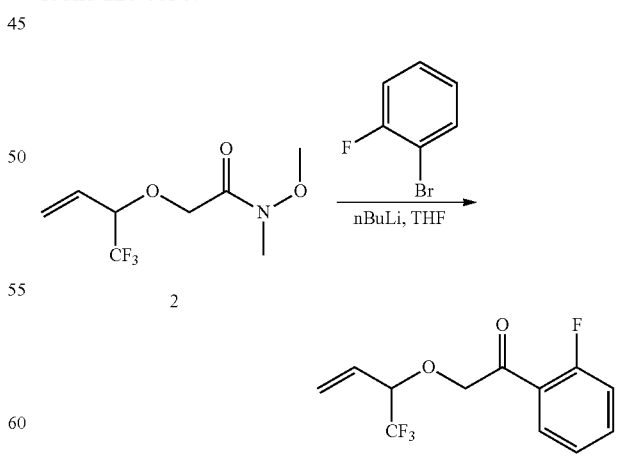

1-(2-Fluorophenyl)-2-(1,1,1-trifluorobut-3-en-2-yloxy) ethanone. To a solution 1-bromo-2-fluorobenzene (0.967 kg, 5.527 mol) in THF (6.2 L) at −75° C., was added n-butyllithium (2.50 M in hexane, 2.09 L, 5.22 mol) while maintaining temperature below −65° C. (ca. 100 min.). After 15 minutes, a solution of N-methoxy-N-methyl-2-(1,1,1-trifluorobut-3-en-2-yloxy)acetamide 2 (0.949 kg, 4.178 mol) in THF (1.6 L) was added while maintaining temperature below −65° C. (ca. 70 min.). After 2.5 h at −78° C., the reaction was quenched by addition of sat. aq. NH$_4$Cl (3.0 L) and methyl tert-butyl ether (9.0 L). The reaction mixture was warmed to rt, the aq. phase was extracted again with methyl tert-butyl ether (2.5 L). The organic phases were combined, washed with sat, aq. NaCl (2×0.3 L) and concentrated under vacuum to afford the title compound 3 as an oil (1.007 kg, 80.0%).

1-(2-Fluorophenyl)-2-(1,1,1-trifluorobut-3-en-2-yloxy)ethanone: $^1$H NMR (500 MHz, CDCl$_3$) δ 7.96 (td, J=7.6, 1.8 Hz, 1H), 7.62-7.54 (m, 1H), 7.33-7.25 (m, 1H), 7.20-7.12 (m, 1H), 5.86 (ddd, J=17.5, 10.4, 7.3 Hz, 1H), 5.60 (dd, J=20.5, 13.8 Hz, 2H), 4.91-4.76 (m, 2H), 4.39 (dq, J=12.8, 6.4 Hz, 1H); $^{13}$C NMR (125 MHz, CDCl$_3$) δ 193.55, 162.14 (d, $J_{CF}$=254.1 Hz), 135.36 (d, $J_{CF}$=9.2 Hz), 130.62 (d, $J_{CF}$=3.2 Hz), 128.49, 124.85 (d, $J_{CF}$=3.3 Hz), 123.89, 122.93, 122.72 (d, $J_{CF}$=24.5 Hz), 116.50 (d, $J_{CF}$=23.7 Hz), 78.97 (q, $J_{CF}$=31.4 Hz), 74.56 (d, $J_{CF}$=12.4 Hz).

HRMS Calculated for $C_{12}H_{10}F_4O_2$ [M+H]$^+$ 263.0695. found 263.0709.

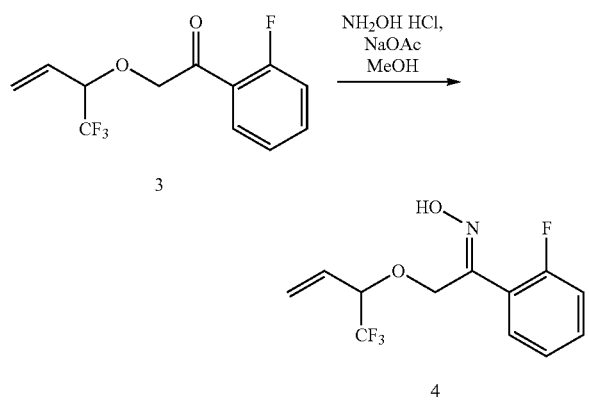

1-(2-Fluorophenyl)-2-(1,1,1-trifluorobut-3-en-2-yloxy)ethanone oxime. To a reactor was added hydroxylamine hydrochloride (0.34 kg, 4.95 mol), sodium acetate (0.47 kg, 5.70 mol) and MeOH (2.68 L). To this suspension was charged a solution of 1-(2-fluorophenyl)-2-(1,1,1-trifluorobut-3-en-2-yloxy)ethanone 3 (0.998 kg, 3.806 mol) in MeOH (1.8 L) and the reaction mixture was heated to 40-50° C. Upon completion (ca. 2 h) the reaction mixture was cooled to rt, and filtered over Celite (0.5 wt) and rinsed with EtOAc (3.0 L). The filtrate was concentrated under vacuum and to the resulting residue was added methyl tert-butyl ether (6.3 L), water (0.94 L) and sat. aq. NaHCO$_3$ (2.5 L). The organic phase was washed once with water (1.6 L) and sat. aq. NaCl (0.1 L). The organic phase was concentrated under vacuum to afford the title compound 4 as an oil (1.03 kg, 95.0%).

1-(2-Fluorophenyl)-2-(1,1,1-trifluorobut-3-en-2-yloxy)ethanone oxime: $^1$H NMR (500 MHz, CDCl$_3$) δ 7.49-7.35 (m, 2H), 7.24-7.06 (m, 2H), 5.78-5.65 (m, 1H), 5.54-5.40 (m, 2H), 4.89-4.81 (m, 1H), 4.53 (d, J=12.6 Hz, 1H), 4.47 (d, J=12.6 Hz, 0.5H), 4.27-4.18 (m, 1H), 4.13-4.05 (m, 0.5H).

HRMS Calculated for $C_{12}H_{11}F_4NO_2$ [M+H]$^+$ 278.0804. found 278.0780.

Note: Oxime 4 exists as an equilibrium of structural isomers, which accounts for the less-than-whole-number integral values.

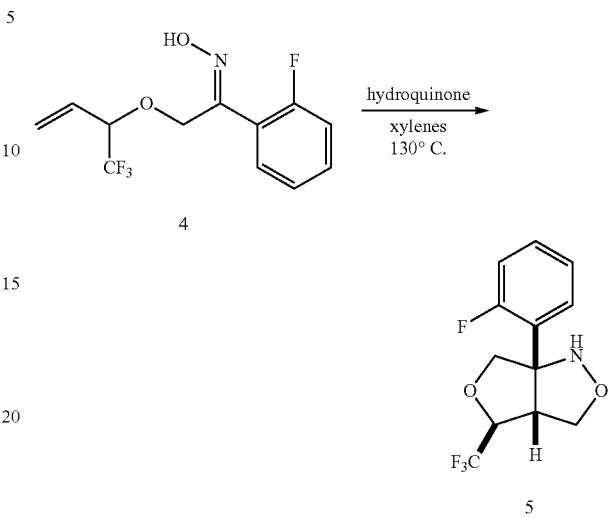

6a-(2-Fluorophenyl)-4-(trifluoromethyl)hexahydrofuro[3,4-c]isoxazole. To a solution of 1-(2-fluorophenyl)-2-(1,1,1-trifluorobut-3-en-2-yloxy)ethanone oxime 4 (1.085 kg, 3.328 mol) in xylenes (6.9 L) was added hydroquinone (86.2 g, 0.8 mol) at rt. The solution was heated to 128° C. (internal temperature) for 18 h. The solution was cooled to rt, and hexanes (7.0 L) was added, followed by 4.0 M aq. HCl (2.4 L). The reaction mixture was stirred for 1 h, and filtered. To the solid was added water (2.0 L), methyl tert-butyl ether (7.0 L) and 25% wt. aq. NaOH (0.4 L). The aq, layer was extracted once with methyl tert-butyl ether (7.0 L), the organics were combined, washed with 27% aq. NaCl (2.0 L) and concentrated under vacuum to a black oil 5 (512.0 g, 56%).

6a-(2-Fluorophenyl)-4-(trifluoromethyl)hexahydrofuro[3,4-c]isoxazole: $^1$H NMR (500 MHz, CDCl$_3$) δ 7.64-7.52 (m, 1H), 7.39-7.31 (m, 1H), 7.19 (td, J=7.7, 1.2 Hz, 1H), 7.11 (ddd, J=11.9, 8.2, 1.0 Hz, 1H), 4.54 (d, J=10, 1 Hz, 1H), 4.34-4.23 (m, 1H), 4.26-4.17 (m, 1H), 4.16 (d, J=10.2 Hz, 1H), 4.10 (d, J=8.5 Hz, 1H), 3.71 (d, J=20.2 Hz, 1H); $^{13}$C NMR (125 MHz, CDCl$_3$) δ 160.59 (d, $J_{CF}$=247.0 Hz), 130.50 (d, $J_{CF}$=8.7 Hz), 128.72, 124.69 (d, $J_{CF}$=3.3 Hz), 124.45 (q, $J_{CF}$=281.8 Hz), 124.43 (d, $J_{CF}$=11.9 Hz), 116.66 (d, $J_{CF}$=22.7 Hz), 83.70 (q, $J_{CF}$=32.1 Hz), 78.17 (d, $J_{CF}$=3.1 Hz), 77.63, 54.53.

HRMS Calculated for $C_{12}H_{11}F_4NO_2$ [M+H]$^+$ 278.0804. found 278.0802.

Example 2

Preparation of 6a-(2-fluorophenyl)-4-methylhexahydrofuro[3,4-c]isoxazole

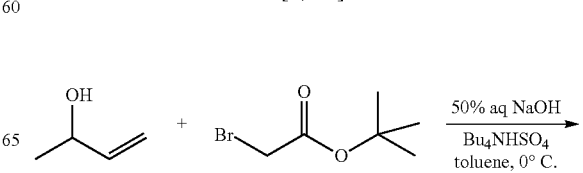

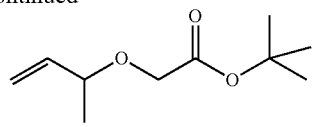

6 tert-Butyl 2-(but-3-en-2-yloxy)acetate: A reactor was charged with tetrabutylammonium hydrogen sulfate (0.17 Wt, 0.10 eq) and toluene (2.6 Wt, 3.0 V). The mixture was stirred and cooled to 0-5° C. While maintaining the internal temperature below 10° C., 50 wt % aqueous sodium hydroxide (4.5 wt, 3.0 V, 10.5 eq; 50% wt sodium hydroxide made from 2.25 wt of sodium hydroxide and 2.25 wt of water) was added, followed by 3-buten-2-ol (0.45 Wt, 0.53 V, 1.20 eq). The mixture was stirred at 0-10° C. for 15 minutes. tert-Butyl bromoacetate (1.0 Wt, 1.00 eq) was added while maintaining the internal temperature between 0-10° C. After the addition, the mixture was stirred between 0-5° C. for 1 h and monitored for complete consumption of tert-butyl bromoacetate (target >98% conversion). The reactor was charged with water (3.0 Wt, 3.0 V) and MTBE (4.4 Wt, 6.00 V) and warmed to 20-25° C. The biphasic mixture was stirred vigorously for 15 minutes, and then allowed to partition. The organic layer was washed with water (1.5 Wt, 1.5 V). The organic layer was concentrated under reduced pressure (T<40° C. and not less than 15 torr or 20 mbar). Heptane (1.0 wts, 1.5 V) and MTBE (1.1 wts, 1.5 V) were added. The solution was filtered to remove particulates, and rinsed with additional heptane: MTBE as necessary to clear the product. The solution was returned to the reactor and concentrated under reduced pressure to give 6 (0.91 Wt, 95.0%) as an oil with less than 1 volume of solvent.

tert-Butyl 2-(but-3-en-2-yloxy)acetate: $^1$H NMR (500 MHz, CDCl$_3$) δ 5.78-5.66 (m, 1H), 5.23-5.12 (m, 2H), 4.00-3.85 (m, 3H), 1.47 (s, 11H), 1.31 (d, J=6.4 Hz, 3H); $^{13}$C NMR (125 MHz, CDCl$_3$) δ 169.87, 139.30, 116.72, 81.20, 77.53, 65.83, 28.04, 27.92, 21.08.

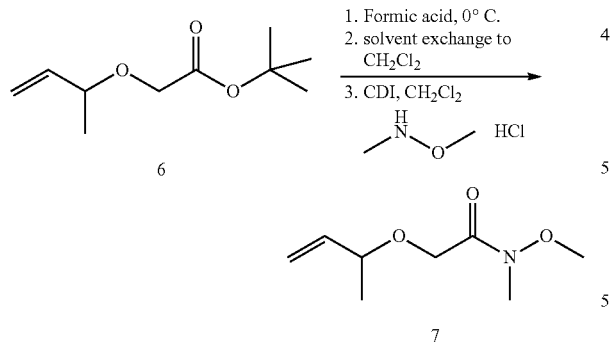

2-(But-3-en-2-yloxy)-N-methoxy-N-methylacetamide: A reactor was charged with the toluene solution of 6 (1.0 Wt, 1.0 V), and cooled to 0-5° C. Formic acid (4.84 Wt, 4.0 V, 19.2 eq) was added while maintaining the internal temperature below 10° C. After addition of formic acid, the mixture was heated to 35-40° C. for three hours. The reaction was monitored for consumption of 6 (>90% conversion). Upon completion formic acid was removed under vacuum at 45° C. Residual formic acid was removed by two azeotropic distillations with toluene (2.0-2.50 Wt, 2.3-3.0 V) at 45° C. under vacuum to give crude acid (0.67 Wt, 95%).

The crude acid was dissolved in dichloromethane (5.3 Wt, 4.0 V) and cooled at 0° C. To the solution is added N,N-carbonyldiimidazole (1.15 Wt, 1.28 eq) in 5-7 portions maintaining the reaction temperature between 0-10° C. Note: Gas evolution occurs during the reaction. Upon complete addition of N,N-carbonyldiimidazole, the mixture was warmed to 15-20° C. and stirred for 30 minutes. The reaction mixture was then cooled back to 0-5° C. N,O-dimethylhydroxylamine hydrochloride (0.71 Wt, 1.33 eq) was added in portions maintaining the reaction between 0-10° C. After the addition is complete, the reaction mixture was warmed to 15-20° C. The reaction was monitored for complete consumption of intermediate acid (>98% conversion). The reactor was charged with water (1.2 Wt, 1.2 V) at 0-10° C. and then MTBE (9.1 Wt, 12.3V). The biphasic mixture was stirred vigorously for 15 minutes, and then allowed to partition. The aqueous layer was separated, the combined organic layer was then washed with 2N HCl (1.8 Wt, 1.8 V), (check pH to make sure it is between 1-3 or check organic layer by TLC to make sure the polar material below product is removed. Charge more 2N HCl if necessary). The aqueous layer was separated, the organics were washed with saturated sodium bicarbonate (NaHCO3, 0.1 Wt and water, 1.1 Wt, 1.2 V) and then 20% NaCl in water (1.2 Wt, 1.2V). The organic phase was concentrated under reduced pressure. Anhydrous THF (1.33 Wt, 1.50 V) was added, and the solution was filtered to remove particulates, rinsing with additional anhydrous THF as necessary to clear the product. The THF solution was returned to the reactor and concentrated under reduced pressure to give 7 (0.73 Wt, 75.0%) as an oil.

2-(But-3-en-2-yloxy)-N-methoxy-N-methylacetamide: $^1$H NMR (500 MHz, CDCl$_3$) δ 5.80-5.70 (m, 1H), 5.21 (d, J=17.3 Hz, 1H), 5.17 (d, J=10.3 Hz, 1H), 4.28 (d, J=15.6 Hz, 1H), 4.18 (d, J=15.6 Hz, 1H), 4.03-3.96 (m, 1H), 3.68 (s, 3H), 3.18 (s, 3H), 1.32 (d, J=6.4 Hz, 3H); $^{13}$C NMR (125 MHz, CDCl$_3$) δ 139.62, 116.73, 77.49, 65.34, 61.44, 32.36, 21.25.

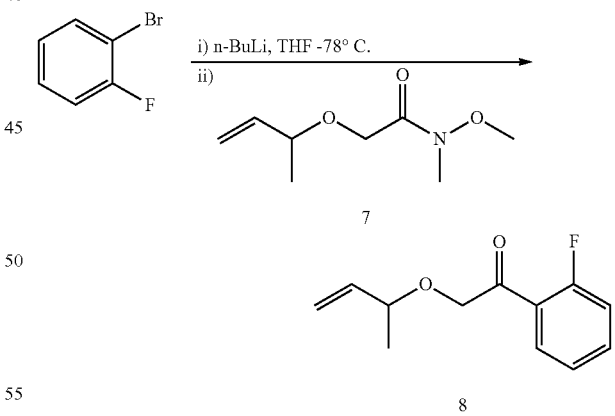

2-(But-3-en-2-yloxy)-1-(2-fluorophenyl)ethanone. A reactor was charged with 1-bromo-2-fluorobenzene (1.31 Wt, 1.30 eq) and anhydrous THF (7.60 Wt, 8.6 V). The reaction mixture was cooled to below −70° C. 2.5 M n-butyl lithium in hexanes (1.94 Wt, 2.89 V, 1.25 eq) was added while maintaining the internal temperature below −60° C. Upon complete addition, the mixture was stirred at a temperature below −60° C. for 15 minutes and then a solution of amide 7 (1.0 Wt, 1.0 eq.) in THF (1.9 Wt, 2.2 V) was added while maintaining the internal temperature below −60° C. After stirring the reaction for 60 minutes, the reaction was monitored for complete consumption of amide 7 (>90% conversion). The reactor was charged with 20 wt % aqueous ammonium chloride (1.0 Wt, 1.0 V), and warmed to 20-25° C. The mixture was transferred to a work-up vessel containing additional 20 wt % aqueous ammonium chloride (3.0 Wt, 3.0 V). The mixture was stirred for 15 minutes, then stirring was stopped and the phases separated. The lower aqueous layer was returned to the reactor. MTBE (4.45 Wt, 6.0 V) was charged. The biphasic mixture was stirred vigorously for 15 minutes, and then allow to partition. The organic layers were combined and washed with 25 wt % aqueous sodium chloride (4.75 Wt, 4.75 V). The organic phase was concentrated under reduced pressure (T<40° C.). Anhydrous THF (1.78 Wt, 2.0 V), was added and the mixture was filtered to remove particulates, rinsing with additional anhydrous THF as necessary to clear the product. The THF solution was returned to the reactor and concentrated under reduced pressure to give ketone 8 (0.8 Wt, 73.0%) as an oil.

2-(But-3-en-2-yloxy)-1-(2-fluorophenyl)ethanone: $^1$H NMR (500 MHz, CDCl$_3$) δ 7.93 (td, J=7.6, 1.8 Hz, 1H), 7.57-7.49 (m, 1H), 7.24 (dt, J=14.6, 3.8 Hz, 1H), 7.12 (ddd, J=11.0, 8.3, 0.8 Hz, 1H), 5.21 (dd, J=17.3, 1.3 Hz, 1H), 5.17 (dd, J=10.3, 0.8 Hz, 1H), 4.69 (dd, J=18.1, 3.2 Hz, 1H), 4.60 (dd, J=18.1, 3.4 Hz, 1H); 4.00 (dq, J=12.9, 6.4 Hz, 1H), 1.36 (d, J=6.4 Hz, 3H); $^{13}$C NMR (125 MHz, CDCl$_3$) δ 195.24 (d, J$_{CF}$=5.3 Hz), 162.03 (d, J$_{CF}$=253.9 Hz), 139.42, 134.86 (d, J$_{CF}$=8.9 Hz), 130.64 (d, J$_{CF}$=3.4 Hz), 124.67 (d, J$_{CF}$=3.2 Hz), 123.57 (d, J$_{CF}$=15.3 Hz), 116.89, 116.45 (d, J$_{CF}$=23.7 Hz), 77.93, 74.11 (d, J$_{CF}$=11.2 Hz), 21.19.

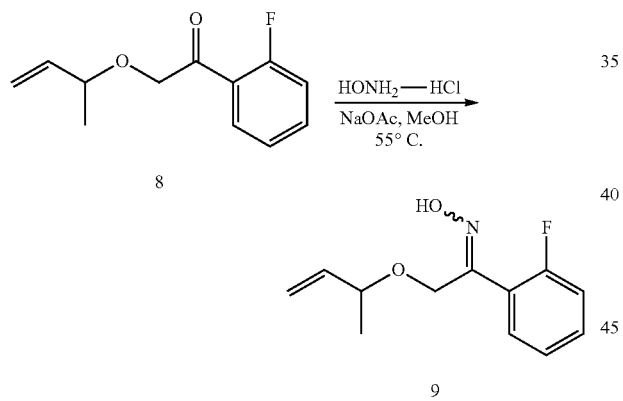

2-(But-3-en-2-yloxy)-1-(2-fluorophenyl)ethanone oxime. A reactor was charged with crude ketone 8 (1.0 Wt, 1.0 eq), hydroxylamine hydrochloride (0.43 Wt, 1.30 eq.), sodium acetate (0.59 Wt, 1.50 eq.), and methanol (4.6 Wt, 5.8 V). The mixture was warmed to between 50-55° C., and then continued stirring for 1-2 hr. The reaction was monitored for consumption of ketone 8 (>95% conversion). The mixture was cooled to 15-20° C., then filtered the reaction mixture to remove solids. The solids were rinsed with ethyl acetate until product is cleared (3.6 Wt, 4.0 V). The filtrates were returned to the reactor and concentrated under reduced pressure (T<40° C.). MTBE (5.9 Wt, 8.0 V) and water (1.0 Wt, 1.0 V) were charged. The biphasic mixture was stirred vigorously for 15 minutes, and then partitioned. The organic phase was washed sequentially with 10 wt % aqueous sodium bicarbonate (3.2 Wt, 3.2 V), water (2.0 Wt, 2.0 V), and finally 25 wt % aqueous sodium chloride (1.0 Wt, 1.0 V). The organic phase was concentrated under reduced pressure (T<40° C.). Anhydrous THF (1.78 Wt, 2.0 V) was added, and the mixture filtered to remove particulates, rinsing with additional anhydrous THF as necessary to clear the product. The THF solution was returned to the reactor and concentrated under reduced pressure to give oxime 9 (0.8-1.2 Wt, 90.0%) as an oil.

2-(But-3-en-2-yloxy)-1-(2-fluorophenyl)ethanone oxime: $^1$H NMR (500 MHz, cdcl$_3$) δ 7.45 (ddd, J=9.2, 6.2, 2.5 Hz, 1H), 7.38-7.30 (m, 1H), 7.20-7.03 (m, 2H), 5.73-5.58 (m, 1H), 5.21-5.05 (m, 2H), 4.67 (s, 2H), 4.38 (d, J=13.0 Hz, 1H), 4.26 (d, J=13, 0 Hz, 1H), 3.97-3.88 (m, 1H), 3.79-3.72 (m, 1H), 1.18 (d, J=6.4 Hz, 1H), 1.05 (d, J=6.4 Hz, 2H); $^{13}$C NMR (126 MHz, cdcl$_3$) δ 160.68 (d, J$_{CF}$=249.9 Hz), 159.13 (d, J$_{CF}$=249.1 Hz), 156.42, 151.80, 139.39, 130.78 (d, J$_{CF}$=8.2 Hz), 130.67 (d, J$_{CF}$=8.4 Hz), 130.27 (d, J$_{CF}$=3.7 Hz), 129.77 (d, J$_{CF}$=4.2 Hz), 123.96 (d, J$_{CF}$=3.5 Hz), 123.86 (d, J$_{CF}$=3.4 Hz), 122.51 (d, J$_{CF}$=14.1 Hz), 120.08 (d, J$_{CF}$=17.1 Hz), 116.59, 116.29, 115.72 (d, J$_{CF}$=7.4 Hz), 115.55 (d, J$_{CF}$=7.7 Hz), 77.45, 76.53, 68.48 (d, J$_{CF}$=1.7 Hz), 77.45, 76.53, 68.48 (d, J$_{CF}$=1.7 Hz), 62.01 (d, J$_{CF}$=2.4 Hz), 20.99, 20.81. Note: there are many $^1$H and $^{13}$C signals because this compound is a mixture of four possible isomers,

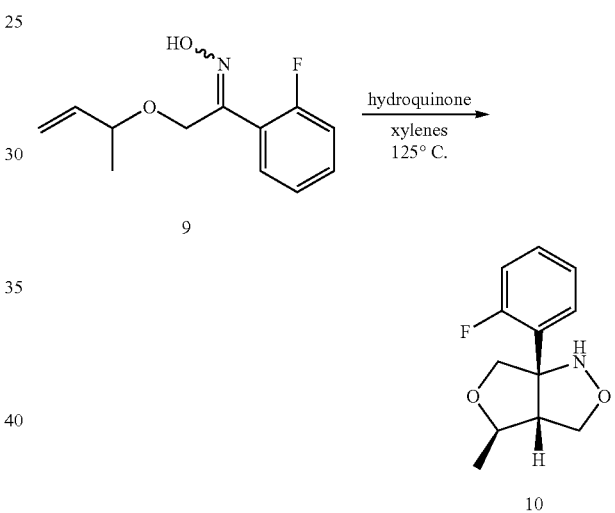

6a-(2-fluorophenyl)-4-methylhexahydrofuro[3,4-c]isoxazole. A reactor was charged with oxime 9 (1.0 Wt, 1.0 eq), xylenes (6.8 Wt, 7.9 V) and then hydroquinone (0.10 Wt, 0.2 eq.). The mixture was heated to between 125-130° C. and monitored the reaction for consumption of oxime 9 (>90% conversion). The mixture was cooled to 20-25° C. 2N aqueous hydrochloric acid (4.0 Wt, 4.0 V) was charged. The biphasic mixture was stirred vigorously for 15 minutes, and then partitioned the phases. The organic phase was extracted with 2N aqueous hydrochloric acid (3.0 Wt, 3.0 V). Note: the product resides in the aqueous layers. The aqueous phases were returned to the reactor. Tert-butyl methyl ether (5.8 Wt, 7.9 V) was charged and then sodium hydroxide (0.55 Wt) to adjust the pH to 9-10. The biphasic mixture was stirred vigorously for 15 minutes, and then the phases were partitioned. The aqueous phase was extracted a second time with MTBE (5.8 Wt, 8.0 vol). The combined organic phases were washed with 25 wt % aqueous sodium chloride (1.0 Wt, 1.0 V). The organic phase was concentrated under reduced pressure (T<40° C.). Anhydrous THF (1.0 Wt, 1.1 V) was added, and filtered to remove particulates, rinsing with additional anhydrous THF as necessary to clear the product. The THF solution was returned to the reactor and concentrated under reduced pressure to give tetrahydroisoxazole 10 (0.6-0.8 Wt, 65.0%) as an oil.

6a-(2-fluorophenyl)-4-methylhexahydrofuro[3,4-c]isoxazole: $^1$H NMR (400 MHz, CDCl$_3$) δ 7.61 (t, J=8.0 Hz, 1H), 7.30 (ddd, J=15.0, 5.2, 1.8 Hz, 1H), 7.19-7.03 (m, 2H), 4.36 (d, J=10.2 Hz, 1H), 4.23-4.16 (m, 1H), 4.05 (dt, J=12.2, 6.2 Hz, 1H), 3.98-3.87 (m, 2H), 3.19-3.09 (m, 1H), 1.40 (d, J=6.4 Hz, 3H). Note: no $^{13}$C-NMR data was available for this compound.

Alternative Procedure #1 for Preparation of Ketone 8

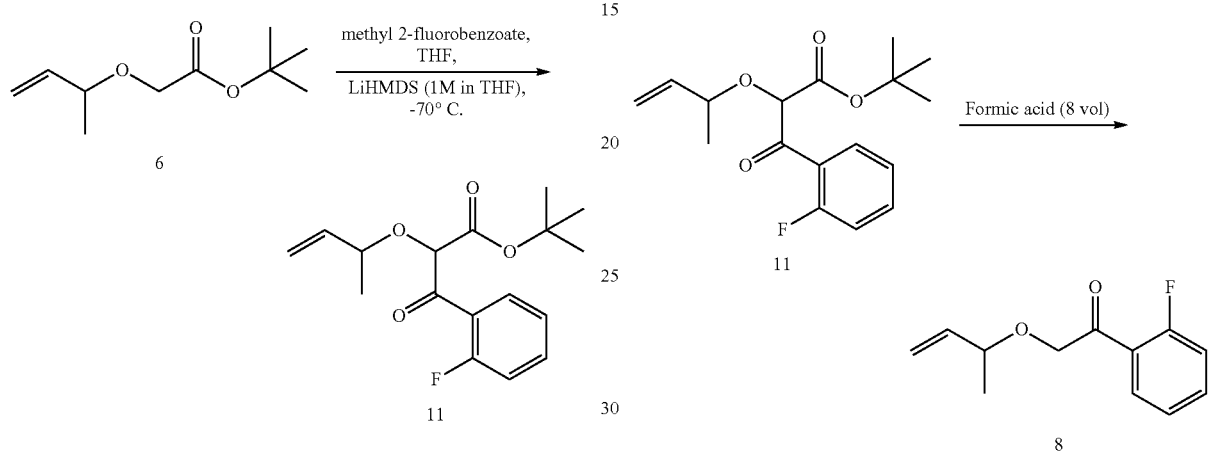

tert-Butyl 2-(but-3-en-2-yloxy)-3-(2-fluorophenyl)-3-oxopropanoate. To a reactor under nitrogen atmosphere was added a toluene solution of ester 6 (1.00 Wt, 1.0 eq), methyl 2-fluorobenzoate (0.91 Wt, 0.75 Vol 1.10 eq), and THF (0.53 Wt, 1.8 Vol). The solution was cooled to below −70° C. Lithium hexamethyldisilazide (LiHMDS, 1.0M in THF, 7.6 Wt, 8.6 Vol, 1.6 eq) was added at such rate that the internal temperature does not exceed −60° C. After completion of the LiHMDS addition, the mixture was warmed (rate between 10-20° C./h) and stirred at −40° C. for 1 h. The reaction was monitored by GC (Conversion Target ≥95%). If after 4 h the conversion is still under targeted amount, additional LiHMDS 1M in THF was added (1.1 eq based on unreacted starting material). After achieving the target conversion, the internal temperature was raised (rate between 20-30° C./h) to −15 to −20° C. 25 wt % aqueous ammonium chloride (1.7 Wt, 1.6 Vol) was added to the reactor keeping the internal temperature below 0° C. Upon completion of the addition, the mixture was warmed to >0° C., and transferred to a vessel containing 25 wt % aqueous ammonium chloride (4.4 Wt, 4.1 Vol) and water (1.1 Wt, 1.1 Vol). The mixture was stirred for at least 30 min at 20-25° C. The lower aqueous layer was removed and the organic layer was washed with 20 wt % aqueous sodium chloride (3.0 Wt, 1.4 Vol). The mixture was stirred for at least 15 minutes then allowed to settle. The lower aqueous layer was removed. The organic phase was concentrated under reduce pressure (Jacket <25° C.) until distillation ceases. Toluene (6.6 Wt, 6.7 Vol) was added and the resulting mixture was washed with water (3.0 Wt, 3.0 Vol), stirred for at least 15 min, then allowed to settle. The organics were washed with water (3.0 Wt, 3.0 Vol) until pH is constant at pH=7-8. The organic phase was washed with 20% aqueous sodium chloride (3.0 Wt, 1.4 Vol). The organic phase was concentrated under reduced pressure (jacket <25° C.) to afford ketoester 11 (2.1 Wt) as an orange oil.

tert-Butyl 2-(but-3-en-2-yloxy)-3-(2-fluorophenyl)-3-oxopropanoate: $^1$H NMR (500 MHz, CDCl$_3$) δ 7.88-7.78 (m, 1H), 7.57-7.48 (m, 1H), 7.29-7.19 (m, 1H), 7.17-7.07 (m, 1H), 5.85-5.64 (m, 1H), 5.28-5.13 (m, 2H), 5.09 (s, 1H), 5.05 (s, 1H), 4.18-4.10 (m, 1H), 4.02-3.94 (m, 1H), 1.39 (s, 9H), 1.37 (s, 9H), 1.35 (d, J=6.3 Hz, 3H), 1.28 (d, J=6.4 Hz, 3H); $^{13}$C NMR (125 MHz, CDCl$_3$) δ 193.17, 193.14, 192.33, 192.30, 166.57, 166.16, 162.44, 162.36, 160.42, 160.33, 138.93, 138.80, 134.76, 134.68, 134.61, 131.17, 131.15, 131.05, 131.02, 124.50, 124.47, 124.40, 124.37, 117.86, 117.60, 116.37, 116.34, 116.19, 116.16, 82.95, 82.91, 82.76, 82.73, 82.38, 82.34, 78.75, 78.48, 27.82, 27.76, 21.21, 21.13. Note: this compound is a mixture of diastereomers.

2-(But-3-en-2-yloxy)-1-(2-fluorophenyl)ethanone. To a reactor under nitrogen atmosphere was added ketoester 11 (1.00 Wt, 1.0 eq) and formic acid (10.0 Wt, 8.0 Vol). The resulting mixture was stirred at 25-30° C. for 12 h then sampled for conversion (Target >97%). After achieving the target conversion, the mixture was concentrated under reduced pressure maintaining the internal temperature below 30° C. Toluene (1.4 Wt, 1.6 Vol) was charged and the mixture was concentrated under reduced pressure maintaining the internal temperature below 30° C. to azeotrope residual formic acid. Toluene (1.4 Wt, 1.6 Vol) was charged and the mixture was concentrated under reduced pressure maintaining the internal temperature below 30° C. The crude ketone 8 (0.6 Wt, 77%) was used directly in the next stage.

2-(But-3-en-2-yloxy)-1-(2-fluorophenyl)ethanone: $^1$H NMR (500 MHz, CDCl$_3$) δ 7.93 (td, J=7.6, 1.8 Hz, 1H), 7.57-7.49 (m, 1H), 7.24 (dt, J=14.6, 3.8 Hz, 1H), 7.12 (ddd, J=11.0, 8.3, 0.8 Hz, 1H), 5.21 (dd, J=17.3, 1.3 Hz, 1H), 5.17 (dd, J=10.3, 0.8 Hz, 1H), 4.69 (dd, J=18.1, 3.2 Hz, 1H), 4.60 (dd, J=18.1, 3.4 Hz, 1H); 4.00 (dq, J=12.9, 6.4 Hz, 1H), 1.36 (d, J=6.4 Hz, 3H); $^{13}$C NMR (125 MHz, CDCl$_3$) δ 195.24 (d, $J_{CF}$=5.3 Hz), 162.03 (d, $J_{CF}$=253.9 Hz), 139.42, 134.86 (d, $J_{CF}$=8.9 Hz), 130.64 (d, $J_{CF}$=3.4 Hz), 124.67 (d, $J_{CF}$=3.2 Hz), 123.57 (d, $J_{CF}$=15.3 Hz), 116.89, 116.45 (d, $J_{CF}$=23.7 Hz), 77.93, 74.11 (d, $J_{CF}$=11.2 Hz), 21.19.

Alternative Procedure #2 for Preparation of Ketone 8

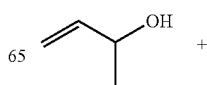 +

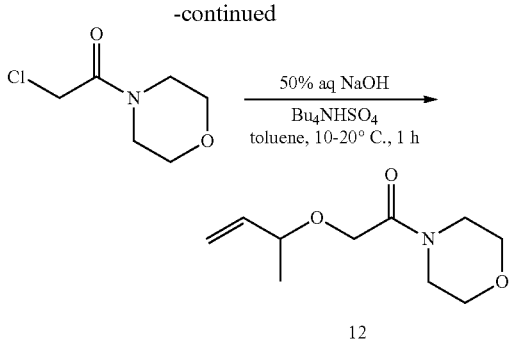

2-(But-3-en-2-yloxy)-1-morpholinoethanone. A reactor was charged with tetrabutylammonium hydrogen sulfate (0.10 eq) and toluene (4.0 V). The mixture was cooled to 10-20° C. While maintaining the internal temperature below 20° C., 50 wt % aqueous sodium hydroxide (2.2 V, 9.7 eq) and then 3-buten-2-ol (0.66 V, 1.25 eq) were added. The mixture was stirred at 10-20° C. for 15 minutes. 4-(chloroacetyl)morpholine (1.0 Wt, 1.00 eq) was added while maintaining the internal temperature between 10-20° C. After the addition, the mixture was stirred between 10-20° C. for 1 h and monitored the reaction for complete consumption of 4-(chloroacetyl) morpholine (target >98% conversion). The reactor was charged with water (3.0 V) and MTBE (6.00 V) while maintaining the internal temperature between 10-20° C. The biphasic mixture was stirred vigorously for 15 minutes, and then allowed to partition. The aqueous layer was extracted with MTBE (3.0 V). The combined organic layers were washed with water twice (1.5V each). The water wash was extracted with MTBE twice (1.6 V each). The organic layers were combined and concentrated under reduced pressure (T<40° C.). Heptane (1.0 V) and MTBE (1.0 V) were added. The solution was filtered to remove particulates, rinsing with additional heptane:MTBE as necessary to clear the product. The solution was returned to the reactor and concentrated under reduced pressure to give amide 12 (77%) as oil.

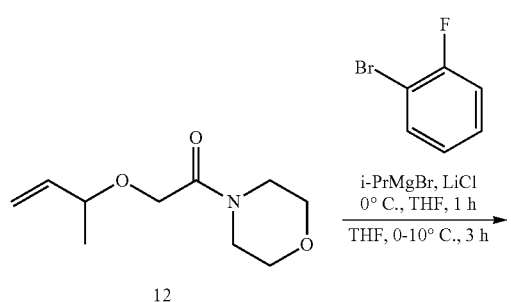

2-(But-3-en-2-yloxy)-1-(2-fluorophenyl)ethanone. A reactor was charged with 1.3 M of isopropylmagnesium chloride-lithium chloride in THF (5.15 V, 1.33 eq) and cooled to 0-5° C. 1-Bromo-2-fluorobenzene (0.726 V, 1.33 eq) was added while maintaining the internal temperature between 0-10° C. Upon complete addition, the mixture was stirred between 0-10° C. for 1 h. A solution of amide 12 (1.0 Wt, 1.0 eq.) in THF (1.0 V) was added while maintaining the internal temperature between 0-10° C. After stirring the reaction for 3 h, the reaction was monitored for complete consumption of amide 12 (>97% conversion). The reaction mixture was transferred into 1M HCl (11 V, 0.2.2 eq) while maintaining the internal temperature below 20° C. The mixture was stirred for 15 minutes and then the phases were separated. The lower aqueous layers were extracted with MTBE (5.0 V). All organic layers were combined and washed with 25 wt % aqueous sodium chloride (6.0 V). The organic phase was concentrated under reduced pressure (T<40° C.) to give ketone 8 (93%) as oil.

Example 3

Preparation of 6a-(2,3-Difluorophenyl)-4-((trityloxy) methyl) hexahydrofuro[3,4-c]isoxazole

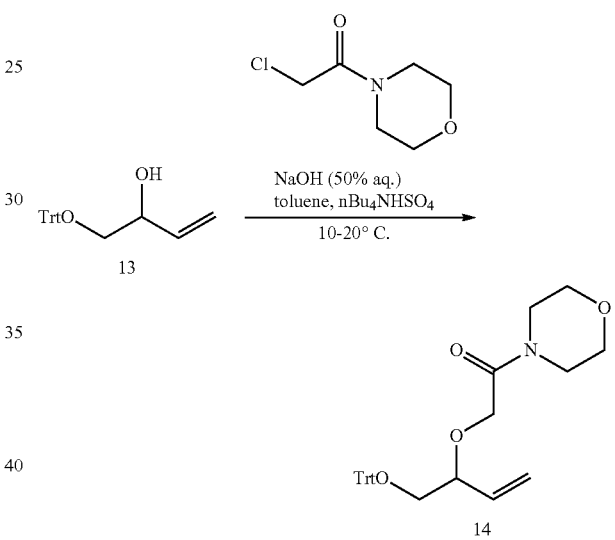

1-Morpholino-2-(1-(trityloxy)but-3-en-2-yloxy)ethanone. To a reactor with 1-(trityloxy)but-3-en-2-ol 13 (41.6 g, 0.111 mol, 1.0 equiv.) was charged toluene (146 mL). The resulting solution was cooled to 0-5° C. and tetra-n-butylammonium hydrogen sulfate (7.52 g, 0.0222 mol, 0.20 equiv.) was charged. 4-(Chloroacetyl)morpholine (18.1 g, 0.111 mol, 1.00 equiv.) was added at 0-5° C. Sodium hydroxide (50% wt. in water; 88.6 g, 1.10 mol, 10 equiv.) was cooled to 15° C. and charged to the reaction mixture with T<10° C. The reaction mixture was stirred for 1 hr at T<15° C. and monitored for consumption of 1-(trityloxy)but-3-en-2-ol (target >99%). To the reaction mixture was charged 2-methoxy-2-methylpropane (146 mL) and water (146 mL) with T<20° C. The organics were washed with 18% aq. NaCl (73 mL) and sat. aq NH4Cl (21 mL). The organics were filtered over Celite (10.4 g) to remove particulates and rinsed with 2-methoxy-2-methylpropane (83 mL). The solvents were evaporated under vacuum T<30° C. to afford a white solid 14 on standing (55.0 g, 98.7% yield accounting for residual solvents).

1-Morpholino-2-(1-(trityloxy)but-3-en-2-yloxy)ethanone: $^1$H NMR (500 MHz, CDCl$_3$) δ 7.46-7.41 (m, 6H), 7.32-7.25 (m, 6H), 7.25-7.18 (m, 3H), 5.79-5.68 (m, 1H), 5.28 (d, J=17.0 Hz, 1H), 5.26 (d, J=10.1 Hz, 1H), 4.20 (d, J=12.7 Hz, 1H), 4.10 (d, J=12.7 Hz, 1H), 3.97-3.88 (m, 1H), 3.69-3.47 (m, 8H), 3.25 (dd, J=9.9, 6.5 Hz, 1H), 3.17 (dd, J=9.9, 4.3 Hz, 1H); $^{13}$C NMR (125 MHz, CDCl$_3$) δ 167.84, 143.84, 134.84, 128.67, 127.78, 127.04, 119.06, 86.73, 81.07, 68.78, 66.78, 66.34, 45.94, 42.16.

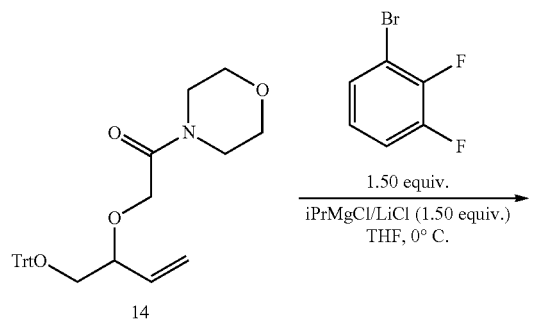

1-(2,3-Difluorophenyl)-2-(1-(trityloxy)but-3-en-2-yloxy)ethanone.

Isopropylmagnesiumchloride-LiCl complex (1.30 M in THF, 155.0 mL, 0.0715 mol) under nitrogen was cooled to 0-5° C., and 2,3-difluorobromobenzene (13.8 g, 0.0715 mol, 1.50 equiv.) was added while T<10° C. After 1 h at 0-5° C., a solution of 1-morpholino-2-(1-(trityloxy)but-3-en-2-yloxy)ethanone 14 (21.8 g, 0.048 mol, 1.0 equiv.) in THF (2.0 vols) was added while T<10° C. The reaction mixture was stirred for 2.5 hours and monitored for consumption of 1-morpholino-2-(1-(trityloxy)but-3-en-2-yloxy)ethanone (target >97%). The reaction mixture was quenched by charging into cold sat. aq. NH$_4$Cl (110 mL) and water (33 mL) while T<20° C. 2-Methoxy-2-methylpropane (218 mL) was added and the layers were separated. The organics were washed with sat. aq. NH$_4$Cl (65 mL) and 18% aq. NaCl (44 mL.). The organics were concentrated under vacuum T<25° C. to a light yellow oil of ketone 15 (21.6 g).

1-(2,3-Difluorophenyl)-2-(1-(trityloxy)but-3-en-2-yloxy)ethanone: $^1$H NMR (500 MHz, CDCl$_3$) δ 7.70-7.64 (m, 1H), 7.47-7.42 (m, 6H), 7.37-7.30 (m, 1H), 7.30-7.25 (m, 6H), 7.24-7.19 (m, 3H), 7.19-7.13 (m, 1H), 5.84-5.71 (m, 1H), 5.30 (d, J=17.3 Hz, 1H), 5.25 (d, J=10.4 Hz, 1H), 4.78 (dd, J=17.7, 3.1 Hz, 1H), 4.70 (dd, J=17.7, 3.1 Hz, 1H), 4.03 (dd, J=11.8, 6.5 Hz, 1H), 3.35 (dd, J=9.8, 6.4 Hz, 1H), 3.18 (dd, J=9.8, 4.6 Hz, 1H); $^{13}$C NMR (125 MHz, CDCl$_3$) δ 194.15 (dd, J$_{CF}$=4.9, 2.4 Hz), 150.77 (dd, J$_{CF}$=250.3, 14.1 Hz), 150.29 (dd, J$_{CF}$=256.4, 13.9 Hz), 143.98, 135.34, 128.75, 127.76, 126.95, 125.70 (d, J$_{CF}$=12.0 Hz), 125.16 (d, J$_{CF}$=3.5 Hz), 124.55 (dd, J$_{CF}$=6.4, 4.2 Hz), 121.62 (d, J$_{CF}$=17.6 Hz), 118.83, 86.78, 81.35, 74.98 (d, J$_{CF}$=9.5 Hz), 66.71.

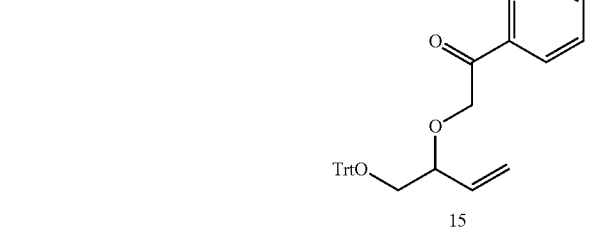

1-(2,3-Difluorophenyl)-2-(1-(trityloxy)but-3-en-2-yloxy)ethanone oxime. To a solution of 1-(2,3-difluorophenyl)-2-(1-(trityloxy)but-3-en-2-yloxy)ethanone 15 (21.1 g, 0.0435 mol, 1.0 equiv.) in MeOH (106 mL) was added NaOAc (5.36 g, 0.0653 mol, 1.50 equiv.) at ambient temperature. After 5 min., NH$_2$OH HCl (3.33 g, 0.048 mol, 1.10 equiv.) was added in portions. The suspension was warmed to 35° C. and stirred for 1 hour. The reaction mixture was cooled to 17.8° C. and stirred for 15 minutes, then filtered and rinsed with ethyl acetate (84 mL). The filtrates were concentrated under vacuum (T<30° C.). To the resulting residue was charged 2-methoxy-2-methylpropane (169 mL) and water (21.1 mL). The organics were washed with sat. aq. NaHCO$_3$ (53 mL) and 18% aq. NaCl (21 mL). The organics were concentrated under vacuum to afford the title compound 16 as an oil (21.0 g).

1-(2,3-Difluorophenyl)-2-(1-(trityloxy)but-3-en-2-yloxy)ethanone oxime: $^1$H NMR (500 MHz, CDCl$_3$) δ 7.42-7.32 (m, 6H), 7.30-7.15 (m, 10H), 7.16-7.06 (m, 1H), 7.03-6.95 (m, 1H), 5.72-5.58 (m, 1H), 5.24-5.13 (m, 2H), 4.80 (d, J=14, 6 Hz, 1H), 4.73 (d, J=14.6 Hz, 1H), 4.45 (d, J=12.4 Hz, 0.3H), 4.35 (d, J=12.4 Hz, 0.3H), 3.99-3.91 (m, 0.3H), 3.91-3.83 (m, 1H), 3.20 (dd, J=9.9, 6.8 Hz, 0.3H), 3.09 (dd, J=9.8, 6.6 Hz, 1H), 3.02 (dd, J=9.9, 4.2 Hz, 0.3H), 2.95 (dd, J=9.8, 4.0 Hz, 1H); $^{13}$C NMR (125 MHz, CDCl$_3$) δ 155.40, 150.59 (dd, J$_{CF}$=248.1, 13.0 Hz), 148.86 (dd, J$_{CF}$=252.6, 13.5 Hz), 143.96, 135.10, 128.73, 128.69, 127.72, 127.68, 126.92, 126.85, 124.96, 124.56 (d, J$_{CF}$=10.6 Hz), 124.03-123.86 (m), 118.64 (d, J$_{CF}$=15.1 Hz), 117.92 (d, J$_{CF}$=17.2 Hz), 86.66, 86.50, 81.30, 80.32, 69.20, 66.54, 66.48, 62.57.

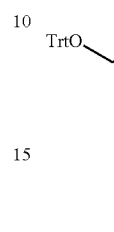

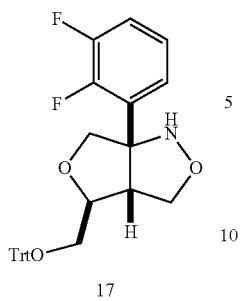

17

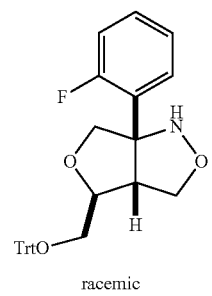

racemic 6a-(2,3-Difluorophenyl)-4-((trityloxy)methyl)hexahydrofuro[3,4-c]isoxazole. To a solution of 1-(2,3-Difluorophenyl)-2-(1-(trityloxy)but-3-en-2-yloxy)ethanone oxime 16 (20.0 g, 0.0400 mol, 1.0 equiv.) in toluene (140 mL) was charged hydroquinone (0.0882 g, 0.008 mol, 0.2 equiv.). The reaction mixture was heated to reflux (110-115° C.) and held for 13 hours. The reaction mixture was cooled to 20-25° C. and then concentrated under vacuum (T<45° C.). The solvents were chased with 2-propanol (100 mL). To the crude residue was charged isopropanol (140 mL) and the mixture was heated to 65-70° C. until a clear solution is formed. The solution was cooled to 0° C. at 10° C./hr and then held for 1 hour. The resulting suspension was filtered and the solid was rinsed with cold 2-propanol (40.0). After drying the title compound 17 was obtained as a powder (13.2 g).

6a-(2,3-Difluorophenyl)-4-((trityloxy)methyl)hexahydrofuro[3,4-c]isoxazole: $^1$H NMR (500 MHz, DMSO) δ 7.42-7.33 (m, 8H), 7.31 (t, J=7.6 Hz, 6H), 7.28-7.21 (m, 3H), 7.20-7.12 (m, 1H), 639 (s, 1H), 4.13 (d, J=8.2 Hz, 1H), 4.03 (s, 1H), 3.97 (s, 1H), 3.89 (d, J=9.2 Hz, 1H), 3.81-3.70 (m, 1H), 3.36-3.29 (m, 1H), 3.26 (dd, J=10.1, 6.0 Hz, 1H), 3.15 (dd, J=10.0, 3.5 Hz, 1H); $^{13}$C NMR (125 MHz, DMSO) δ 150.74 (dd, $J_{CF}$=246.4, 14.4 Hz), 148.66 (dd, $J_{CF}$=248.3, 13.5 Hz), 144.09, 130.58, 128.67, 128.32, 127.48, 124.75, 124.45, 117.18 (d, $J_{CF}$ 17.0 Hz), 86.57, 84.91, 78.16, 76.81, 64.82, 56.46.

Example 4

Preparation of 6a-(2-fluorophenyl)-4-((trityloxy)methyl)hexahydrofuro[3,4-c]isoxazole

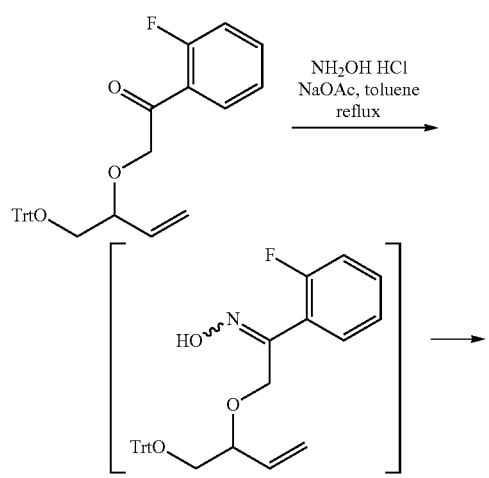

6a-(2-fluorophenyl)-4-((trityloxy)methyl)hexahydrofuro[3,4-c]isoxazole. A reactor was charged with 1-(2-fluorophenyl)-2-((1-(trityloxy)but-3-en-2-yl)oxy)ethanone (61.2 g, 1.0 equiv), toluene (428 mL) and sodium acetate (16.1 g, 1.5 equiv). Upon complete addition, the reaction mixture was stirred at ambient temperature for 5 minutes. Hydroxylamine hydrochloride (10.0 g, 1.1 Eq) was added and the suspension was heated to 111° C. After stirring for >20 hours at 111° C., the reaction mixture was allowed to cool down to ambient temperature, and the suspension was filtered and the solids rinsed with toluene (245 mL) and then THF (10 volumes) The filtrate was concentrated under reduced pressure (bath temp. ≤40° C.) and chased with 2-propanol (275 mL). 2-Propanol (428 mL) was added to the solids and the suspension was heated to 83° C. After stirring for 1 hour at 83° C., the mixture was allowed to cool down to ambient temperature. The slurry was cooled to 0° C. over a 1 hour period and stirred at 0° C. for 1 hour. The suspension was filtered and the solids rinsed in two portions with cold 2-propanol (490 mL) to give 6a-(2-fluorophenyl)-4-((trityloxy)methyl)hexahydrofuro[3,4-c]isoxazole (42.3 g) as a solid.

$^1$H NMR (400 MHz, CDCl$_3$) δ 7.62 (t, 1H), 7.41 (d, J=7.2 Hz, 6H), 7.31-7.21 (m, 10H), 7, 12 (m, 1H), 7.03 (dd, J=12.0, 8.0 Hz, 1H), 4.29-4.04 (m, 3H), 3.91 (dd, J=8.8, 1.2 Hz, 1H), 188 (m, 1H), 3.42 (dd, J=9.2, 6.8 Hz, 1H), 3.29 (m, 1H), 3.22 (dd, J=10.0, 4.8 Hz, 1H).

B. Preparation of Tetrahydrofurans of Formula II

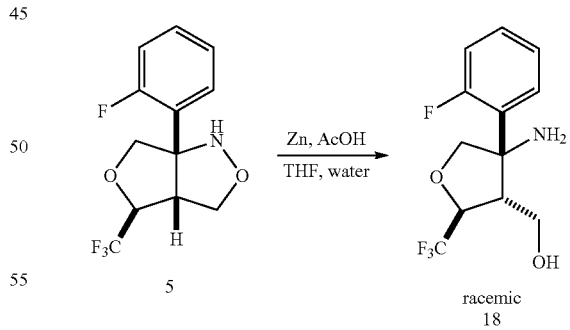

racemic
18

4-Amino-4-(2-fluorophenyl)-2-(trifluoromethyl)tetrahydrofuran-3-yl)methanol. Zinc (389.2 g, 5.95 mol) was placed in a reaction vessel, and water was added (893 mL). Acetic acid was added while maintaining the temperature below 10° C. After 15 min, 6a-(2-fluorophenyl)-4-(trifluoromethyl)hexahydrofuro[3,4-c]isoxazole 5 (550.0 g, 1.98 mol) was added as a solution in THF (665 mL). The reaction mixture was stirred over 16 h at rt. Methylene chloride (1.89 L) was added, followed by 28% aq. NH$_4$OH (552 mL) while the temperature was kept below 30° C. The mixture was stirred for 30 min, and then filtered over Celite (80 g) rinsing with methylene chloride (378 mL). The aq. layer was extracted with methylene chloride (1.89 L). The organics were combined, washed with sat. aq. NaCl (1.0 L) and concentrated under vacuum to afford an aminoalcohol 18 (502 g, 90.6%). The crude residue was used in the following step without additional purification.

HRMS Calculated for $C_{12}H_{13}F_4NO_2$ [M+H]$^+$ 280.0961. found 280.0972.

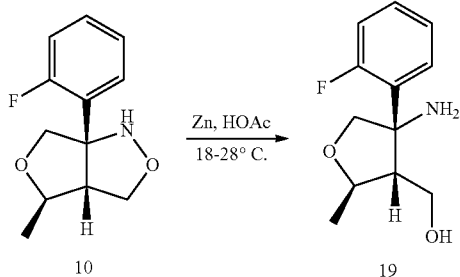 [SMILES: C[C@H]1OC[C@]2(c3ccccc3F)NOC[C@H]12 ; C[C@H]1OC[C@@](N)(c2ccccc2F)[C@@H]1CO]

4-Amino-4-(2-fluorophenyl)-2-methyltetrahydrofuran-3-yl) methanol. A reactor was charged with tetrahydroisoxazole 10 (1.0 Wt, 1.0 eq) and glacial acetic acid (4.1 Wt, 6.0 V). The mixture was stirred at 20° C., then in 3 portions, gradually charged zinc dust (1.17 Wt, 4.0 eq.) keeping the reaction temperature below 60° C. Once the exotherm subsided, the mixture was stirred at 40° C. for 2 h and then monitored for complete consumption of tetrahydroisoxazole 10 (>99% conversion). The mixture was filtered to remove residual zinc. The reactor and solids were rinsed with ethyl acetate (4.5 Wt, 5 V). The filtrate was returned to the reactor a concentrated under reduced pressure (T<40° C.). Toluene (1.73 wt, 2.0 V) was charged and the mixture was concentrated under reduced pressure. Toluene (1.73 wt, 2.0 V) was charged and the mixture was concentrated under reduced pressure. Dichloromethane (6.81 wt, 5 V) and water (5.0 wt, 5.0 vol) were charged. Add 28% ammonium hydroxide until the pH reaches 8-9. The mixture was stirred for 15 minutes, then the phases were allowed to separate and the lower organic layer removed. Charged dichloromethane (5.4 wt, 4.0 V). Stirred the mixture for 15 minutes then separated the phases. The organic phases were combined then washed with 25% aqueous sodium chloride (2.0 Wt, 2.0V). The organic phase was concentrated under reduced pressure (T<40° C.). Anhydrous THF (2.0 Wt) was added, and the solution was filtered to remove particulates, rinsing with additional anhydrous THF as necessary to clear the product. The THF solution was returned to the reactor and concentrated under reduced pressure to give aminoalcohol 19 (0.93 Wt, 94.0%) as an oil.

4-Amino-4-(2-fluorophenyl)-2-methyltetrahydrofuran-3-yl)methanol: $^1$H NMR (500 MHz, DMSO) δ 7.63 (td, J=8.6, 1.7 Hz, 1H), 7.32-7.24 (m, 1H), 7.20-7.08 (m, 2H), 4.43 (s, 1H), 4.07 (dd, J=8.7, 1.3 Hz, 1H), 4.02 (dq, J=8.5, 6.1 Hz, 1H), 3.68-3.57 (m, 2H), 3.55-3.46 (m, 1H), 2.23 (dd, J=14.4, 6.7 Hz, 1H), 1.24 (d, J=6, 1 Hz, 3H); $^{13}$C NMR (125 MHz, DMSO) δ 160.69 (d, $J_{CF}$=244.7 Hz), 133.57 (d, $J_{CF}$=11.3 Hz), 128.95 (d, $J_{CF}$=8.8 Hz), 128.81 (d, $J_{CF}$=4.8 Hz), 124.33 (d, $J_{CF}$=3.2 Hz), 116.32 (d, $J_{CF}$=23.5 Hz), 79.58 (d, $J_{CF}$=4.9 Hz), 78.52, 63.99 (d, $J_{CF}$=3.5 Hz), 59.39, 56.91 (d, $J_{CF}$=2.2 Hz), 21.37.

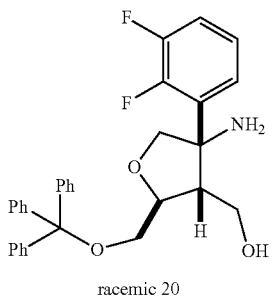

racemic 20

4-Amino-4-(2,3-difluorophenyl)-2-((trityloxy)methyl)tetrahydrofuran-3-yl)methanol. To 6a-(2,3-difluorophenyl)-4-((trityloxy)methyl)hexahydrofuro[3,4-c]isoxazole 17 (87.5 g, 0.175 mol, 1.0 equiv.) was added acetic acid (385 mL). The suspension was cooled to 15° C., and zinc (88.4 g, 1.35 mol, 7.71 equiv.) was added in small portions over 2-3 min. The reaction was allowed to warm up to 18° C. over 3-4 hours and stirred for 9 h. The reaction was filtered over celite (40 g) and rinsed with toluene (210 mL). The collected filtrate was concentrated under reduced pressure with bath temperature below 35° C. and chased with three portions of toluene (3×130 mL). The resulting oil was dissolved in $CH_2Cl_2$ (320 mL). Water (195 mL) was added followed by 28% $NH_4OH$ (43.4 mL). The organic layer was separated and the remaining aqueous phase was extracted with $CH_2Cl_2$ (130 mL). The combined organic phases were washed with 27% aq. NaCl (87.5 mL). The solution was concentrated under reduced pressure, dissolved in THF (270 mL) and filtered through celite. The solids were rinsed with THF (130 mL) and the combined filtrate was concentrated under vacuum to produce title compound 20 (69.1 g) as a foam.

4-Amino-4-(2,3-difluorophenyl)-2-((trityloxy)methyl)tetrahydrofuran-3-yl)methanol: $^1$H NMR (500 MHz, DMSO) δ 7.47 (t, J=7.5 Hz, 1H), 7.41 (d, J=7.5 Hz, 6H), 7.34-7.27 (m, 7H), 7.28-7.21 (m, 3H), 7.19-7.10 (m, 1H), 4.14 (d, J=8.7 Hz, 1H), 4.15-4.09 (m, 1H), 3.77 (dd, J=8.6, 2.6 Hz, 1H), 3.59 (dd, J=11.1, 6.4 Hz, 1H), 3.46 (dd, J=11.1, 6.6 Hz, 1H), 3.18 (dd, J=9.9, 3.0 Hz, 1H), 3.07 (dd, J=9.9, 5, 8 Hz, 1H), 2.62 (dd, J=14.6, 6.6 Hz, 1H); $^{13}$C NMR (125 MHz, DMSO) δ 150.68 (dd, $J_{CF}$=244.4, 13.9 Hz), 148.46 (dd, $J_{CF}$=246.7, 13.0 Hz), 144.36, 135.44 (d, $J_{CF}$=8.1 Hz), 128.76, 128.23, 127.37, 124.31, 124.23, 116.12 (d, $J_{CF}$=17.1 Hz), 86.29, 81.48, 78.92 (d, $J_{CF}$=4.3 Hz), 66.03, 63.93, 59.49, 51.27

HRMS Calculated for $C_{31}H_{29}F_2NO_3$ [M+Na]$^+$ 524.2013. found 524.2039.

Alternative Procedure for the Preparation of Compounds of Formula II

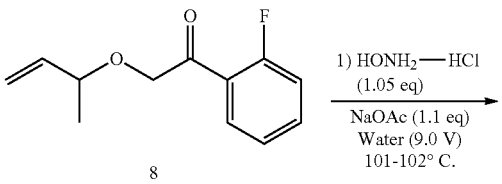

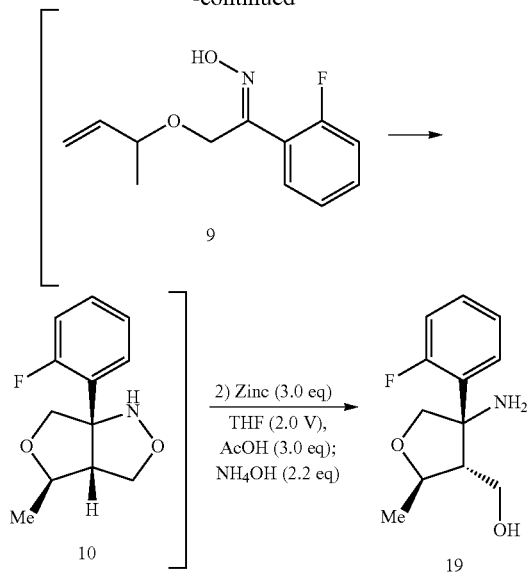

4-Amino-4-(2-fluorophenyl)-2-methyltetrahydrofuran-3-yl)methanol (19).

A reactor was charged with ketone 8 (1.0 Wt, 1.0 eq), and water (10 Wt, 10 V), hydroxylamine hydrochloride (0.350 Wt, 1.05 eq) and sodium acetate (0.433 Wt, 1.10 eq), were added. The resulting mixture was stirred and warmed to between 101-102° C. for at least 40 h and monitored for complete conversion to tetrahydrooxazole 10 (>95%). The mixture was cooled to below 25° C. and then charged with THF (1.8 wt, 2.0V) and acetic acid (0.86 Wt, 0.82 V, 3.0 eq). Zinc dust (0.942 Wt, 3.00 eq) was added while maintaining the internal temperature below 45° C. The resulting mixture was stirred between 35-45° C. for 1 h and the reaction was monitored for complete conversion to aminoalcohol 19 (>99%). The mixture was cooled to below 20° C. and dichloromethane (2.6 Wt, 2.0 V) was added. Aqueous ammonium hydroxide (28%; 1.3 wt, 1.5 V, 2.2 eq) was added until the pH reached 10-12. The resulting mixture was stirred for 15 minutes and the solids were then filtered, rinsing with dichloromethane (4.6 Wt, 3.5V). After allowing the filtrate layers to partition, the lower organic layer was set aside. The upper aqueous layer was extracted twice with dichloromethane (2.6 wt, 2.0 V each). The combined organic layers were concentrated under reduced pressure (jacket T<45° C.) to give aminoalcohol 19 (0.88 wt, 81%).

C. Diastereomeric Resolution of Tetrahydrofurans of Formula II

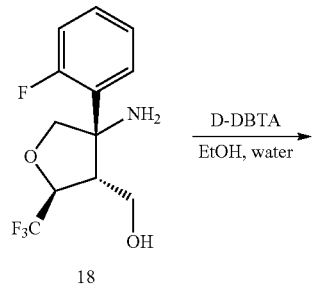

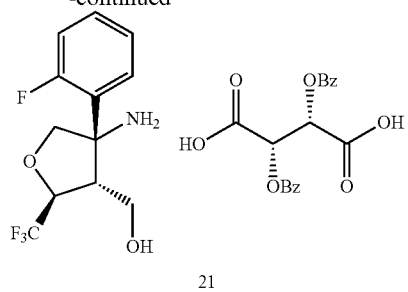

((2S,3R,4S)-4-Amino-4-(2-fluorophenyl)-2-(trifluoromethyl)tetrahydrofuran-3-yl)methanol (2S,3S)-2,3-bis(benzoyloxy)succinate. To a solution of 4-amino-4-(2-fluorophenyl)-2-(trifluoromethyl)tetrahydrofuran-3-yl)methanol 18 (0.502 kg, 1.798 mol) in ethanol (4.865 L) was added dibenzoyl-D-tartaric acid (0.642 kg, 1.798 mol). The resulting suspension was heated to 67° C. Water (94.0 mL, 5.2 mol) was added over 15 min while maintaining temperature >66° C. The resulting solution was cooled to 45° C. while precipitation occurred. The slurry was reheated to 60° C., and then cooled to ambient temperature at 5° C./hour. The slurry was filtered, and the solid was rinsed with premixed and cooled solution of ethanol (950 mL) and water (20 mL). The solid aminoalcohol dibenzoyltartaric acid salt 21 was dried until constant weight under vacuum (370 g, 97.6% ee).

((2S,3R,4S)-4-Amino-4-(2-fluorophenyl)-2-(trifluoromethyl)tetrahydrofuran-3-yl)methanol (2S,3S)-2,3-bis(benzoyloxy)succinate: $^1$H NMR (500 MHz, CD$_3$OD) δ 8.13 (d, J=7.2 Hz, 4H), 7.66-7.58 (m, 3H), 7.54-7.45 (m, 5H), 7.36-7.20 (m, 2H), 5.92 (s, 2H), 4.79-4.66 (m, 1H), 4.40-4.28 (m, 1H), 4.04 (dd, J=12.1, 3.4 Hz, 1H), 3.92 (dd, J=12.1, 5.4 Hz, 1H), 3.30-3.24 (m, 1H); $^{13}$C NMR (125 MHz, DMSO) δ 169.61, 165.81, 160.23 (d, J=246.1 Hz), 133.00, 131.34 (d, J=9.1 Hz), 129.65, 129.55, 128.08, 127.97 (d, J=3.5 Hz), 124.95 (d, J=3.3 Hz), 116.56 (d, J=23.5 Hz), 77.48 (q, J$_{CF}$=31.0 Hz), 76.33, 73.20, 65.61 (d, J=31 Hz), 57.11.

HRMS Calculated for C$_{12}$H$_{13}$F$_4$NO$_2$ [M+H]$^+$ 280.0961. found 280.0967 (for amino alcohol).

The absolute stereochemistry of the amino alcohol 21 was assigned by comparison with a sample prepared starting from enantioenriched (S)-2-(trifluoromethyl)oxirane.

Chiral HPLC Parameters:

Equipment, Reagents, and Mobile Phase:

Equipment:

| | |
|---|---|
| HPLC column: | Chiralcel OD, 4.6 × 250 mm, 10 μm, Daicel Chemical Industries, Ltd., catalog no. 14025. |
| Solvent Delivery System: | Agilent 1100 HPLC ternary pump, low pressure mixing with in-line degasser, or equivalent. |
| Autosampler: | Agilent 1100 autosampler, 0.1 to 100 μL range, or equivalent. |
| Detector: | Agilent 1100 variable wavelength detector or equivalent. |
| Chromatographic Software: | Agilent ChemStation software version A.09.03 or higher for HPLC, Waters Empower 2 Build 2154 or equivalent. |
| Volumetric Glassware: | Class A. |
| Volumetric pipette: | Class A. |
| Pipettor: | Calibrated Eppendorf adjustable volume, or equivalent. |
| Balance: | Analytical balance, capable of weighing ± 0.1 mg. |

Reagents:

| | |
|---|---|
| Heptane: | HPLC grade, Baker (catalog no. 9177-03) or equivalent. |
| 2-Propanol: | HPLC grade, Baker (catalog no. 9095-03) or equivalent. |
| Triethylamine: | ≥99%, Sigma-Aldrich (catalog no. T0886) or equivalent. |

Mobile Phase:

Add 70 mL 2-propanol and 930 mL heptane (measured separately with a 100 mL and 1000-mL graduated cylinders) and 1.0 mL triethylamine (measured with volumetric glass pipette) to an appropriate flask and mix. Degas in-line during use.

Diluting Solution: 2-Propanol

HPLC Parameters:

| | |
|---|---|
| HPLC column: | Chiralcel OD, 4.6 × 250 mm, 10 μm, Daicel Chemical Industries, Ltd., catalog no. 14025. |
| Temperature: | 35° C. |
| Flow rate*: | 0.8 mL/min |
| Gradient: | NA |
| Injection Volume: | 5 μL |
| Detection: | 262 nm UV |
| Data acquisition time: | 30 min |
| Total run time: | 30 min |
| Column Maximum Pressure: | 35 Bar |
| Needle Wash: | 2-propanol |

*Flow rate may be adjusted ± 0.2 ml/min to obtain specified retention times.

Retention Times for Analytes and Impurities:

| Compound Peak | Retention Time (Relative Retention Time, RRT) |
|---|---|
| 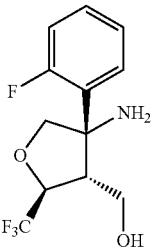 [SMILES: N[C@@]1(c2ccccc2F)CO[C@H](C(F)(F)F)[C@H]1CO] | 20.6 min ± 10% (RRT 1.00) |
| 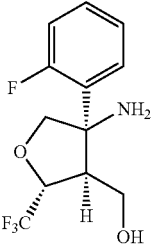 [SMILES: N[C@]1(c2ccccc2F)CO[C@@H](C(F)(F)F)[C@@H]1CO] (Enantiomer) | 19.2 min (RRT 0.93) |

A typical chromatogram is presented in FIG. 1A.

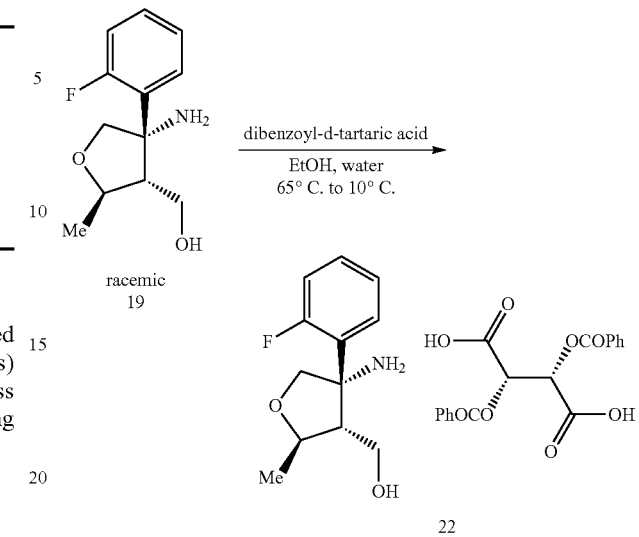

((2R,3R,4S)-4-Amino-4-(2-fluorophenyl)-2-methyltetrahydrofuran-3-yl)methanol (2S,3S)-2,3-bis(benzoyloxy)succinate. A reactor was charged with aminoalcohol 19 (1.0 Wt, 1.0 eq) and ethanol (5.5 Wt, 7.0 V). The mixture was heated to internal temperature 65-70° C. To the mixture is added a solution of dibenzoyl-D-tartaric acid (1.0 eq, 1.59 wt) in ethanol (1.97 Wt, 2.50 V) and water (0.25 Wt, 0.25V) over 30-60 minutes while maintaining the internal temperature above 60° C. The vessel containing the dibenzoyltartaric acid was rinsed with minimum amount ethanol. The mixture was then cooled to 40° C. at a rate 3° C./hour. After crystallization the mixture was cooled to 10° C. (at 10° C./hour) and stirred for at least 2 hours at 10° C. The crystals were then filtered and rinsed with pre-chilled ethanol (1.4 Wt, 1.8 V) and dried under vacuum to give amino alcohol dibenzoyltartaric acid salt 22 (0.86 Wt, 33.0%) as solid.

((2R,3R,4S)-4-Amino-4-(2-fluorophenyl)-2-methyltetrahydrofuran-3-yl)methanol (2S,3S)-2,3-bis(benzoyloxy)succinate: $^1$H NMR (500 MHz, CD$_3$OD) δ 8.14-8.10 (m, 4H), 7.60 (t, J=7.4 Hz, 2H), 7.55 (td, J=8.1, 1.3 Hz, 1H), 7.47 (t, J=7.8 Hz, 4H), 7.46-7.42 (m, 1H), 7.30-7.19 (m, 2H), 5.90 (s, 2H), 4.39-4.26 (m, 2H), 4.15 (dd, J=10.4, 2.4 Hz, 1H), 3.90 (ddd, J=28.3, 11.9, 5.0 Hz, 2H), 2.52 (dt, J=8.4, 5.0 Hz, 1H), 1.31 (d, J=6.1 Hz, 3H); $^{13}$C NMR (126 MHz, CD$_3$OD) δ 169.96, 165.90, 160.35 (d, J=245.9 Hz), 132.95, 131.05 (d, J$_{CF}$=9.1 Hz), 129.75, 129.57, 128.06, 127.57 (d, J$_{CF}$=3.5 Hz), 124.82 (d, J$_{CF}$=3.2 Hz), 124.24 (d, J$_{CF}$=11.5 Hz), 116.45 (d, J$_{CF}$=23.1 Hz), 76.34, 74.32 (d, J$_{CF}$=5.4 Hz), 73.50, 65.60 (d, J$_{CF}$=2.8 Hz), 57.43, 54.88, 19.00.

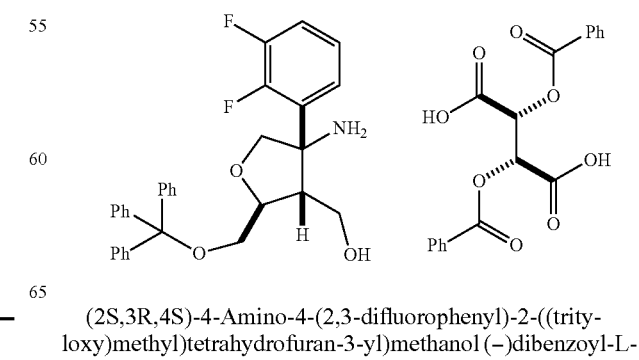

(2S,3R,4S)-4-Amino-4-(2,3-difluorophenyl)-2-((trityloxy)methyl)tetrahydrofuran-3-yl)methanol (−)dibenzoyl-L- tartaric acid. Racemic mixture 6a-(2,3-difluorophenyl)-4-((trityloxy)methyl)hexahydrofuro[3,4-c]isoxazole 20 (69.1 g, 0.138 mol, 1.0 equiv.) and (−)-dibenzoyl-L-tartaric acid (49.4 g, 0.138 mol, 1.0 equiv) were dissolved in acetone (346 mL). The mixture was then heated to 61.9° C. over 15 min. Toluene (415 mL) was added. The solution was then allowed to cool to room temperature. Then the reaction mixture was cooled to −5° C. and stirred for another hour at this temperature. The suspension was filtered and washed with a solution of toluene/acetone (V/V 6/5, 138 mL, cooled to 0° C.). The solid was dried under reduced pressure, and the title compound 23 (44.5 g) was isolated.

(2S,3R,4S)-4-Amino-4-(2,3-difluorophenyl)-2-((trityloxy)methyl)tetrahydrofuran-3-yl)methanol (−)dibenzoyl-L-tartaric acid: $^1$H NMR (500 MHz, DMSO) δ 8.00-7.95 (m, 4H), 7.66 (t, J=7.4 Hz, 2H), 7.53 (t, J=7.8 Hz, 4H), 7.47-7.39 (m, 2H), 7.40-7.35 (m, 6H), 7.35-7.28 (m, 6H), 7.28-7.23 (m, 3H), 7.23-7.15 (m, 1H), 5.75 (s, 1H), 4.19 (d, J=9.5 Hz, 2H), 4.02 (dd, J=9.5, 2.1 Hz, 1H), 3.61 (dd, J=11.4, 6.4 Hz, 1H), 3.52 (dd, J=11.4, 6.2 Hz, 1H), 3.21-3.14 (m, 1H), 3.12-3.05 (m, 1H), 2.77 (dd, J=14.3, 6.4 Hz, 1H); $^{13}$C NMR (125 MHz, DMSO) δ 168.07, 165.23, 150.68 (dd, $J_{CF}$=245.2, 13.4 Hz), 148.27 (dd, $J_{CF}$=248.0, 13.6 Hz), 144.18, 134.09, 129.75, 129.60, 129.24, 128.70, 128.28, 127.45, 124.88, 124.20, 117.40 (d, $J_{CF}$=16.8 Hz), 86.40, 80.73, 76.73, 72.22, 65.42, 64.58, 58.63, 50.51.

HRMS Calculated for $C_{31}H_{29}F_2NO_3$ [M+Na]$^+$ 524.2013. found 524.2047.

Chiral HPLC Parameters:

Equipment, Reagents, and Mobile Phase:

Equipment:

| | |
|---|---|
| HPLC column: | Chiralpak AD, 4.6 × 250 mm, 10 μm, Daicel Chemical Industries, Ltd., catalog no. 19025. |
| Solvent Delivery System: | Agilent 1100 HPLC ternary pump, low pressure mixing with an in-line degasser, or equivalent. |
| Autosampler: | Agilent 1100 autosampler, 0.1 to 100 μL range, or equivalent. |
| Detector: | Agilent 1100 variable wavelength detector or equivalent. |
| Chromatographic Software: | Agilent ChemStation software version A.09.03 or higher for HPLC, Waters Empower 2 Build 2154 or equivalent. |
| Volumetric Glassware: | Class A. |
| Volumetric pipette: | Class A. |
| Pipettor: | Calibrated Eppendorf adjustable volume, or equivalent. |
| Balance: | Analytical balance, capable of weighing ± 0.1 mg. |

Reagents:

| | |
|---|---|
| Heptane: | HPLC grade, Baker (catalog no. 9177-03) or equivalent. |
| 2-Propanol: | HPLC grade, Baker (catalog no. 9095-03) or equivalent. |
| Triethylamine: | ≥99%, Sigma-Aldrich (catalog no. T0886) or equivalent. |

Mobile Phase:

Add 100 mL 2-propanol and 900 mL heptane (measured separately with a 100 mL and 1000-mL graduated cylinders) and 0.5 mL triethylamine (measured with volumetric glass pipette) to an appropriate flask and mix. Degas in-line during use.

Diluting Solution: 2-Propanol

HPLC Parameters:

| | |
|---|---|
| HPLC column: | Chiralpak AD, 4.6 × 250 mm, 10 μm, Daicel Chemical Industries, Ltd., catalog no. 19025. |
| Temperature: | 35° C. |
| Flow rate*: | 0.8 mL/min |
| Gradient: | NA |
| Injection volume: | 5 μL |
| Detection: | 260 nm UV |
| Data acquisition time: | 40 min |
| Total run time: | 40 min |
| Column Maximum Pressure: | 35 Bar |
| Needle Wash: | 2-propanol |

*Flow rate may be adjusted ± 0.2 ml/min to obtain specified retention times.

Retention Times for Analytes and Impurities:

| Compound Peak | Retention Time (Relative Retention Time, RRT) |
|---|---|
| (structure with F, F, NH₂, O, TrtO, H, OH) | 15.5 min ± 10% (RRT 1.00) |
| (structure, Enantiomer) | 21.5 min (RRT 1.39) |

Figure 1B:
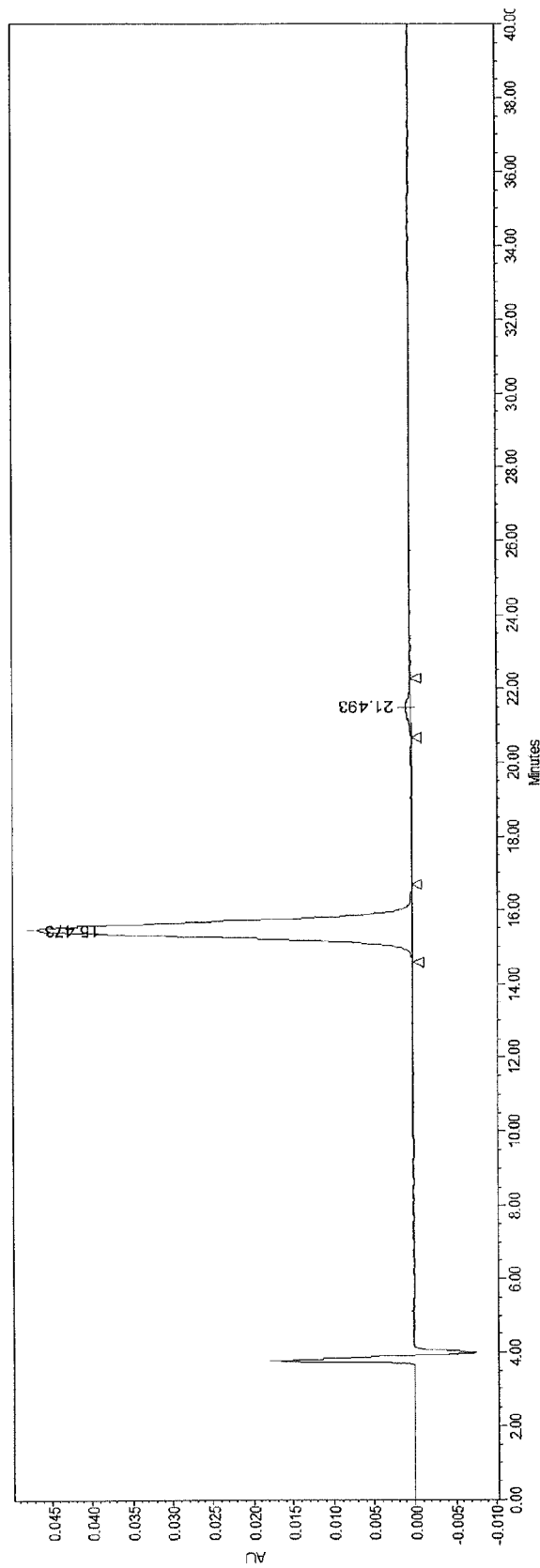

A typical chromatogram is presented in FIG. 1B.

D. Synthesis of Carbamothioyl Benzamides of Formula III

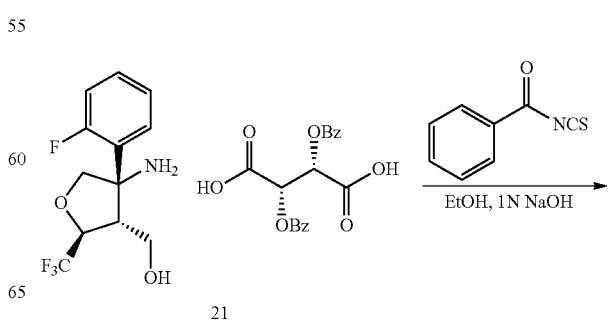

21

-continued

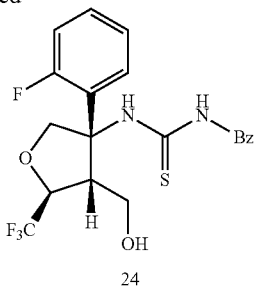

24

N-((3S,4R,5S)-3-(2-fluorophenyl)-4-(hydroxymethyl)-5-(trifluoromethyl)-tetrahydrofuran-3-ylcarbamothioyl)benzamide. To chiral salt 21 (0.361 kg, 0.556 mol) was added ethyl acetate (1.08 L) and the suspension was cooled to −3° C. 1.0 N aq. NaOH (1.30 L) was added over 20 minutes while maintaining T<5° C. After 5 minutes, benzoyl isothiocyanate (80.0 mL, 594 mmol) was added over 8 minutes while maintaining T<5° C. After 1 hr, ethyl acetate (722 mL) was charged. The aq. layer was removed, and the organics were washed with sat. aq. NaHCO$_3$ (361 mL) and sat. aq. NaCl (361 mL). The organics were filtered over celite (90 g) and rinsed with ethyl acetate (360 mL). The organics were concentrated under vacuum to afford a residue which was re-dissolved into CH$_2$Cl$_2$ (1.1 L) and concentrated to afford the title compound 24 as yellow foam (261 g, 99% yield accounting for residual solvents) which was used in the following step.

N-((3S,4R,5S)-3-(2-fluorophenyl)-4-(hydroxymethyl)-5-(trifluoromethyl)-tetrahydrofuran-3-ylcarbamothioyl)benzamide: $^1$H NMR (500 MHz, DMSO) δ 12.04 (s, 2H), 11.20 (s, 2H), 7.95 (d, J=7.4 Hz, 2H), 7.69-7.60 (m, 1H), 7.56-7.42 (m, 2H), 7.37-7.28 (m, 1H), 7.24-7.12 (m, 2H), 5.59 (t, J=4.5 Hz, 1H), 5.03 (d, J=9.7 Hz, 1H), 4.92 (d, J=9.7 Hz, 1H), 4.75-4.63 (m, 1H), 3.92-3.74 (m, 2H), 2.77-2.66 (m, 1H); $^{13}$C NMR (125 MHz, DMSO) δ 179.98, 167.85, 159.75 (d, J$_{CF}$=245.0 Hz), 133.44, 132.58, 129.88, 129.81, 129.04, 128.85, 126.31 (d, J$_{CF}$=9.8 Hz), 124.36, 116.83 (d, J$_{CF}$=23.4 Hz), 76.11 (q, J$_{CF}$=31.0 Hz). 74.37 (d, J$_{CF}$=6.1 Hz), 68.77 (d, J$_{CF}$=3.4 Hz), 57.03, 52.23.

HRMS Calculated for C$_{20}$H$_{18}$F$_4$N$_2$O$_3$S [M+H]$^+$ 441.0896. found 441.0818.

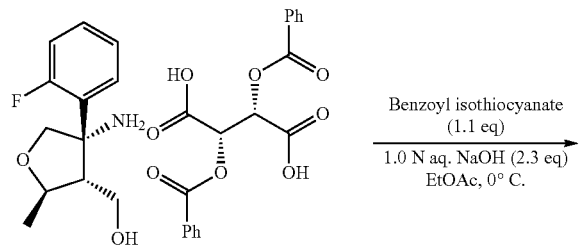

22

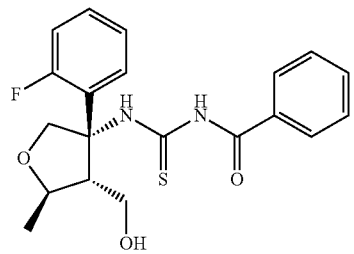

25

N-((3S,4R,5R)-3-(2-fluorophenyl)-4-(hydroxymethyl)-5-methyltetrahydrofuran-3-ylcarbamothioyl)benzamide. A reactor was charged with 22 (1 Wt, 1 eq) and ethyl acetate (2.7 Wt, 3.0 V). The mixture was cooled to 0 to 10° C. 1.00 M aqueous NaOH (4.2 Wt, 4.0 V, 2.3 eq) was added. Benzoyl isothiocyanate (0.314 Wt, 0.259 V, 1.10 eq) was added with vigorous stirring while maintaining T between 0 to 10° C. After completed addition, continued stirring at 0-5° C. over 2 h and monitored for complete consumption of 22 (target >98% conversion). The reaction mixture was filtered and the filter cake was rinsed with: 1) water (2.0 Wt, 2.0 V); 2) a mixture of heptane (0.91 Wt, 1.3V) and Ethyl acetate (1.2 Wt, 1.3 V). The solid was dried under reduced pressure (T<40° C.) to give 25 (0.57 Wt, 85.4% yield).

N-((3S,4R,5R)-3-(2-fluorophenyl)-4-(hydroxymethyl)-5-methyltetrahydrofuran-3-ylcarbamothioyl)benzamide: $^1$H NMR (500 MHz, CDCl$_3$) δ 11.78 (s, 1H), 8.88 (s, 1H), 7.88-7.82 (m, 2H), 7.67 (td, J=8.1, 1.6 Hz, 1H), 7.65-7.59 (m, 1H), 7.50 (dd, J=10.8, 4.8 Hz, 2H), 7.30-7.23 (m, 1H), 7.15 (td, J=7.8, 1.2 Hz, 1H), 7.01 (ddd, J=12.3, 8.2, 1.1 Hz, 1H), 4.73 (d, J=10.1 Hz, 1H), 4.42 (dd, J=10.1, 1.7 Hz, 1H), 4.10-4.03 (m, 1H), 4.03-3.91 (m, 2H), 2.80 (t, J=5.3 Hz, 1H), 2.63-2.52 (m, 1H), 1.35 (d, J=6.1 Hz, 3H); $^{13}$C NMR (125 MHz, CDCl$_3$) δ 179.42, 166.60, 160.35 (d, J$_{CF}$=247.4 Hz), 133.60, 131.81, 129.27 (d, J$_{CF}$=8.9 Hz), 129.20 (d, J$_{CF}$=3.7 Hz), 129.15, 127.55, 127.39 (d, J$_{CF}$=10.0 Hz), 123.96 (d, J$_{CF}$=3.3 Hz), 116.18 (d, J$_{CF}$=23.0 Hz), 76.90 (d, J$_{CF}$=2.8 Hz), 76.27, 69.26, 59.49, 58.03, 20.04.

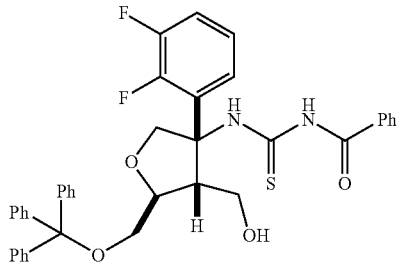

26

N-(((3S,4R,5S)-3-(2,3-difluorophenyl)-4-(hydroxymethyl)-5-((trityloxy)methyl)tetrahydrofuran-3-yl)carbamothioyl)benzamide. A suspension of chiral salt 23 (44.21 g, 0.051 mol, 1.0 equiv.) in ethyl acetate (133 mL) was cooled down to 1.7° C. Aq. NaOH (1.0 M, 121 mL, 0.12 mol, 2.4 equiv.) was added while maintaining temperature below 5° C. The reaction was stirred for 5 min then benzyl isothiocyanate (9.43 g, 0.058 mol, 1.12 equiv.) was added over 5 min. After 1.5 h, ethyl acetate (133 mL) was added. The organic phase was isolated and successively washed with saturated aq. NaHCO$_3$ (130 mL) and 18% aq. NaCl (44 mL). The combined aqueous phases were extracted with EtOAc (66 mL) and CH$_2$Cl$_2$ (30 mL). All the organic phase were combined, filtered and concentrated under reduced pressure. The title compound 26 (34.2 g) was isolated as a foam after chasing the residual solvent with CH$_2$Cl$_2$ (88 mL).

N-(((3 S,4R,5 S)-3-(2,3-difluorophenyl)-4-(hydroxymethyl)-5-((trityloxy)methyl)tetrahydrofuran-3-yl)carbamothioyl)benzamide: $^1$H NMR (500 MHz, DMSO) δ 11.97 (br s, 1H), 11.20 (br s, 1H), 7.94 (d, J=7.4 Hz, 2H), 7.63 (t, J=7.4 Hz, 1H), 7.51 (t, J=7.8 Hz, 2H), 7.38-7.21 (m, 17H), 7.13 (dd, J=13.4, 7.9 Hz, 1H), 5.13 (t, J=4.4 Hz, 1H), 5.07 (d, J=9.7 Hz, 1H), 4.47 (d, J=9.8 Hz, 1H), 4.24-4.16 (m, 1H), 3.68 (t, J=4.6 Hz, 2H), 3.19 (dd, J=10.1, 2.9 Hz, 1H), 3.01 (dd, J=10.1, 4.8

Hz, 1H), 2.63-2.52 (m, 1H); $^{13}$C NMR (125 MHz, DMSO) δ 180.06, 168.14, 150.75 (dd, $J_{CF}$=244.6, 13.2 Hz), 147.93 (dd, $J_{CF}$=247.5, 13.5 Hz), 144.15, 133.46, 132.55, 131.90 (d, $J_{CF}$=6.4 Hz), 129.04, 128.86, 128.67, 128.28, 127.43, 124.41, 124.25, 116.12 (d, $J_{CF}$=17.0 Hz), 86.27, 79.75, 75.03, 68.04, 64.63, 58.16, 53.35.

HRMS Calculated for $C_{39}H_{34}F_2N_2O_4S$ [M+H]$^+$ 663.2129. found 663.2200.

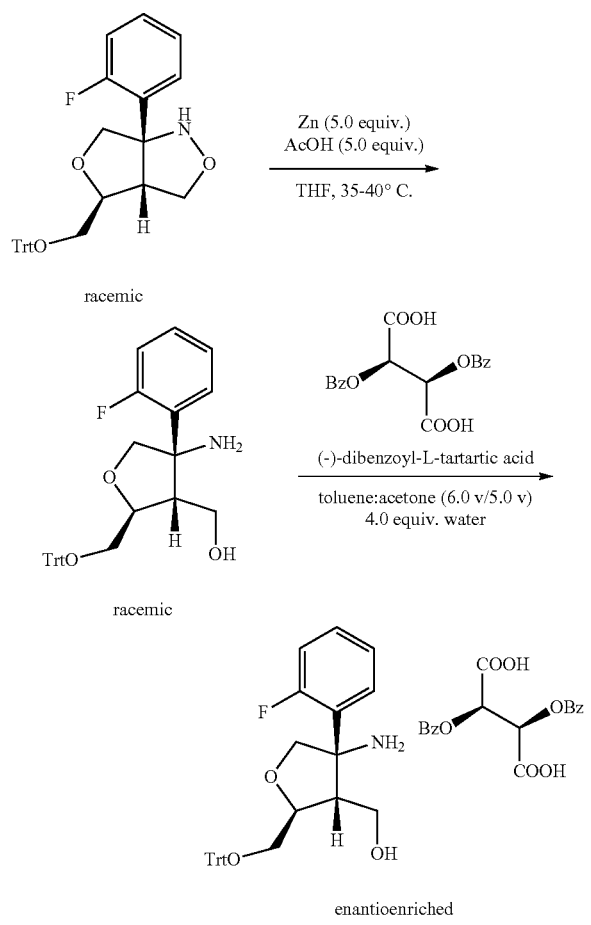

((2S,3R,4S)-4-Amino-4-(2-fluorophenyl)-2-((trityloxy)methyl)tetrahydrofuran-3-yl)methanol (2R,3R)-2,3-bis(benzoyloxy)succinate. A reactor was charged with zinc dust (<10 micron, 3.39 g 5.0 equiv.), 6a-(2-fluorophenyl)-4-((trityloxy)methyl)hexahydrofuro[3,4-c]isoxazole (5.0 g, 1.0 equiv.) and THF (30.0 mL). To the stirred suspension was charged acetic acid (2.97 mL, 5.0 equiv.). After addition, the reaction temperature was maintained between 20-30° C. for 1 hour. Then the reaction mixture was warmed to 35-40° C. and the temperature was maintained while monitoring for consumption of starting material. Upon completion, the reaction mixture was cooled to 20-25° C. and charged 28% aq NH$_4$OH (12.5 mL) while maintaining temperature <40° C. The suspension was cooled to 20-25° C. and filtered over Celite (0.5 Wts). The solids were rinsed with MTBE (35.0 mL). The filtrate was transferred to a separatory funnel. The aqueous layer was removed, and the organic layer was washed with water (10.0 mL). The organics were concentrated under vacuum (bath temperature <40° C.) to afford racemic aminoalcohol as a foam (95-105% crude yield). To the racemic amino alcohol was charged (-)-dibenzoyl-L-tartaric acid (3.74 g, 1.0 equiv). To the mixture was charged water (0.76 mL, 4.0 equiv.) and then acetone (25.3 mL). The mixture was heated to 56-60° C. and then charged toluene (30.3 mL) while maintaining temperature above 50° C. Upon completed addition, the temperature was held at 56-60° C. for at least 30 minutes and then cooled to 17-22° C. at 10° C./hour. The suspension was stirred at 17-22° C. for at least two hours. The solids were filtered and washed with a solution of toluene/acetone in two portions (6/5 VAT, 4.0 volumes). The solid was dried under reduced pressure to obtain ((2S,3R,4S)-4-Amino-4-(2-fluorophenyl)-2-((trityloxy)methyl)tetrahydrofuran-3-yl)methanol (2R,3R)-2,3-bis(benzoyloxy) succinate (3.4 g 38% yield) as a white powder. Typical ee % 96-97%.

$^1$H NMR (400 MHz, d6-DMSO) δ 7.92 (d, J=7.6 Hz, 4H), 7.61-7.54 (m, 2H), 7.46 (t, J=7.6 Hz, 4H), 7.33-7.09 (m, 19H), 5.66 (s, 2H), 4.20 (s, 1H), 4.12 (d, J=9.6 Hz, 1H), 4.07 (d, J=9.6 Hz, 1H), 3.57 (dd, J=11.2, 6.0, 1H), 3.48 (dd, J=10.8, 6.4, 1H), 3.12 (d, J=8.0 Hz, 1H), 3.03 (dd, J=10.0, 5.2 Hz, 1H), 2.77 (app q, J=7.2 Hz, 1H).

Analytical Method for Enantiomeric Excess Assessment:

HPLC Parameters:

Mobile Phase: Add 120 mL 2-propanol and 880 mL heptane (measured separately with a 100 mL and 1000-mL graduated cylinders) and 0.5 mL triethylamine (measured with volumetric glass pipette) to an appropriate flask and mix. Degas in-line during use.

| | |
|---|---|
| HPLC column: | Chiralpak AD, 4.6 × 250 mm, 10 µm, Daicel Chemical Industries, Ltd., catalog no. 19025. |
| Temperature: | 35° C. |
| Flow rate*: | 0.8 mL/min |
| Gradient: | NA |
| Injection volume: | 3 µL |
| Detection: | 260 nm UV |
| Data acquisition time: | 30 min |
| Total run time: | 30 min |
| Column Maximum Pressure: | 35 Bar |
| Needle Wash: | 2-propanol |

*Flow rate may be adjusted ± 0.2 ml/min to obtain specified retention times.

Retention Times for Analytes and Impurities;

| Compound Peak | Retention Time (Relative Retention Time, RRT) | Structure |
|---|---|---|
| ((2S,3R,4S)-4-amino-4-(2-fluorophenyl)-2-((trityloxy)methyl)tetrahydrofuran-3-yl)methanol dibenzoate diformate | 12.6 min ± 10% (RRT 1.00) | 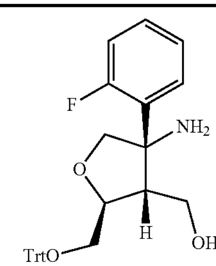 |
| Enantiomer: ((2R,3S,4R)-4-amino-4-(2-fluorophenyl)-2-((trityloxy)methyl)tetrahydrofuran-3-yl)methanol | 19.6 min (RRT 1.56) | 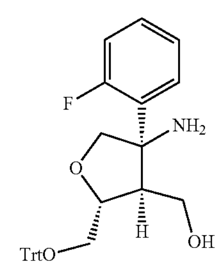 |

Figure 2:
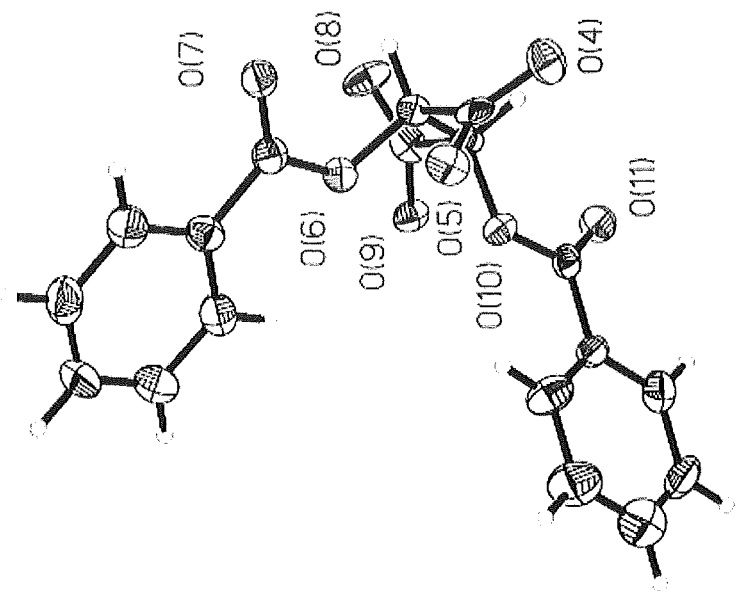
FIG. 2 presents the x-ray crystal structure of ((2S,3R,4S)-4-Amino-4-(2-fluorophenyl)-2-((trityloxy)methyl)tetrahydrofuran-3-yl)methanol (2R,3R)-2,3-bis(benzoyloxy)succinate.
Figure 2:
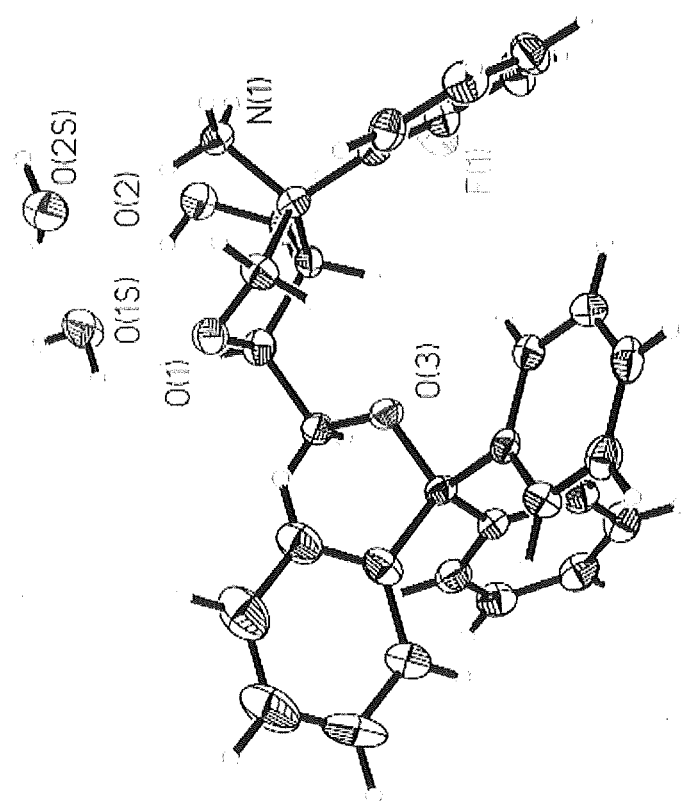

An x-ray crystal structure of ((2S,3R,4S)-4-Amino-4-(2-fluorophenyl)-2-((trityloxy)methyl)tetrahydrofuran-3-yl)methanol (2R,3R)-2,3-bis(benzoyloxy)succinate:

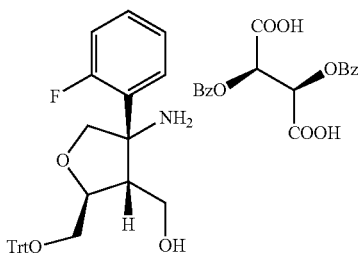

was obtained and is presented in FIG. 2.

E. Synthesis of Thiazyl Benzamides of Formula IV

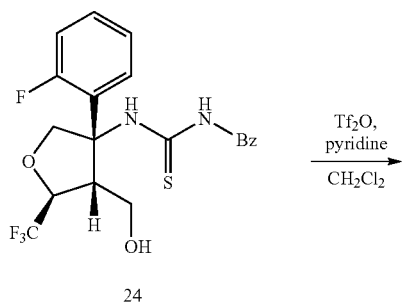

24

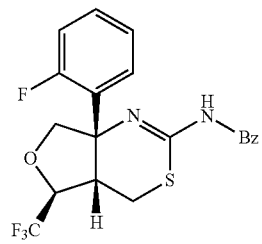

27

N-((4aS,5S,7aS)-7a-(2-fluorophenyl)-5-(trifluoromethyl)-4a,5,7,7a-tetrahydro-4H-furo[3,4-d][1,3]thiazin-2-yl)benzamide. A solution of N-((3S,4R,5S)-3-(2-fluorophenyl)-4-(hydroxymethyl)-5-(trifluoromethyl)-tetrahydrofuran-3-ylcarbamothioyl)benzamide 24 (258.3 g, 583.8 mmol) in CH$_2$Cl$_2$ (1.55 L) was cooled to −19.4° C. Pyridine (118 mL, 1.46 mol) was added while maintaining temperature at −20° C., and then the reaction mixture was cooled to −24° C. In another nitrogen purged vessel, CH$_2$Cl$_2$ (258 mL) was added followed by trifluoromethanesulfonic anhydride (108.0 mL, 642.2 mmol). The resulting solution was added to the reaction mixture over 30 min, while maintaining temperature below −19.7° C. upon completed addition, the reaction mixture was stirred for 30 min at −20° C. to −15° C., and then warmed to −11° C. over 20 min. Saturated aq. NH$_4$Cl (646 mL) and water (390 mL) was added. The mixture was warmed to ambient temperature and the aq. layer was removed. The organics were washed with premixed saturated aq. NH$_4$Cl (646 mL) and water (390 mL). The aq. layers were combined, and extracted once with CH$_2$Cl$_2$ (520 mL). The organics were combined, and concentrated under vacuum to afford 27 as a light orange foam (250 g, 100%). The residue was used in the next stage without purification.

N-((4aS,5S,7aS)-7a-(2-fluorophenyl)-5-(trifluoromethyl)-4a,5,7,7a-tetrahydro-4H-furo[3,4-d][1,3]thiazin-2-yl)benzamide: $^1$H NMR (500 MHz, CDCl$_3$) δ 8.03 (d, J=6.7 Hz, 2H), 7.52 (t, J=7.0 Hz, 1H), 7.48-7.31 (m, 4H), 7.20 (t, J=7.4 Hz, 1H), 7.12 (dd, J=12.0, 8.4 Hz, 1H), 4.82-4.73 (m, 1H), 4.60 (d, J=8.9 Hz, 1H), 4.03 (d, J=8, 3 Hz, 1H), 3.57 (d, J=2.7 Hz, 1H), 3.20 (d, J=13.6 Hz, 1H), 2.81 (dd, J=13, 8, 2.5 Hz, 1H); $^{13}$C NMR (125 MHz, CDCl$_3$) δ 171.50, 159.57 (d, J$_{CF}$=247.2 Hz), 134.62, 132.49, 130.65 (d, J$_{CF}$=8.8 Hz), 129.77, 128.51, 128.45, 125.14 (q, J$_{CF}$=281.8 Hz), 124.97 (d, J$_{CF}$=3.0 Hz), 124.66 (d, J$_{CF}$=10.3 Hz), 117.05 (d, J$_{CF}$=23.5 Hz), 66.81 (d, J$_{CF}$=5.2 Hz), 38.90, 23.20.

HRMS Calculated for C$_{20}$H$_{16}$F$_4$N$_2$O$_2$S [M+H]$^+$ 425.0947. found 425.0945.

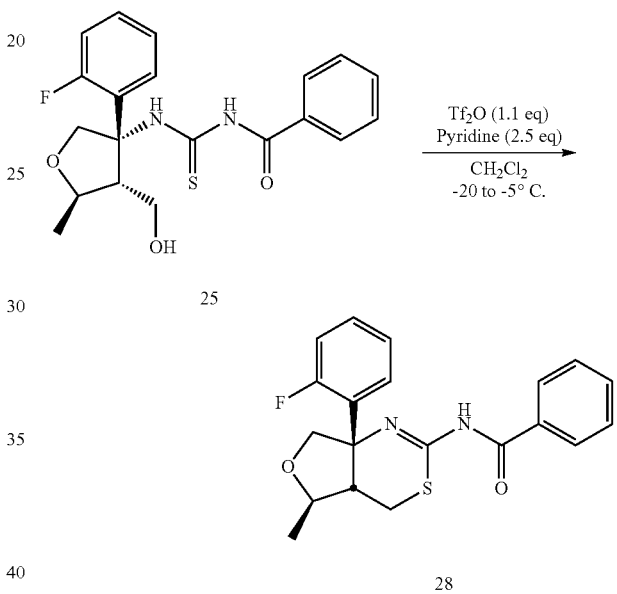

28

N-((4aS,5R,7aS)-7a-(2-fluorophenyl)-5-methyl-4a,5,7,7a-tetrahydro-4H-furo[3,4-d][1,3]thiazin-2-yl)benzamide. A reactor was charged with 25 (1 Wt, 1 eq), methylene chloride (8.0 Wt, 6.0 V) and pyridine (0.509 Wt, 0.520 V, 2.50 eq) at 18-22° C. The mixture was cooled to −20 to −15° C. A solution of trifluoromethanesulfonic anhydride (0.807 Wt, 0.481 V, 1.10 eq) in methylene chloride (1.32 Wt, 1.00 V) was added while maintaining T at −15 to −5° C. Upon complete addition, continued stirring at −5 to 0° C. over 0.5 h and monitored for complete consumption of 25 (target >97% conversion). Saturated aqueous ammonium chloride (2.67 Wt, 2.50 V) and water (1.50 Wt, 1.50 V) were added. The biphasic mixture was stirred vigorously at 18-22° C. and allowed to partition. The organic layer was aside and the aqueous layer was extracted with methylene chloride (4.7 Wt, 3.5 V). The combined organic layers were concentrated under reduced pressure (T<40° C.) to give 28 (0.95 Wt, assumed 100% theory).

N-((4aS,5R,7aS)-7a-(2-fluorophenyl)-5-methyl-4a,5,7,7a-tetrahydro-4H-furo[3,4-d][1,3]thiazin-2-yl)benzamide:
$^1$H NMR (500 MHz, CDCl$_3$) δ 8.11-8.07 (m, 2H), 7.56-7.49 (m, 1H), 7.49-7.33 (m, 4H), 7.26-7.19 (m, 1H), 7.18-7.11 (m, 1H), 4.55 (d, J=9.6 Hz, 1H), 4.55-4.46 (m, 1H), 4.16 (s, 2H), 4.06 (dd, J=9.5, 2.8 Hz, 1H), 3.26 (dd, J=13.7, 3.7 Hz, 1H), 2.93-2.87 (m, 1H), 2.84 (dd, J=13.7, 3.8 Hz, 1H), 1.42 (d, J=6.1 Hz, 3H); $^{13}$C NMR (126 MHz, cdcl$_3$) δ 174.13, 160.15 (d, J$_{CF}$=247.1 Hz), 148.20, 135.46, 132.50, 130.58 (d, J$_{CF}$=8.9 Hz), 128.97, 128.47, 128.43 (d, J$_{CF}$=3.5 Hz), 126.94 (d, J$_{CF}$=10.7 Hz), 125.00 (d, J$_{CF}$=3.4 Hz), 117.17 (d, J$_{CF}$=23.1 Hz), 77.56 (d, J$_{CF}$=5.7 Hz), 76.60, 66.88 (d, J$_{CF}$=4.4 Hz), 46.16 (d, J$_{CF}$=2.9 Hz), 23.36, 19.67.

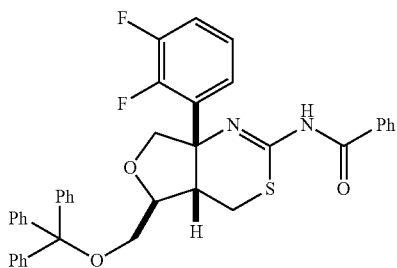

29

N-((4aS,5S,7aS)-7a-(2,3-Difluorophenyl)-5-((trityloxy) methyl)-4a,5,7,7a-tetrahydro-4H-furo[3,4-d][1,3]thiazin-2-yl)benzamide. To a solution of N-(((3S,4R,5S)-3-(2,3-difluorophenyl)-4-(hydroxymethyl)-5-((trityloxy)methyl) tetrahydrofuran-3-yl)carbamothioyl)benzamide 26 (34.0 g, 0.0511 mol, 1.0 equiv.) in CH$_2$Cl$_2$ (204 mL) at −20° C., pyridine (10.3 ml, 0.128 mol, 2.50 equiv) was added. A solution of trifluoromethanesulfonic anhydride (9.46 mL, 0.0563 mol, 1.10 equiv.) in CH$_2$Cl$_2$ (34 mL) was then added over 12 min while maintaining temperature below −17° C. The reaction was stirred for 30 min at −20° C. then allowed to warm up slowly to 5° C. Sat aq. NH$_4$Cl (85 mL) and water (32 mL) were added. The aqueous layer was then extracted with CH$_2$Cl$_2$ (68 mL). The organic phase was concentrated under reduced pressure providing the title compound 29 (33.6 g) as an orange foam.

HRMS Calculated for C$_{39}$H$_{32}$F$_2$N$_2$O$_3$S [M+H]$^+$ 647.2180. found 647.2123.

amine (49.2 g, 1.00 equiv.) were charged to a reactor and EtOAc (443 mL) was added to the mixture to give a suspension. A solution of ®T3P (105 g, 1.10 equiv, 50 wt % in EtOAc) (Archimica, Germany) was added at ambient temperature while controlling the internal temperature below 30° C. The reaction mixture was stirred at 40-45° C.>3 hours and monitored by HPLC. The reaction mixture was cooled to ambient temperature and water (98 mL) was charged. After 10-15 minutes charged 28% ammonium hydroxide (137 mL) while controlling the temperature below 30° C. Additional EtOAc (172 mL) was added and the reaction mixture was stirred for 30 minutes at ambient temperature. The aqueous phase was separated and back-extracted with EtOAc (246 mL). The organic phases were combined and washed with 15% aq. NaCl (98 mL) and water (98 mL). The organic layer was filtered over Celite (0.5 Wt) and concentrated under vacuum to obtain a beige solid (quantitative crude yield) which was recrystallized from 1-propanol to afford N-(3-((4aS,5S,7aS)-2-amino-5-(fluoromethyl)-4a,5,7,7a-tetrahydro-4H-furo[3,4-d][1,3]thiazin-7a-yl)-4-fluorophenyl)-5-(difluoromethyl)pyrazine-2-carboxamide as a tan solid (54.2 g).

$^1$H NMR (500 MHz, DMSO) δ=10.94 (s, 1H), 9.38 (d, J=0.9, 1H), 9.08 (s, 1H), 7.93 (dd, J=7.3, 2.7, 1H); 7.90-7.85 (m, 1H), 7.25 (t, J=54.0, 2H), 7.18 (dd, J=11.8, 8.8, 1H), 6.04 (s, 2H), 4.68-4.44 (m, 2H), 4.40-4.30 (m, 1H), 4.26 (d, J=8.2, 1H), 3.79 (dd, J=8.1, 3.1, 1H), 3.30 (s, 1H), 3.12 (dd, J=13.5, 3.6, 1H), 3.00 (dd, J=13.5, 3.8, 1H), 2.76 (dt, J=7.9, 3.7, 1H).

$^{13}$C NMR (126 MHz, DMSO) δ 160.90 (s), 156.22 (d, J=244.2 Hz), 149.16 (t, J=24.7 Hz), 148.46 (s), 146.91 (s), 143.69 (s), 140.35 (t, J=4.4 Hz), 134.02 (s), 130.27 (d, J=12.3 Hz), 122.46 (d, J=4.2 Hz), 121.18 (d, J=8.7 Hz), 116.26 (d, J=25.0 Hz), 112.49 (t, J=239.1 Hz), 83.53 (d, J=169.8 Hz), 78.52 (d, J=18.2 Hz), 77.55 (s), 65.61 (s), 35.59 (s), 22.93 (s).

E. Synthesis of Amino Thiazines of Formula V

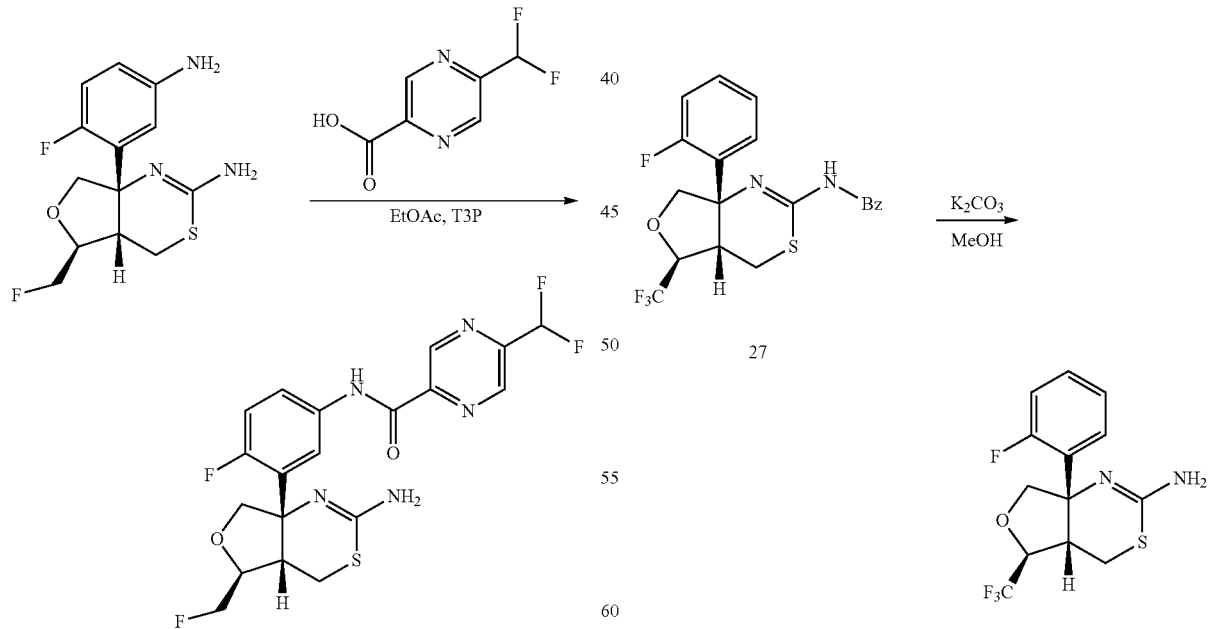

N-(3-((4aS,5S,7aS)-2-amino-5-(fluoromethyl)-4a,5,7,7a-tetrahydro-4H-furo[3,4-d][1,3]thiazin-7a-yl)-4-fluorophenyl)-5-(Difluoromethyl)pyrazine-2-carboxamide. 5-(Difluoromethyl)pyrazine-2-carboxylic acid (30.0 g, 1.05 equiv) and (4aS,5S,7aS)-7a-(5-amino-2-fluorophenyl)-5-(fluoromethyl)-4a,5,7,7a-tetrahydro-4H-furo[3,4-d][1,3]thiazin-2-

(4aS,5S,7aS)-7a-(2-Fluorophenyl)-5-(trifluoromethyl)-4a,5,7,7a-tetrahydro-4H-furo[3,4-d][1,3]thiazin-2-amine. To a solution of N-((4aS,5S,7aS)-7a-(2-fluorophenyl)-5-(trifluoromethyl)-4a,5,7,7a-tetrahydro-4H-furo[3,4-d][1,3]thiazin-2-yl)benzamide 27 (250.2 g, 589.5 mmol) in methanol (1.25 L) was added K$_2$CO$_3$ (81.5 g, 590.0 mmol). The suspension was heated to 65° C. for 6 hours. Upon cooling to ambient temperature, the solvent was evaporated under vacuum. To the resulting residue, was added 1.0 N aq NaOH (1.18 L) and THF (502 mL). The heterogeneous mixture was heated to 45° C. for 1 hour. The mixture was cooled to ambient temperature, and EtOAc (1.38 L) was added. The aqueous layer was extracted with EtOAc (0.75 L). The organics were combined, washed with saturated aq. NaHCO$_3$ (500 mL) and saturated aq. NaCl (500 mL). The organics were concentrated under vacuum to afford the title compound 30 as a brown oil (184.1 g, 91.6% yield accounting for residual solvents).

(4aS,5S,7aS)-7a-(2-Fluorophenyl)-5-(trifluoromethyl)-4a,5,7,7a-tetrahydro-4H-furo[3,4-d][1,3]thiazin-2-amine: $^1$H NMR (500 MHz, DMSO) δ 7.49-7.42 (m, 1H), 7.40-7.33 (m, 1H), 7.26-7.15 (m, 2H), 6.26 (s, 2H), 4.77-4.54 (m, 1H), 4.40 (d, J=8.0 Hz, 1H). 3.80 (dd, J=7.9, 2.3 Hz, 1H), 3.24-3.17 (m, 1H), 3.00 (dd, J=13.9, 3.2 Hz, 1H), 2.85 (dd, J=13.9, 3.9 Hz, 1H); $^{13}$C NMR (125 MHz, DMSO) δ 159.75 (d, $J_{CF}$=245.1 Hz), 149.51, 131.31 (d, $J_{CF}$=3.9 Hz), 130.13 (d, $J_{CF}$=8.8 Hz), 128.08 (d, $J_{CF}$=10.4 Hz), 128.28 (q, $J_{CF}$=282.1 Hz). 124.87 (d, $J_{CF}$=3.0 Hz), 116.80 (d, J=23.8 Hz). 78.77, 76.80 (q, $J_{CF}$=30.8 Hz), 66.31, 36.37, 23.27.

HRMS Calculated for C$_{13}$H$_{12}$F$_4$N$_2$OS [M+H]$^+$ 321.0685. found 321.0677.

(4aS,5R,7aS)-7a-(2-fluorophenyl)-5-methyl-4a,5,7,7a-tetrahydro-4H-furo[3,4-d][1,3]thiazin-2-amine: $^1$H NMR (500 MHz, CDCl$_3$) δ 7.41 (td, J=8.2, 1.6 Hz, 1H), 7.28-7.20 (m, 1H), 7.15-7.09 (m, 1H), 7.03 (ddd, J=12.4, 8.1, 0.7 Hz, 1H), 4.81-4.42 (s, 2H), 4.61 (dd, J=8.7, 0.5 Hz, 1H), 4.40-4.27 (m, 1H), 3.80 (dd, J=8.7, 2.2 Hz, 1H), 3.07 (dd, J=13.3, 3.9 Hz, 1H), 2.70 (dd, J=13.3, 3.9 Hz, 1H), 2.56-2.47 (m, 1H), 1.34 (d, J=6, 1 Hz, 3H); $^{13}$C NMR (125 MHz, CDCl$_3$) δ 160.03 (d, $J_{CF}$=247.0 Hz), 149.41, 130.73 (d, $J_{CF}$=10.0 Hz), 129.80 (d, $J_{CF}$=4.1 Hz), 128.83 (d, $J_{CF}$=8.7 Hz), 124.02 (d, $J_{CF}$=3.4 Hz), 116.38 (d, $J_{CF}$=23.5 Hz), 78.54 (d, $J_{CF}$=4.8 Hz), 76.43, 66.97 (d, $J_{CF}$=4.6 Hz), 44.50 (d, $J_{CF}$=3.7 Hz), 23.70, 19.83.

Alternate synthesis of (4aS,5R,7aS)-7a-(2-Fluorophenyl)-5-methyl-4a,5,7,7a-tetrahydro-4H-furo[3,4-d][1,3]thiazin-2-amine (31)

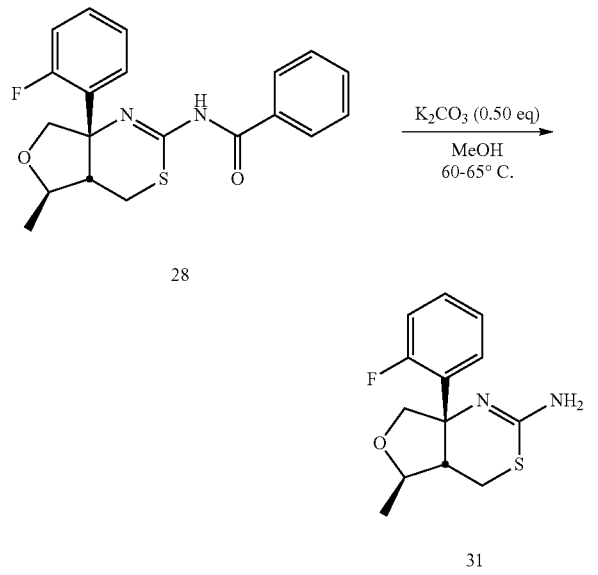

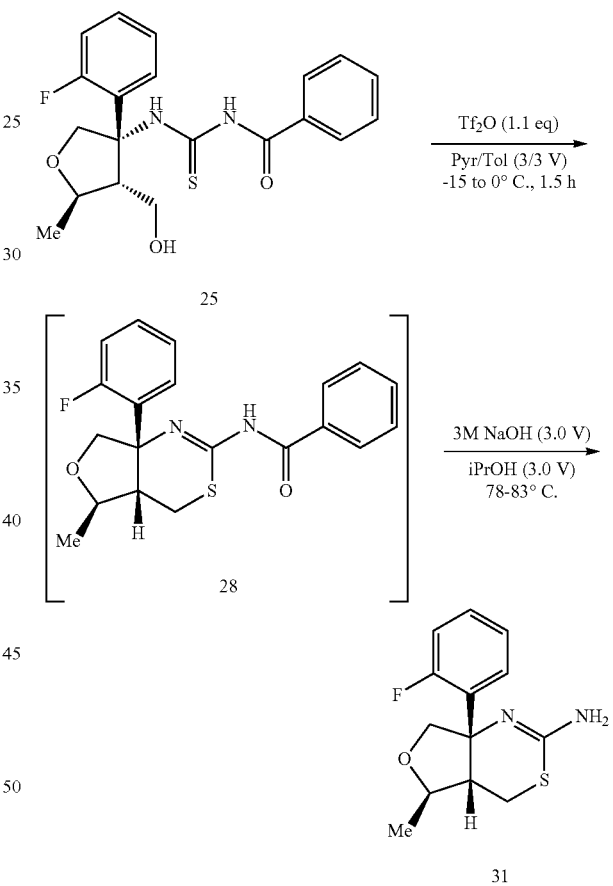

(4aS,5R,7aS)-7a-(2-Fluorophenyl)-5-methyl-4a,5,7,7a-tetrahydro-4H-furo[3,4-d][1,3]thiazin-2-amine. A reactor was charged with 28 (1.0 Wt, 1.0 eq), potassium carbonate (0.19 Wt, 0.50 eq) and MeOH (4.0 Wt, 5.0 V). The reaction mixture was heated up to 60-65° C. Continued stirring at 60-65° C. over 6 h and monitored the reaction for complete consumption of 28 (target >97% conversion). The reaction mixture was concentrated under reduced pressure (T<40° C.) to remove most of the methanol. Water (1.5 Wt, 1.5 V) was charged followed by a mixture of heptane (1.1 Wt, 1.6 V) and ethyl acetate (0.36 Wt, 0.40 V). The mixture was cooled to 0-5° C. and stirred vigorously for 1-2 h. The mixture was filtered and rinsed the reactor and filter cake with water (1.0 Wt, 1.0V) and a pre-cooled (0-5° C.) mixture of heptane (0.89 Wt, 1.3 V) and ethyl acetate (0.29 Wt, 0.32V). The solid was dried in vacuo (T<40° C.) to give 31 (0.61 Wt, 85%, pale brown solid).

A reactor was charged with thiourea 25 (1 Wt, 1 eq), pyridine (2.9 Wt, 3.0 V) and toluene (2.6 Wt, 3.0 V). The resulting mixture was cooled to below −15° C. Trifluoromethanesulfonic anhydride (0.800 Wt, 0.476 V, 1.10 eq) was added while maintaining the temperature below 0° C. Upon complete addition, stirring between −5-0° C. was continued for 1.5 h and the reaction was monitored for complete conversion (>97.0%). Toluene (5.2 Wt, 6.0 V) and 20 wt % aqueous ammonium chloride solution (4.2 Wt, 4.0 V) were added. The resulting biphasic mixture was warmed to 15-25° C., stirring for at least 15 min and then allowed to partition. The lower aqueous layer was separated, and the upper organic phase was removed and held. The aqueous layer was extracted with toluene (2.6 Wt, 3.0 V). The combined organic layers were washed with water (2.0 Wt, 2.0 V) and concentrated under reduced pressure to give crude 28 as a thick brown oil. 2-propanol (2.4 Wt, 3.0 V) and 3.0 M aqueous sodium hydroxide (3.5 Wt, 3.0 V) were added, and the resulting reaction mixture was heated to 80° C. for 6 h and monitored for complete conversion (>99.0%). Heptane (1.4 Wt, 2.0 V) and then water (10 Wt, 10 V) were then added, while keeping the internal temperature above 60° C. The resulting mixture was cooled to 0-5° C. and maintained at this temperature for at least 2 h, then filtered. The reactor and filter cake were rinsed with a mixture of water (1.8 Wt, 1.8V) and 2-propanol (0.16 Wt, 0.20 V) and then a mixture of heptane (1.2 Wt, 1.8 V) and ethyl acetate (0.18 Wt, 0.20V). The solids were dried to give isothiourea 31 (0.57 Wt, 83% yield).

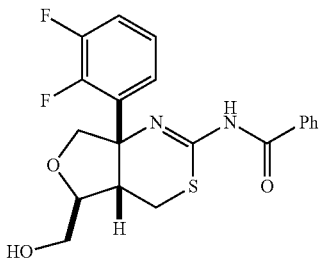

32

N-((4aS,5S,7aS)-7a-(2,3-Difluorophenyl)-5-(hydroxymethyl)-4a,5,7,7a-tetrahydro-4H-furo[3,4-d][1,3]thiazin-2-yl)benzamide. Formic acid (116 mL) was added to N-((4aS,5S,7aS)-7a-(2,3-difluorophenyl)-5-((trityloxy)methyl)-4a,5,7,7a-tetrahydro-4H-furo[3,4-d][1,3]thiazin-2-yl)benzamide 29 (33.30 g, 0.051 mol, 1.0 equiv.), the mixture was stirred at rt for 25 min. Water (17 mL) was added drop wise then the reaction was stirred for another 30 min. The resulting suspension was filtrated; the filtrate was dried by azeotropic distillation under vacuum with toluene (360 mL). Methanol (110 mL) was added followed by triethylamine (22 mL, 0.15 mol, 3.0 equiv.) and the solution was stirred for 2 hours. The solvent was removed under vacuum and chased with toluene (66 mL). The residual oil was dissolved in $CH_2Cl_2$ (250 ml) and washed successively with aq.HCl (1M, 100 mL), sat aq.NaHCO$_3$ (67 mL) and 18% aq.NaCl (67 mL). The organic phase was concentrated under reduce pressure. Toluene (66 mL) and THF (67 mL) were added to the residue then the solution was filtered through celite and concentrated under reduced pressure to yield the title compound 32 (21 g).

$^1$H NMR (500 MHz, DMSO) δ 8.11 (dd, J=16.4, 4.2 Hz, 2H), 7.70-7.58 (m, 1H), 7.57-7.44 (m, 3H), 7.43-7.34 (m, 1H), 7.34-7.26 (m, 1H), 4.43 (d, J=9.5 Hz, 1H), 4.25-4.16 (m, 1H), 4.10 (d, J=9.2 Hz, 1H), 3.59 (d, J=4.5 Hz, 2H), 3.30-3.21 (m, 1H), 3.20-3.08 (m, 2H); $^{13}$C NMR (125 MHz, DMSO) δ 169.08, 150.95 (dd, J$_{CF}$=245.8, 13.1 Hz), 148.22, 148.09 (dd, J$_{CF}$=248.7, 13.2 Hz), 133.46, 129.11, 128.99, 128.62, 125.43, 124.70, 118.16 (d, J$_{CF}$=16.9 Hz), 81.36, 75.29, 66.76, 62.39, 40.77, 24.25.

HRMS Calculated for $C_{20}H_{18}F_2N_2O_3S$ [M+H]$^+$ 405.1084. found 405.1081.

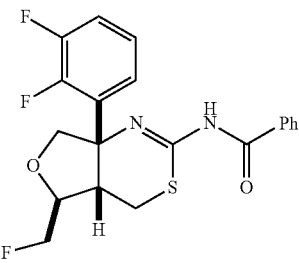

33

N-((4aS,5S,7aS)-7a-(2,3-difluorophenyl)-5-(fluoromethyl)-4a,5,7,7a-tetrahydro-4H-furo[3,4-d][1,3]thiazin-2-yl)benzamide. N-((4aS,5S,7aS)-7a-(2,3-difluorophenyl)-5-(hydroxymethyl)-4a,5,7,7a-tetrahydro-4H-furo[3,4-d][1,3]thiazin-2-yl)benzamide 32 (21.0 g, 0.519 mol, 1.0 equiv.) was dissolved in dry THF (105 mL) under a nitrogen atmosphere and the solution was cooled at 0° C. N,N-diisopropylethylamine (40.7 mL, 0.234 mol, 4.50 equiv.), triethylamine trihydrofluoride (14.0 mL, 0.0857 mol, 1.65 equiv.) and perfluorobutanesulfonyl fluoride (22.4 mL, 0.125 mol, 2.40 equiv.) were added while maintaining temperature under 5° C. The reaction was stirred for 3 hours at 0° C. then slowly warmed to room temperature and stirred for 11 hours. To the reaction mixture was charged sat.NH$_4$Cl (100 mL) followed by 2-methoxy-2-methylpropane (100 mL). The organic phase was isolated and washed with aq. HCl (1.0 M, 100 ml), concentrated and redissolved in 2-methoxy-2-methylpropane (301 ml). The organic phase was then washed with aq.HCl (1M, 63 mL), sat aq.NaHCO$_3$ (100 mL). The last aqueous layer was extracted with 2-methoxy-2-methylpropane. The combined organic phase was washed with 18% aq.NaCl (63 mL) and concentrated under reduced pressure to afford title compound 33 (19.40 g) as a foam.

N-((4aS,5 S,7aS)-7a-(2,3-difluorophenyl)-5-(fluoromethyl)-4a,5,7,7a-tetrahydro-4H-furo[3,4-d][1,3]thiazin-2-yl)benzamide: $^1$H NMR (500 MHz, DMSO) δ 8.02 (s, 2H), 7.61-7.51 (m, 1H), 7.51-7.38 (m, 3H), 7.39-7.18 (m, 2H), 4.72-4.49 (m, 2H), 4.48-4.37 (m, 1H), 4.41 (d, J=9.1 Hz, 21H), 3.04 (s, 2H); $^{13}$C NMR (125 MHz, DMSO) δ 150.92 (dd, J$_{CF}$=245.5, 13.3 Hz), 148.11 (dd, J$_{CF}$=248.2, 13.4 Hz), 132.40, 128.99, 128.63, 125.16, 124.94, 117.61, 83.64 (d, J$_{CF}$=170.2 Hz), 79.51 (d, J$_{CF}$=18.4 Hz), 76.17, 66.27, 23.67.

HRMS Calculated for $C_{20}H_{17}F_3N_2O_2S$ [M+H]$^+$ 407.1041. found 407.1024.

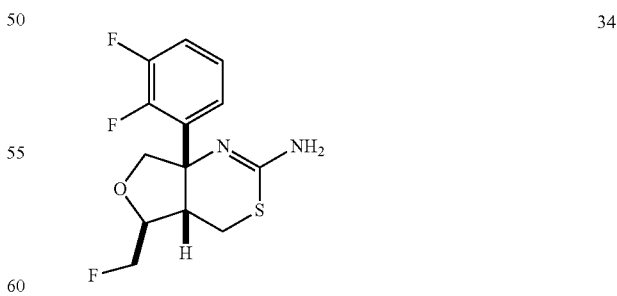

34

(4aS,5S,7aS)-7a-(2,3-Difluorophenyl)-5-(fluoromethyl)-4a,5,7,7a-tetrahydro-4H-furo[3,4-d][1,3]thiazin-2-amine. N-((4aS,5S,7aS)-7a-(2,3-difluorophenyl)-5-(fluoromethyl)-4a,5,7,7a-tetrahydro-4H-furo[3,4-d][1,3]thiazin-2-yl)benzamide 33 (19.40 g, 0.048 mol, 1.0 equiv.) was dissolved in methanol (97 mL), under nitrogen. 1,8-diazabicyclo[5.4.0]

undec-7-ene (8.92 mL, 0.060 mol, 1.25 equiv.) was added, and the solution was heated to 55-60° C. After 8 h, the reaction mixture was concentrated under reduced pressure, and the residue purified by silica gel flash column chromatography (5% to 100% EtOAc in heptane) to afford the title compound 34 (9.01 g).

(4aS,5 S,7aS)-7a-(2,3-difluorophenyl)-5-(fluoromethyl)-4a,5,7,7a-tetrahydro-4H-furo[3,4-d][1,3]thiazin-2-amine: $^1$H NMR (500 MHz, DMSO) δ 7.38-7.28 (m, 1H), 7.26-7.14 (m, 2H), 6.12 (s, 2H), 4.66-4.41 (m, 2H), 4.37-4.27 (m, 2H), 4.29 (d, J=8.2 Hz, 1H), 3.74 (dd, J=8.2, 2.6 Hz, 1H), 3.30 (s, 1H), 3.06-2.90 (m, 2H), 2.79-2.71 (m, 1H); $^{13}$C NMR (125 MHz, DMSO) δ 150.84 (dd, J=244.8, 14.0 Hz), 149.71, 148.07 (dd, $J_{CF}$=247.8, 13.4 Hz), 133.08 (d, $J_{CF}$=7.7 Hz), 125.24, 124.55 (dd, $J_{CF}$=7.2, 4.3 Hz), 116.58 (d, $J_{CF}$=17.2 Hz), 83.91 (d, $J_{CF}$=170.0 Hz), 79.12 (d, $J_{CF}$=18.2 Hz), 77.96 (d, $J_{CF}$=4.9 Hz), 66.22, 36.41 (d, $J_{CF}$=3.3 Hz), 23.40.

HRMS Calculated for $C_{13}H_{13}F_3N_2OS$ [M+H]$^+$ 303.0779. found 303.0767.

G. Synthesis of Nitrophenyl Thiazines of Formula VI

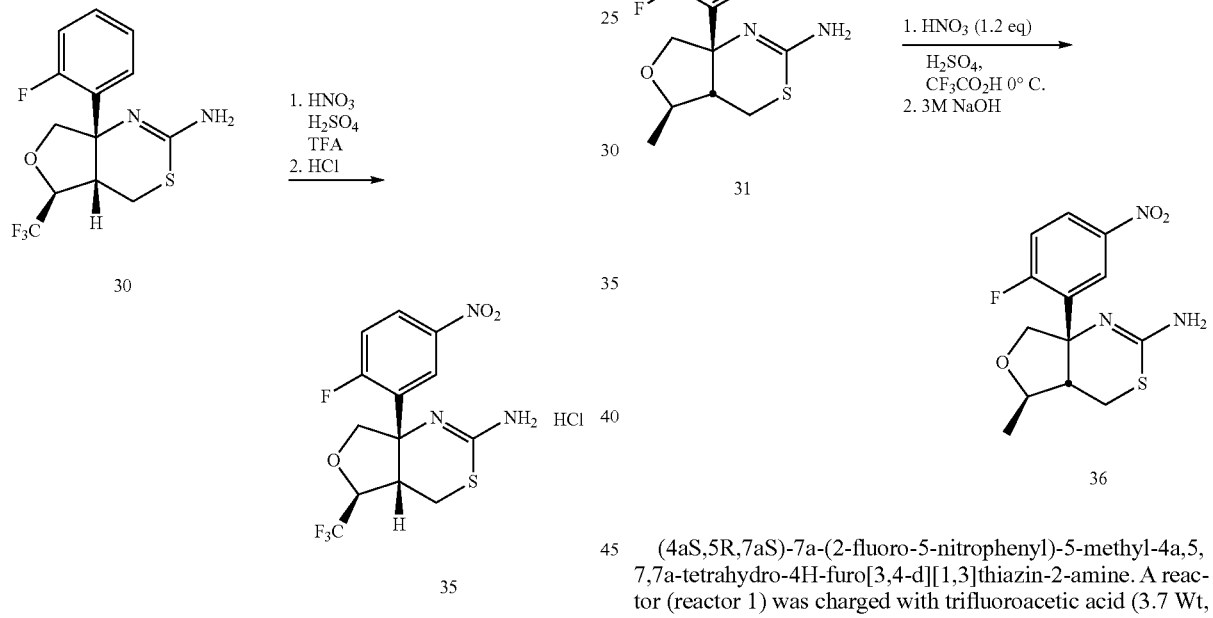

(4aS,5S,7aS)-7a-(2-Fluoro-5-nitrophenyl)-5-(trifluoromethyl)-4a,5,7,7a-tetrahydro-4H-furo[3,4-d][1,3]thiazin-2-amine hydrochloride. To a cooled vessel containing (4aS,5S,7aS)-7a-(2-fluorophenyl)-5-(trifluoromethyl)-4a,5,7,7a-tetrahydro-4H-furo[3,4-d][1,3]thiazin-2-amine 30 (184.1 g, 574.8 mmol) was added trifluoroacetic acid (0.954 kg) in portions while the temperature was maintained below 20° C. The mixture was cooled to 3.5° C. and sulfuric acid (146 mL, 2.73 mol) was added over 20 min while the temperature was maintained below 5° C. Fuming nitric acid (39.8 mL, 0.948 mol) was added over 30 min, while the temperature was maintained below 10° C. After 1.5 h at 0-10° C., the reaction mixture was slowly quenched by transferring into an aq. solution of NaOH (575 g, 14.4 mol) in water (4.6 L) cooled to 5° C. The resulting suspension was stirred for 1 h at 21° C. The suspension was then filtered and the solid rinsed with cold water (920 mL). The solid was dried under vacuum until constant weight, and then dissolved into ethanol (1.05 L). The solution was heated to 35° C., and conc. HCl (55.6 mL, 0.690 mol) was added while maintaining temperature below 40° C. The suspension was then cooled to −5° C., held for 1 hr and filtered. The solid was rinsed with cold ethanol (420 mL) and dried until constant weight to obtain the title compound 35 (185.0 g, 87.3%).

(4aS,5S,7aS)-7a-(2-Fluoro-5-nitrophenyl)-5-(trifluoromethyl)-4a,5,7,7a-tetrahydro-4H-furo[3,4-d][1,3]thiazin-2-amine hydrochloride: $^1$H NMR (500 MHz, DMSO) δ 11.80 (s, 2H), 8.45-8.36 (m, 1H), 8.31 (dd, J=6.6, 2.5 Hz, 1H), 7.66 (dd, J=11.1, 9.3 Hz, 1H), 4.96-4.72 (m, 1H), 4.58 (d, J=10, 0 Hz, 1H), 4.27 (d, J=9.9 Hz, 1H), 3.76-3.66 (m, 1H), 3.39 (dd, J=14.9, 3.6 Hz, 1H), 3.24 (dd, J=14.3, 4, 6 Hz, 1H); $^{13}$C NMR (125 MHz, DMSO) δ 168.34, 163.33 (d, $J_{CF}$=257.8 Hz), 144.58, 127.61 (d, $J_{CF}$=11.6 Hz), 125.84, 124.10, 119.28 (d, $J_{CF}$=26.5 Hz), 77.38 (q, $J_{CF}$=31.5 Hz), 75.99, 65.88 (d, $J_{CF}$=4.8 Hz), 40.36, 23.98.

HRMS Calculated for $C_{13}H_{11}F_4N_3O_3S$ [M+H]$^+$ 366.0536. found 366.0523.

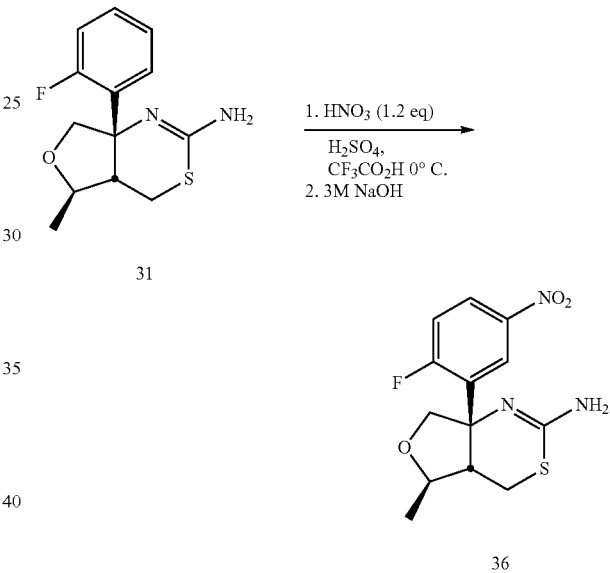

(4aS,5R,7aS)-7a-(2-fluoro-5-nitrophenyl)-5-methyl-4a,5,7,7a-tetrahydro-4H-furo[3,4-d][1,3]thiazin-2-amine. A reactor (reactor 1) was charged with trifluoroacetic acid (3.7 Wt, 2.5 V) and cool down to 0-5° C. 31 (1 Wt, 1 eq) was added portionswise with stirring, while maintaining T below 20° C. The holding vessel and reactor were rinsed with trifluoroacetic acid (1.5 Wt, 1.0 V). The mixture was cooled below 5° C. and then added sulfuric acid (1.3 Wt, 0.72 V) while maintaining T below 15° C. The resulting solution was cooled down to 0-5° C. and then added fumic nitric acid (purity >90%, 0.315 Wt, 0.210 V, 1.20 eq) while maintaining T below 25° C. Upon completed addition, continued stirring the mixture with cooling (bath T. 0-5° C.) over 0.5 h and monitored the reaction for complete consumption of 31 (target >98% conversion). Another reactor (reactor 2) was charged with 3.0 M NaOH (26 Wt, 23 V) and the mixture was cooled to 3-7° C. The reaction mixture was transferred into the second reactor while maintaining the T below 30° C. During the addition, a white precipitate was formed. Upon completed addition, continued stirring at 23-27° C. The first reactor was rinsed with water (2.0 Wt, 2.0 V), and transfer the water wash into reactor 2. Additional 3M NaOH to make the pH>12 was added if necessary. After stirring for 0.5-1 h at 23-27° C., the mixture was filtered and the reactor and filter cake were rinsed with water (4.0 Wt, 4.0 V). The filter cake was dried under reduced pressure (T<30° C.) overnight to give 36 (1.12 Wt, 96.1% yield).

(4aS,5R,7aS)-7a-(2-fluoro-5-nitrophenyl)-5-methyl-4a,5,7,7a-tetrahydro-4H-furo[3,4-d][1,3]thiazin-2-amine: $^1$H NMR (500 MHz, CDCl$_3$) δ 8.39 (dd, J=6.9, 2.9 Hz, 1H), 8.20-8.14 (m, 1H), 7.21 (dd, J=10.8, 9.0 Hz, 1H), 4.55 (dd, J=9.1, 0.9 Hz, 1H), 4.41-4.31 (m, 1H), 3.80 (dd, J=9.1, 1.8 Hz, 1H), 3.05 (dd, J=13.5, 3.8 Hz, 1H), 2.74 (dd, J=13.5, 4.1 Hz, 1H), 2.52-2.42 (m, 1H), 1.37 (d, J=6.1 Hz, 3H); $^{13}$C NMR (1256 MHz, CDCl$_3$) δ 163.56 (d, J$_{CF}$=258.9 Hz), 150.91, 144.23, 133.73 (d, J$_{CF}$=12.3 Hz), 126.05 (d, J$_{CF}$=6.2 Hz), 124.76 (d, J$_{CF}$=10.8 Hz), 117.53 (d, J$_{CF}$=26.3 Hz), 78.83 (d, J$_{CF}$=4.0 Hz), 76.96, 66.91 (d, J$_{CF}$=4.8 Hz), 45.26 (d, J$_{CF}$=3.1 Hz), 23.88, 19.63.

H. Synthesis of Diamino Thiazines of Formula VII

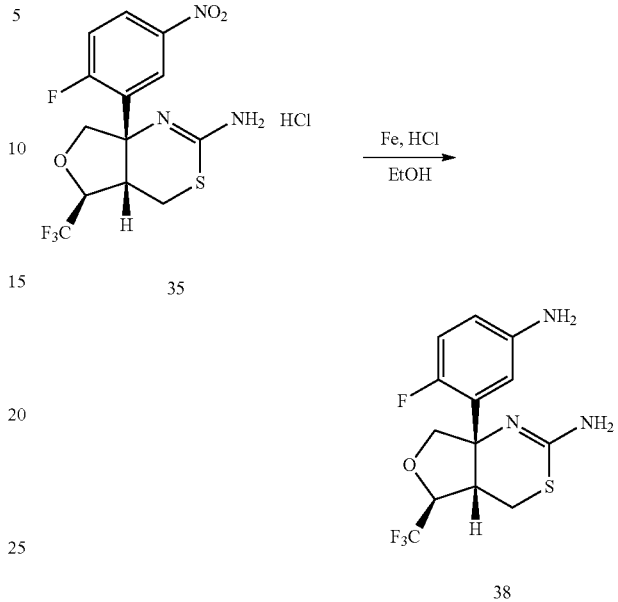

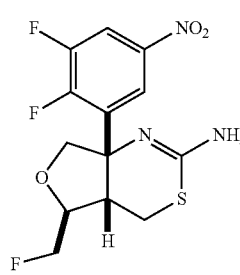

37

(4aS,5S,7aS)-7a-(2,3-Difluoro-5-nitrophenyl)-5-(fluoromethyl)-4a,5,7,7a-tetrahydro-4H-furo[3,4-d][1,3]thiazin-2-amine. (4aS,5 S,7aS)-7a-(2,3-difluorophenyl)-5-(fluoromethyl)-4a,5,7,7a-tetrahydro-4H-furo[3,4-d][1,3]thiazin-2-amine 34 (9.10 g, 0.03 mol, 1.0 equiv.) was dissolved in trifluoroacetic acid (36.4 mL), and the solution was cooled to 0° C. Sulfuric acid (conc., 12.0 mL) was added, followed by fuming nitric acid (6.9 mL) drop wise while maintaining the temperature below 5° C. After stirring at 0-5° C. for 4 h, the reaction mixture was slowly charged into a vigorously stirred solution of aq.NaOH (43.3 g in 273 mL water) while maintaining a temperature below 20° C. The mixture was extracted with CH$_2$Cl$_2$ (1×94 ml, and 2×64 mL), and the combined organic phases were washed with sat. aq. NaCl (46 mL). Celite (15.0 g) was added to the organics, and the mixture was filtered rinsing with CH$_2$Cl$_2$ (40 mL). The solvents were evaporated to afford the title compound 37 (8.3 g) which was used in the subsequent step without purification.

(4aS,5 S,7aS)-7a-(2,3-difluoro-5-nitrophenyl)-5-(fluoromethyl)-4a,5,7,7a-tetrahydro-4H-furo[3,4-d][1,3]thiazin-2-amine: $^1$H NMR (500 MHz, DMSO) δ 8.41-8.30 (m, 1H), 8.22-8.13 (m, 1H), 6.36 (s, 2H), 4.70-4.46 (m, 2H), 4.43-4.31 (m, 1H), 4.35 (d, J=8.7 Hz, 1H), 3.69 (dd, J=8.5, 1.6 Hz, 1H), 3.04-2.91 (m, 2H), 2.86-2.76 (m, 1H); $^{13}$C NMR (125 MHz, DMSO) δ 152.36 (dd, J$_{CF}$=246.8, 12.3 Hz), 151.13, 150.32 (dd, J$_{CF}$=238.2, 12.2 Hz), 143.25 (dd, J$_{CF}$=7.9, 2.5 Hz), 134.70 (d, J$_{CF}$=9.5 Hz), 121.28, 113.02 (d, J$_{CF}$=22.3 Hz), 83.74 (d, J$_{CF}$=170.1 Hz), 79.44 (d, J$_{CF}$=18.3 Hz), 78.02 (d, J=3.9 Hz), 36.96, 23.28.

HRMS Calculated for C$_{13}$H$_{12}$F$_3$N$_3$O$_3$S [M+H]$^+$ 348.0630. found 348.0614.

(4aS,5S,7aS)-7a-(5-amino-2-fluorophenyl)-5-(trifluoromethyl)-4a,5,7,7a-tetrahydro-4H-furo[3,4-d][1,3]thiazin-2-amine. Ethanol (0.975 L) was added to iron powder (62.5 g, 1.12 mol) under nitrogen atmosphere. Concentrated HCl (9.03 mL) was added at ambient temperature and the suspension was heated to 65° C. for 1.5 h. The suspension was then cooled to 50° C., and sat. aq. NH$_4$Cl (299 g) were added. The temperature of the reaction mixture was allowed to reach 50° C., and (4aS,5S,7aS)-7a-(2-fluoro-5-nitrophenyl)-5-(trifluoromethyl)-4a,5,7,7a-tetrahydro-4H-furo[3,4-d][1,3]thiazin-2-amine hydrochloride 35 (75.0 g, 187.0 mol) was added in portions while maintaining temperature below 68° C. After 30 min, ethanol (0.45 L) was added, and the reaction mixture was cooled to 20-25° C. over 1 h. The suspension was stirred for 2 h and filtered over Celite (75 g) rinsing with ethanol (0.972 L). The solution was concentrated under vacuum to a brown solid. Water (0.9 L) was added followed by 3.0 N NaOH (0.187 L, 560 mmol) while maintaining temperature below 35° C. The resulting suspension was stirred for 1 h at 20-25° C. The suspension was filtered, and the solid was rinsed with cold water (0.38 L). The solid was dried under vacuum at 40-45° C. over 24 h to obtain the title compound 38 (57.7 g, 95.5%).

(4aS,5S,7aS)-7a-(5-Amino-2-fluorophenyl)-5-(trifluoromethyl)-4a,5,7,7a-tetrahydro-4H-furo[3,4-d][1,3]thiazin-2-amine: $^1$H NMR (500 MHz, DMSO) δ 6.81 (dd, J=12.5, 8.6 Hz, 1H), 6.62 (dd, J=7.0, 2.9 Hz, 1H), 6.50-6.42 (m, 1H), 6.16 (s, 2H). 4.96 (s, 2H), 4.72-4.54 (m, 1H), 4.35 (d, J=7.8 Hz, 1H), 3.74 (dd, J=7.8, 2.5 Hz, 1H), 3.18-3.08 (m, 1H), 3.01 (dd, J=13.9, 3.0 Hz, 1H). 2.84 (dd, J=13.8, 3.8 Hz, 1H); $^{13}$C NMR (125 MHz, DMSO) δ 156.20 (d, J$_{CF}$=243.0 Hz), 148.73, 145.49, 127.86 (d, J$_{CF}$=11.0 Hz), 116.79 (d, J$_{CF}$=24.8 Hz), 116.10 (d, J$_{CF}$=3.3 Hz), 114.10 (d, J$_{CF}$=8.0 Hz), 78.89, 76.57 (q, J$_{CF}$=31.0 Hz), 66.35, 36.35, 23.11.

HRMS Calculated for C$_{13}$H$_{13}$F$_4$N$_3$OS [M+H]$^+$ 336.0794. found 336.0789.

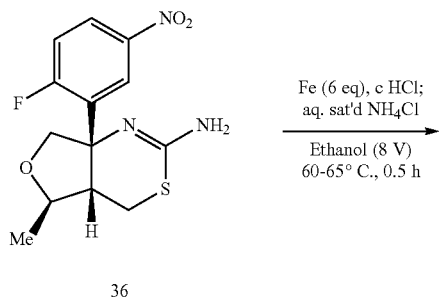

36

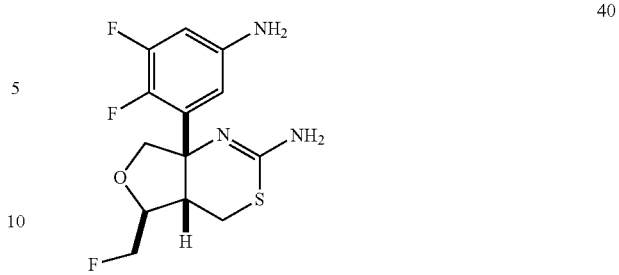

40

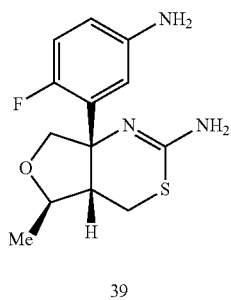

39

(4aS,5R,7aS)-7a-(5-amino-2-fluorophenyl)-5-methyl-4a,5,7,7a-tetrahydro-4H-furo[3,4-d][1,3]thiazin-2-amine. To a suspension of powder Iron (6 eq) in ethanol (8.0 V) at 18-22° C. was added conc. HCl (37 Wt %, 0.60 eq). The resulting mixture was warmed up to 65-70° C. and stirred for 2 h. Cooled down to 50-55° C. and added saturated NH4Cl solution (4.0 wt). In another reactor, 36 (1.0 Wt, 1.0 eq) was dissolved in a mixture of ethanol (5.0 V) and conc. HCl (1.0 eq). The resulting solution was added into the Iron slurry reactor while T was maintained below 65° C., rinsing with ethanol (1.0V). The reaction mixture was stirred at 55-65° C. until complete consumption of 36. The reaction mixture was diluted with 6.0V ethanol and cooled down to 15-20° C. After stirred for 1-2 h, the mixture was filtrated through a Celite pad (1.0 Wt), rinsing with 15V ethanol. Concentration in vacuo gave orange solid residue, which was dissolved in water (8V). Some orange particles were generated and removed by a polish filtration. 2V of water was used for rinse, 3M NaOH (3V) was added over 45 min at 18-25° C. The product precipitated out as a white solid. After 1-2 h stirring at 18-22° C., the mixture was filtered and the filter cake was rinsed with water three times (2V each). Drying in an oven vacuum at 45° C. overnight provided 39 as an off-white solid in 92% isolated yields.

(4aS,5R,7aS)-7a-(5-amino-2-fluorophenyl)-5-methyl-4a,5,7,7a-tetrahydro-4H-furo[3,4-d][1,3]thiazin-2-amine: $^1$H NMR (500 MHz, DMSO) δ 6.76 (dd, J=12.3, 8.6 Hz, 1H), 6.59 (dd, J=7.1, 2.8 Hz, 1H), 6.45-6.36 (m, 1H), 5.91 (s, 2H), 4.87 (s, 2H), 4.29 (d, J=8.2 Hz, 1H), 4.20-4.11 (m, 1H), 3.61 (dd, J=8.0, 2.7 Hz, 1H), 2.93 (dd, J=13.3, 3.7 Hz, 1H), 2.82 (dd, J=13.3, 3.7 Hz, 1H), 2.37-2.28 (m, 1H), 1.23 (d, J=6.1 Hz, 3H); $^{13}$C NMR (126 MHz, DMSO) δ 151.95 (d, $J_{CF}$=232.6 Hz), 148.19, 145.02, 131.37 (d, $J_{CF}$=11.3 Hz), 116.56 (d, $J_{CF}$=24.6 Hz), 115.42 (d, $J_{CF}$=3.4 Hz), 113.38 (d, $J_{CF}$=7.9 Hz), 78.56 (d, $J_{CF}$=5.4 Hz), 76.00, 66.55 (d, $J_{CF}$=4.9 Hz), 43.73 (d, $J_{CF}$=3.6 Hz), 22.96, 20.32.

(4aS,5S,7aS)-7a-(5-Amino-2,3-difluorophenyl)-5-(fluoromethyl)-4a,5,7,7a-tetrahydro-4H-furo[3,4-d][1,3]thiazin-2-amine. To iron (8.03 g, 0.144 mol, 6.0 equiv.) was added ethanol (66.56 mL), followed by conc. HCl (62%, 1.2 mL, 0.014 mol, 0.60 equiv.). The mixture was heated to 65° C. for 2 h, and then sat NH4Cl (33%, 33.3 mL) was added and the reaction temperature was maintained at 55° C. A solution of (4aS,5S,7aS)-7a-(2,3-difluoro-5-nitrophenyl)-5-(fluoromethyl)-4a,5,7,7a-tetrahydro-4H-furo[3,4-d][1,3]thiazin-2-amine 37 (8.32 g, 0.024 mol, 1.0 equiv.) and coonc. HCl (1.93 mL, 0.024 mol, 1.0 equiv.) in Ethanol (41.6 mL) was added to the iron suspension. The reaction was stirred for 30 min at 55° C., then ethanol (50 mL) was added and the suspension was allowed to cool down to 20° C., filtered through celite (8.3 g) and rinsed with ethanol (125 mL). The filtrate was concentrated under reduced pressure then water (66 mL) was added, followed by 3.0 M aq.NaOH (24 mL, 0.0179 mol, 3.0 equiv.). The resulting mixture was extracted with CH$_2$Cl$_2$ (2×83 mL). The organics phases were combined and filtered over celite and concentrated under reduce pressure to give the title compound 40 (7.60 g).

(4aS,5 S,7aS)-7a-(5-Amino-2,3-difluorophenyl)-5-(fluoromethyl)-4a,5,7,7a-tetrahydro-4H-furo[3,4-d][1,3]thiazin-2-amine: $^1$H NMR (500 MHz, DMSO) δ 6.42-6.35 (m, 2H), 6.02 (brs, 2H), 4.66-4.41 (m, 2H), 4.37-4.25 (m, 1H), 4.21 (d, J=8.0 Hz, 1H), 3.69 (dd, J=7.8, 2.2 Hz, 1H), 2.97 (qd, J=13.5, 3.4 Hz, 3H), 2.74-2.64 (m, 1H); $^{13}$C NMR (125 MHz, DMSO) δ 151.08 (dd, $J_{CF}$=240.1, 14.8 Hz), 148.88, 145.40 (d, $J_{CF}$=10.7 Hz), 139.33 (dd, $J_{CF}$=233.5, 13.8 Hz), 132.53 (d, $J_{CF}$=8.1 Hz), 109.90, 100.70 (d, $J_{CF}$=20.0 Hz), 83.99 (d, $J_{CF}$=169.9 Hz), 78.79 (d, $J_{CF}$=18.3 Hz), 77.99 (d, $J_{CF}$=5.5 Hz), 66.22, 36.24, 23.14.

HRMS Calculated for C$_{13}$H$_{14}$F$_3$N$_3$OS [M+H]$^+$ 318.0888. found 318.0874.

I. Synthesis of Compounds of Formula IX

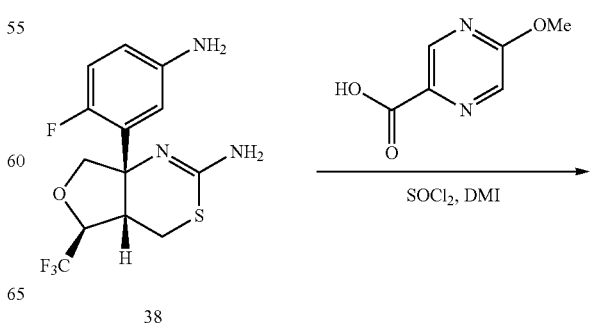

38

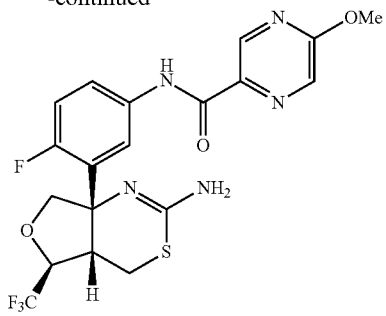

41

N-(3-((4aS,5S,7aS)-2-Amino-5-(trifluoromethyl)-4a,5,7,7a-tetrahydro-4H-furo[3,4-d][1,3]thiazin-7a-yl)-4-fluorophenyl)-5-methoxypyrazine-2-carboxamide. A suspension of 5-methoxypyrazine-2-carboxylic acid (26.29 g, 0.17 mol) in N,N'-dimethylimidazoline-2-one (160 mL) was stirred at ambient temperature for 15 min, then cooled to 2.2° C. Thionyl chloride (14.7 mL, 0.202 mol) was added while maintaining temperature under 5° C. The resulting suspension was stirred at 0-10° C. for 2 hours while it transitioned to a clear solution. In another vessel, (4aS,5S,7aS)-7a-(5-amino-2-fluorophenyl)-5-(trifluoromethyl)-4a,5,7,7a-tetrahydro-4H-furo[3,4-d][1,3]thiazin-2-amine 38 (52.0 g, 0.155 mol) was dissolved into N,N'-dimethylimidazoline-2-one (160 mL). The resulting solution was added to the solution of acyl chloride while maintaining temperature below 10° C. The reaction mixture was stirred for 30 min. Water (780 mL) was charged while maintaining temperature below 30° C. The resulting mixture was stirred for 30 min., and then EtOAc (780 mL) was added. To this mixture was added, 50% aq. NaOH (84.8 g) until the pH of the aqueous layer reached 11. The aq. layer was extracted with EtOAc (260 mL). The organics were combined, washed with sat. aq. NaCl (260 mL) and water (260 mL). The organics were filtered over Celite pad (26 g) and rinsed with EtOAc (260 mL). The organics were concentrated under vacuum to afford a solid. To the solid was added 1-propanol (728 mL), and the suspension was heated to 75° C. until a clear solution formed. The solution was cooled to −10° C. and held for 1 hour. The solid was filtered, rinsed with cold 1-propanol (104 mL) and dried under vacuum (35° C.) until constant weight to afford the title compound 41 (62.1 g, 84.9%).

N-(3-((4aS,5S,7aS)-2-Amino-5-(trifluoromethyl)-4a,5,7,7a-tetrahydro-4H-furo[3,4-d][1,3]thiazin-7a-yl)-4-fluorophenyl)-5-methoxypyrazine-2-carboxamide: $^1$H NMR (500 MHz, DMSO) δ 10.56 (s, 2H), 8.88 (d, J=1.2 Hz, 1H), 8.39 (d, J=1.2 Hz, 1H), 7.95-7.83 (m, 2H), 7.18 (dd, J=12.0, 8.8 Hz, 1H), 6.25 (s, 2H), 4.76-4.60 (m, 1H), 4.36 (d, J=8, 1 Hz, 1H), 4.01 (s, 3H), 3.88 (dd, J=7.9, 2.3 Hz, 1H), 3.23-3.11 (m, 2H), 2.91 (dd, J=13.8, 3.6 Hz, 1H); $^{13}$C NMR (125 MHz, DMSO) δ 162.11, 161.93, 156.13 (d, $J_{CF}$=242.9 Hz), 149.38, 142.01, 138.35, 135.09, 133.98, 128.53 (d, $J_{CF}$=11.6 Hz), 126.06 (q, $J_{CF}$=282.0 Hz), 123.32, 121.93 (d, $J_{CF}$=8.6 Hz), 116.76 (d, $J_{CF}$=25.1 Hz), 78.86 (d, $J_{CF}$=6.9 Hz), 76.94 (q, $J_{CF}$=30.5 Hz), 66.37, 54.75, 36.44, 23.53.

HRMS Calculated for $C_{19}H_{17}F_4N_5O_3S$ [M+H]$^+$ 472.1066. found 472.1052.

Specific optical rotation [α]$_D$+110.5 (c 0.584, MeOH)
Specific Optical Rotation Parameters:
Equipment:
  Polarimeter: Perkin Elmer, model 341 or equivalent.
  Cell: Microglass cell, 100 mm pathlength, 1.0 mL capacity, Perkin-Elmer Cat. #B001-7047.
  Balance: Calibrated analytical balance capable of weighing ±0.1 mg
  Water Bath: NESLAB RTE 1121 Chiller or equivalent.
  Volumetric glassware: Class A.
  Quartz Standard ID number 098799, or equivalent.
  Polarimeter: Perkin Elmer, model 341 or equivalent.
Reagents:
  Methanol: HPLC grade, Baker (catalog no. 9093-03) or equivalent.
Instrument Parameters:
  Lamp: Na/Hal, Perkin-Elmer Cat. #B000-8754.
  Cell: Microcell (100 mm), Perkin-Elmer Cat. #B004-1693.
  Cell Path: 100 mm (1 decimeter)
  Mode: OROT
  Wavelength: 589 nm
  Cell Temperature: 20° C.
  Integration time: 2 seconds
  Aperture: MICRO
  Water bath temperature: 20±1° C.

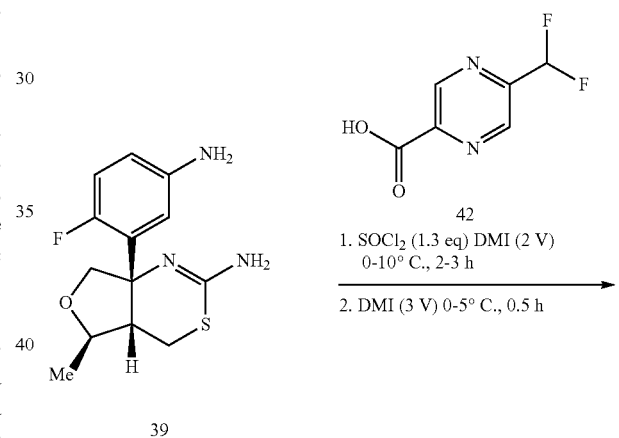

39

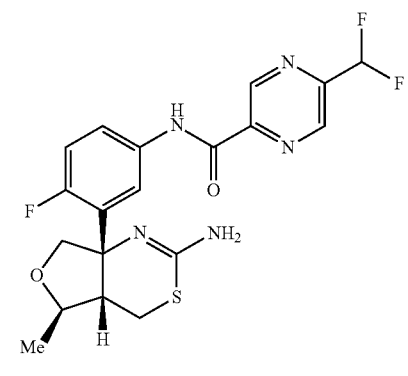

43

N-(3-((4aS,5R,7aS)-2-amino-5-methyl-4a,5,7,7a-tetrahydro-4H-furo[3,4-d][1,3]thiazin-7a-yl)-4-fluorophenyl)-5-(difluoromethyl)pyrazine-2-carboxamide. 5-(Difluoromethyl)pyrazine-2-carboxylic acid 42 (0.68 wt, 1.1 eq) was charged into a reactor and if needed, dried by azeotropic distillation with toluene. DMI (2.0V) was added and the mixture was cooled down to 0-5° C. Thionyl chloride (0.337

V, 1.30 eq) was added while keeping the internal T below 10° C. The resulting solution was stirred at 4-10° C. until the conversion was >95.0% by HPLC. The mixture was cooled down to 0° C. and a solution of 39 (1.0 Wt, 1.0 eq) in DMI (2.5V) was charged while keeping the internal temperature below 5° C. The vessel was rinsed with DMI (0.50V) and the reaction mixture was stirred until the conversion is >99%. Water (12V) was charged and the resulting mixture is stirred at 15-20° C. for 0.5 h. EtOAc (15V) and then 50% aq. NaOH (1.5 Wt, 5.3 eq) were added while keeping T below 30° C. pH was monitored to make sure that it is above 10. The aqueous phase was separated and extracted with EtOAc (5.0V). The organic layers were combined and washed with brine (5.0V) and water twice (5.0V each). The mixture was filtered through a Celite pad (0.50 Wt) rinsing with EtOAc (3.0V). The filtrate was concentrated under reduced pressure at 40-50° C. 1-Propanol (15V) was charged and the mixture was warmed up to 90-100° C. while stirring until a clear solution was obtained. The mixture was cooled down to 0-5° C. over 2 h and stirred over 1 h. The mixture was filtered, rinsing with cold 1-propanol twice (2.5V each). Drying in an oven vacuum at 45° C. overnight provided the title compound 43 as an off-white solid in 81% isolated yield.

5-(difluoromethyl)pyrazine-2-carboxylic acid: $^1$H NMR (500 MHz, DMSO) δ 4.72 (s, 1H), 4.57 (s, 1H), 4.32 (s, 1H), 2.06 (t, J=54.2 Hz, 1H); $^{13}$C NMR (125 MHz, DMSO) δ 164.34, 151.67 (t, $J_{CF}$=26.8 Hz), 145.45, 143.29, 141.04 (t, $J_{CF}$=3.4 Hz), 112.59 (t, $J_{CF}$=242.1 Hz).

N-(3-((4aS,5R,7aS)-2-amino-5-methyl-4a,5,7,7a-tetrahydro-4H-furo[3,4-d][1,3]thiazin-7a-yl)-4-fluorophenyl)-5-(difluoromethyl)pyrazine-2-carboxamide: $^1$H NMR (500 MHz, CD$_3$OD) δ 9.38 (s, 1H), 9.00 (s, 1H), 7.89-737 (m, 2H), 7.14 (dd, J=11.9, 8.8 Hz, 1H), 6.94 (t, J=54.3 Hz, 1H), 4.80 (s, 2H), 4.58 (d, J=8.9 Hz, 1H), 4.37-4.28 (m, 1H), 3.81 (dd, J=8.8, 2.4 Hz, 1H), 3.14 (dd, J=13.5, 4.0 Hz, 1H), 2.88 (dd, J=13.5, 4.1 Hz, 1H), 2.61-2.54 (m, 1H), 1.33 (d, J=6.1 Hz, 3H); $^{13}$C NMR (125 MHz, CD$_3$OD) δ 161.11, 156.94 (d, $J_{CF}$=244.9 Hz), 154.91, 150.21 (t, $J_{CF}$=25.8 Hz), 146.53, 143.30, 140.02 (t, $J_{CF}$=4.0 Hz), 133.73 (d, $J_{CF}$=2.6 Hz), 130.70 (d, $J_{CF}$=11.6 Hz), 122.05 (d, $J_{CF}$=3.9 Hz), 121.48 (d, $J_{CF}$=8.8 Hz), 116.39 (d, $J_{CF}$=25.3 Hz), 112.96 (t, $J_{CF}$=239.8 Hz), 77.56 (d, $J_{CF}$=5.3 Hz), 76.79, 66.49 (d, $J_{CF}$=4.8 Hz), 45.16, 45.13, 22.60, 18.58.

44

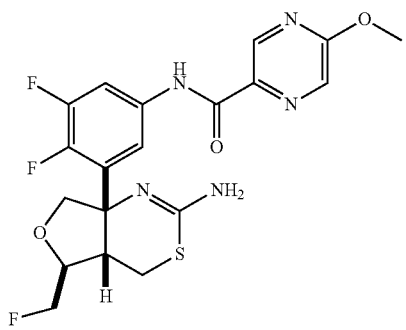

N-(3-((4aS,5S,7aS)-2-Amino-5-(fluoromethyl)-4a,5,7,7a-tetrahydro-4H-furo[3,4-d][1,3]thiazin-7a-yl)-4,5-difluorophenyl)-5-methoxypyrazine-2-carboxamide. A suspension of 5-methoxypyrazine-2-carboxylic acid (4.01 g, 0.026 mol, 1.10 equiv.) in N,N'-dimethylimidazoline-2-one (22.5 mL) was stirred at ambient temperature for 15 min, then cooled to 0° C. Thionyl chloride (2.24 mL, 0.031 mol, 1.3 equiv.) was added while maintaining temperature under 10° C. The resulting suspension was stirred at 0-10° C. for 2 hours while it transitioned to a clear solution. In another vessel, (4aS,5S,7aS)-7a-(5-amino-2,3-difluorophenyl)-5-(fluoromethyl)-4a,5,7,7a-tetrahydro-4H-furo[3,4-d][1,3]thiazin-2-amine 40 (7.60 g, 0.024 mol, 1.0 equiv.) was dissolved into N,N'-dimethylimidazoline-2-one (22.5 mL). The resulting solution was added to the solution of acyl chloride while maintaining temperature below 10° C. The reaction mixture was stirred for 30 min. Water (112 mL) was charged while maintaining temperature below 30° C. The resulting mixture was stirred for 30 min., and then EtOAc (112 mL) was added. To this mixture was added, 50% aq. NaOH (10.0 g) until the pH of the aqueous layer reached 11. The aq. layer was extracted with EtOAc (75 mL). The organics were combined, washed with sat. aq. NaCl (38 mL) and water (38 mL). The organics were filtered over a pad of silica gel (15 g) and rinsed with EtOAc (37.5 mL). The organics were concentrated under vacuum to afford a solid. To the solid was added 1-propanol (112 mL), and the suspension was heated to 100° C. The mixture was cooled to −10° C. and held for 1 hour. The solid was filtered, rinsed with cold 1-propanol (15 mL) and dried under vacuum (35° C.) until constant weight to afford the title compound 44 (8.18 g).

N-(3-((4aS,5 S,7aS)-2-Amino-5-(fluoromethyl)-4a,5,7,7a-tetrahydro-4H-furo[3,4-d][1,3]thiazin-7a-yl)-4,5-difluorophenyl)-5-methoxypyrazine-2-carboxamide: $^1$H NMR (500 MHz, DMSO) δ 10.73 (s, 1H), 8.88 (d, J=0.8 Hz, 1H), 8.39 (d, J=0.9 Hz, 1H), 8.11-7.87 (m, 1H), 7.73 (d, J=5.0 Hz, 1H), 6.07 (s, 2H), 4.68-4.44 (m, 2H), 4.41-4.28 (m, 1H), 4.23 (d, J=8.3 Hz, 1H), 4.01 (s, 3H), 3.82 (dd, J=8.1, 2.4 Hz, 1H), 3.18 (dd, J=13.5, 3.5 Hz, 1H), 3.01 (dd, J=13.5, 3.8 Hz, 1H), 2.77-2.69 (m, 1H); $^{13}$C NMR (125 MHz, DMSO) δ 162.24, 162.20, 150.05 (dd, $J_{CF}$=242.1, 14.4 Hz), 149.37, 144.42 (dd, $J_{CF}$=245.5, 13.7 Hz), 142.18, 138.09, 134.73 (dd, $J_{CF}$=10.3, 2.7 Hz), 134.03, 133.22 (d, $J_{CF}$=9.1 Hz), 116.6, 108.42 (d, $J_{CF}$=22.4 Hz), 83.98 (d, $J_{CF}$=169.9 Hz), 79.21 (d, $J_{CF}$=18.2 Hz), 77.96 (d, $J_{CF}$=5.2 Hz), 66.26, 54.78, 36.23, 23.64.

HRMS Calculated for $C_{19}H_{18}F_3N_5O_3S$ [M+H]$^+$ 454.1161. found 454.1149.

Specific optical rotation $[α]_D$+115.3 (c 0.584, MeOH)

Specific Optical Rotation Parameters:

Equipment:
Polarimeter: Perkin Elmer, model 341 or equivalent.
Cell: Microglass cell, 100 mm pathlength, 1.0 mL capacity, Perkin-Elmer Cat. # B001-7047.
Balance: Calibrated analytical balance capable of weighing ±0.1 mg
Water Bath: NESLAB RTE 1121 Chiller or equivalent.
Volumetric glassware: Class A.
Quartz Standard ID number 098799, or equivalent.
Polarimeter: Perkin Elmer, model 341 or equivalent.

Reagents:
Methanol: HPLC grade, Baker (catalog no. 9093-03) or equivalent.

Instrument Parameters:
Lamp: Na/Hal, Perkin-Elmer Cat. #B000-8754.
Cell: Microcell (100 mm), Perkin-Elmer Cat. #B004-1693.
Cell Path: 100 mm (1 decimeter)
Mode: OROT
Wavelength: 589 nm
Cell Temperature: 20° C.
Integration time: 2 seconds
Aperture: MICRO
Water bath temperature: 20±1° C.

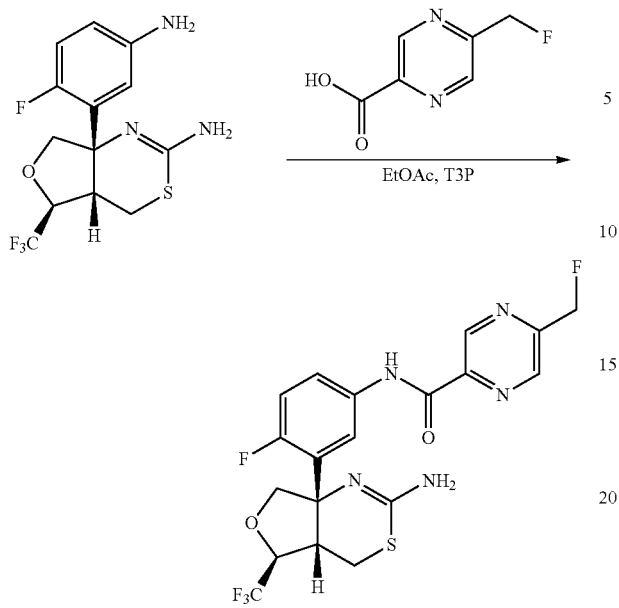

N-(3-((4aS,5S,7aS)-2-amino-5-(trifluoromethyl)-4a,5,7,7a-tetrahydro-4H-furo[3,4-d][1,3]thiazin-7a-yl)-4-fluorophenyl)-5-(fluoromethyl)pyrazine-2-carboxamide.

5-(Fluoromethyl)pyrazine-2-carboxylic acid (32.6 g, 1.05 equiv) and (4aS,5S,7aS)-7a-(5-amino-2-fluorophenyl)-5-(trifluoromethyl)-4a,5,7,7a-tetrahydro-4H-furo[3,4-d][1,3]thiazin-2-amine (70.0 g, 1.0 equiv) were charged to a reactor and EtOAc (630 mL) was added to the mixture to give a suspension. A solution of ®T3P (146 g, 1.10 equiv, 50 wt % in EtOAc) (Archimica, Germany) was added at ambient temperature while controlling the internal temperature below 30° C. The reaction mixture was stirred at 40-45° C.>3 hours and monitored by HPLC. The reaction mixture was cooled to 15-20° C. and water (140 mL) was charged. After 10-15 minutes charged 28% ammonium hydroxide (175 mL) while controlling the temperature below 30° C. EtOAc (245 mL0 was added and the reaction mixture was stirred for 30 minutes at ambient temperature. The aqueous phase was separated and back-extracted with EtOAc (490 mL). The organic phases were combined and washed with 15% aq. NaCl (140 mL) and water (140 mL). The organic layer was filtered over Celite (1.0 Wt) and rinsed with EtOAc (140 mL). The solution was concentrated under vacuum to obtain a beige solid (quantitative crude yield) which was recrystallized from 1-propanol to afford N-(3-((4aS,5S,7aS)-2-amino-5-(trifluoromethyl)-4a,5,7,7a-tetrahydro-4H-furo[3,4-d][1,3]thiazin-7a-yl)-4-fluorophenyl)-5-(fluoromethyl)pyrazine-2-carboxamide as a white solid (70.0 g).

$^1$H NMR (500 MHz, DMSO) δ 10.89 (s, 1H), 9.30 (s, 1H), 8.89 (s, 1H), 7.95 (dd, J=7.3, 2.7 Hz, 1H), 7.94-7.89 (m, 1H), 7.21 (dd, J=12, 0, 8.8 Hz, 1H), 6.22 (s, 2H), 5.71 (d, J=46.3 Hz, 2H), 4.77-4.61 (m, 1H), 4.37 (d, J=8.1 Hz, 1H), 3.87 (dd, J=8.0, 2.7 Hz, 1H), 3.20 (dt, J=7.0, 3.5 Hz, 1H), 3.15 (dd, J=13.9, 3.1 Hz, 1H), 2.91 (dd, J=13.8, 3.8 Hz, 1H). $^{13}$C NMR (126 MHz, DMSO) δ 161.32 (s), 155.82 (d, J=243.4 Hz), 153.71 (d, J=18.7 Hz), 148.77 (s), 144.71 (d, J=1.9 Hz), 143.30 (s), 141.01 (d, J=5.6 Hz), 134.36 (d, J=2.0 Hz), 128.20 (d, J=12.1 Hz), 125.57 (q, J=283.0 Hz), 123.12 (d, J=3.6 Hz), 121.64 (d, J=8.6 Hz), 116.35 (d, J=25.2 Hz), 82.55 (d, J=165.8 Hz), 78.37 (s), 76.44 (q, J=30.6 Hz), 65.89 (d, J=5.3 Hz), 35.89 (s), 23.01 (s).

We claim:

1. A compound of Formula I:

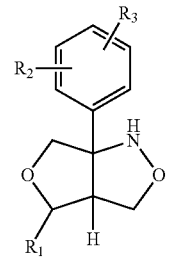

I wherein:
$R_1$ is halo-$C_{1-4}$alkyl, hydroxy-$C_{1-4}$alkyl, or —$C_{1-4}$alkyl-OR', wherein R' is an oxygen protecting group; and
$R_2$ and $R_3$ are each independently hydrogen or halo;
subject to the proviso that when one of $R_2$ or $R_3$ is ortho-fluoro, and the other is hydrogen, $R_1$ is not —$CH_2F$; and
when one of $R_2$ or $R_3$ is ortho-fluoro, the other is hydrogen, and $R_1$ is —$C_{1-4}$alkyl-OR', then R' is selected from the group consisting of methylthiomethyl, benzyloxymethyl, MPM (p-methoxybenzyloxymethyl), 2-(trimethylsilyl)ethyl), benzyl, para-methoxybenzyl, trimethylsilyl, triethylsilyl, triisopropylsilyl, TBDMS (t-butyldimethylsilyl), tribenzylsilyl, TBDPS (t-butyldiphenyl silyl), 2-trimethylsilylprop-2-enyl, t-butyl, tetrahydropyranyl and allyl, or a salt thereof.

2. The compound of claim 1, wherein the oxygen protecting group is selected from the group consisting of: Trt (triphenylmethyl), MPM (p-methoxybenzyloxymethyl)), TBDMS (t-butyldimethylsilyl), and TBDPS (t-butyldiphenyl silyl), or a salt thereof.

3. The compound of claim 1, wherein:
$R_1$ is trifluoromethyl, hydroxymethyl, monofluoromethyl, or triphenylmethoxymethyl,
or a salt thereof.

4. The compound of claim 1, wherein:
$R_1$ is trifluoromethyl, hydroxymethyl, monofluoromethyl, or triphenylmethoxymethyl;
$R_2$ is fluoro; and
$R_3$ is hydrogen or fluoro,
or a salt thereof.

5. The compound of claim 1, wherein said compound is selected from the group consisting of:

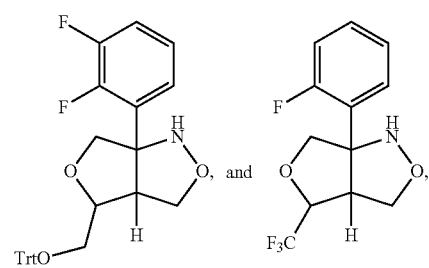

or a salt thereof.

6. A method of making a compound of Formula I,

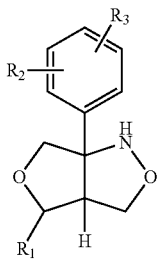

I wherein:
R$_1$ is C$_{1-4}$alkyl, halo-C$_{1-4}$alkyl, hydroxy-C$_{1-4}$alkyl, or —C$_{1-4}$alkyl-OR',
wherein R' is an oxygen protecting group; and
R$_2$ and R$_3$ are each independently hydrogen or halo,
or a salt thereof,
said method comprising heating a mixture comprising:
(i) an oxime of Formula A:

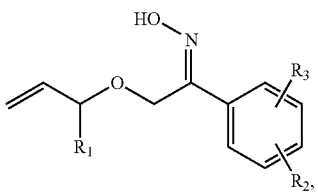

A wherein R$_1$, R$_2$ and R$_3$ are as given above;
(ii) hydroquinone; and
(iii) a hydrocarbon solvent,
to a temperature of from 90° C. to 160° C.,
to make said compound of Formula I, or a salt thereof.

7. The method of claim 6, wherein the hydrocarbon solvent is selected from the group consisting of: benzene, toluene, and xylenes.

8. The method of claim 6, wherein the hydrocarbon solvent is xylenes.

9. The method of claim 6, wherein said heating is to a temperature of from 110° C. to 140° C.

10. The method of claim 6, wherein said heating is to a temperature of from 100° C. to 120° C.

11. The method of claim 6, wherein said heating is to a temperature of from 120° C. to 140° C.

12. A method of making a compound of Formula I,

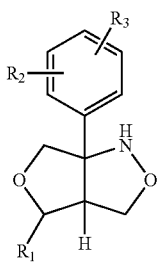

I wherein:
R$_1$ is C$_{1-4}$alkyl, halo-C$_{1-4}$alkyl, hydroxy-C$_{1-4}$alkyl, or —C$_{1-4}$alkyl-OR',
wherein R' is an oxygen protecting group; and
R$_2$ and R$_3$ are each independently hydrogen or halo,
or a salt thereof,
said method comprising heating a mixture comprising:
(i) a compound of Formula B:

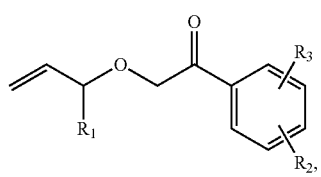

B wherein R$_1$, R$_2$ and R$_3$ are as given above;
(ii) acetate;
(iii) hydroxylamine or a salt thereof; and
(iv) a hydrocarbon solvent,
to a temperature of from 90° C. to 160° C.,
to make said compound of Formula I, or a salt thereof.

13. The method of claim 12, wherein the hydrocarbon solvent is selected from the group consisting of: benzene, toluene, and xylenes.

14. The method of claim 12, wherein the hydrocarbon solvent is toluene.

15. The method of claim 12, wherein said heating is to a temperature of from 110° C. to 140° C.

16. The method of claim 12, wherein said heating is to a temperature of from 100° C. to 120° C.

17. The method of claim 12, wherein said heating is to a temperature of from 120° C. to 140° C.

18. A method of making a compound of Formula I,

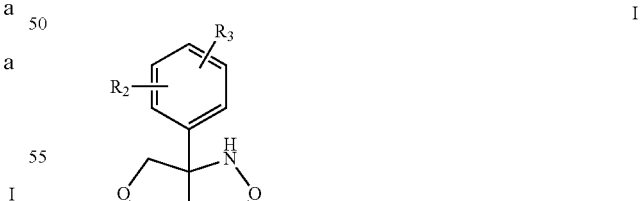

I wherein:
R$_1$ is C$_{1-4}$alkyl; and
R$_2$ and R$_3$ are each independently hydrogen or halo,
or a salt thereof, said method comprising heating a mixture comprising:
(i) an oxime of Formula A:

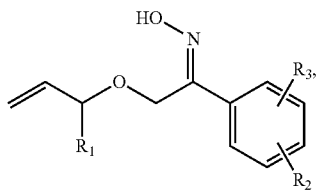

A wherein $R_1$, $R_2$ and $R_3$ are as given above;
(ii) hydroquinone; and
(iii) a hydrocarbon solvent,
to a temperature of from 90° C. to 160° C.,
to make said compound of Formula I, or a salt thereof.

19. The method of claim 18, wherein the hydrocarbon solvent is selected from the group consisting of: benzene, toluene, and xylenes.

20. The method of claim 18, wherein the hydrocarbon solvent is xylenes.

21. The method of claim 18, wherein said heating is to a temperature of from 110° C. to 140° C.

22. The method of claim 18, wherein said heating is to a temperature of from 120° C. to 140° C.

23. The method of claim 18, wherein one of $R_2$ or $R_3$ is hydrogen, and the other is fluoro.

24. A method of making a compound of Formula I,

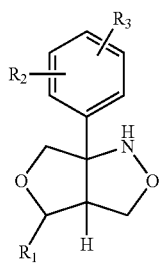

I wherein:
$R_1$ is $C_{1-4}$alkyl; and
$R_2$ and $R_3$ are each independently hydrogen or halo,
or a salt thereof,
said method comprising heating a mixture comprising:
(i) a compound of Formula B:

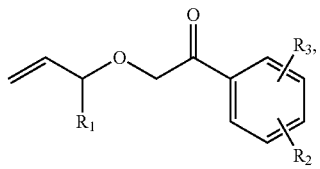

B wherein $R_1$, $R_2$ and $R_3$ are as given above;
(ii) acetate;
(iii) hydroxylamine or a salt thereof; and
(iv) a hydrocarbon solvent,
to a temperature of from 90° C. to 160° C.,
to make said compound of Formula I, or a salt thereof.

25. The method of claim 24, wherein the hydrocarbon solvent is selected from the group consisting of: benzene, toluene, and xylenes.

26. The method of claim 24, wherein the hydrocarbon solvent is toluene.

27. The method of claim 24, wherein said heating is to a temperature of from 100° C. to 120° C.

28. The method of claim 24, wherein one of $R_2$ or $R_3$ is hydrogen, and the other is fluoro.

* * * * *